(12) United States Patent
Maguire et al.

(10) Patent No.: US 7,241,273 B2
(45) Date of Patent: Jul. 10, 2007

(54) INTRA-AORTIC RENAL DELIVERY CATHETER

(75) Inventors: Mark Maguire, San Mateo, CA (US); Richard Geoffrion, Tuxedo Park, NY (US)

(73) Assignee: FlowMedica, Inc., Fremont, CA (US)

( * ) Notice: Subject to any disclaimer, the term of this patent is extended or adjusted under 35 U.S.C. 154(b) by 625 days.

(21) Appl. No.: 10/636,359

(22) Filed: Aug. 6, 2003

(65) Prior Publication Data

US 2004/0059179 A1    Mar. 25, 2004

Related U.S. Application Data

(63) Continuation of application No. 10/251,915, filed on Sep. 20, 2002, now Pat. No. 7,063,679.

(51) Int. Cl.
*A61M 37/00*    (2006.01)
(52) U.S. Cl. ..................... 604/6.16; 604/104
(58) Field of Classification Search .............. 604/27, 604/28, 6.16, 500, 48
See application file for complete search history.

(56) References Cited

U.S. PATENT DOCUMENTS

| | | | |
|---|---|---|---|
| 1,696,018 | A | 12/1928 | Schellberg |
| 2,499,045 | A | 2/1950 | Walker et al. |
| 3,455,298 | A | 7/1969 | Anstadt |
| 3,516,408 | A | 6/1970 | Montanti |
| 3,667,069 | A | 6/1972 | Blackshear et al. |

(Continued)

FOREIGN PATENT DOCUMENTS

EP    0 884 064 A2    12/1998

(Continued)

OTHER PUBLICATIONS

Bakris, et al., Renal hemodynamics in radiocontrast medium-induced renal dysfunction etc. Kidney International, vol. 56 pp. 206-210 (1999).

(Continued)

*Primary Examiner*—Kevin C. Sirmons
*Assistant Examiner*—Elizabeth R. MacNeill
(74) *Attorney, Agent, or Firm*—Townsend and Townsend and Crew LLP

(57) ABSTRACT

A renal flow system and method direct fluid into renal arteries from a location within the aorta. A renal flow assembly has a tapered tube that is adjustable between a radially collapsed condition for delivery to the location through a delivery sheath and a radially expanded condition that divides aortic flow into exterior and interior paths. The tube's wall is made from a sheet of flexible material, such as PTFE or ePTFE. Two, nickel-titanium rings radially support the tube's ends and are connected by a longitudinal spine support. A fluid delivery assembly injects drug to flow along the exterior flow path and the tubular wall directs the agent into the renal artery ostium. The tube's taper has localized shape for circumferential agent mixing to infuse both kidneys' renals. The flow assembly allows an interventional device, e.g. delivery catheter, to advance across the location while directing blood into the renals and perfusing downstream circulation. The renal flow assembly and distal device are used within a common guide sheath through a single puncture wound. Vasodilators, antioxidants, or diuretics are delivered to the kidneys to treat/prevent RCN, CHF, or ARF.

32 Claims, 23 Drawing Sheets

U.S. PATENT DOCUMENTS

| | | |
|---|---|---|
| 3,730,186 A | 5/1973 | Edmunds, Jr. et al. |
| 3,791,374 A | 2/1974 | Guarino |
| 3,481,331 A | 10/1974 | Wilder et al. |
| 3,995,623 A | 12/1976 | Blake et al. |
| 4,248,224 A | 2/1981 | Jones |
| 4,309,994 A | 1/1982 | Grunwald |
| 4,345,602 A | 8/1982 | Yoshimura et al. |
| 4,407,271 A | 10/1983 | Schiff |
| 4,423,725 A | 1/1984 | Baran et al. |
| 4,459,977 A | 7/1984 | Pizon et al. |
| 4,490,374 A | 12/1984 | Bandurco et al. |
| 4,493,697 A | 1/1985 | Krause et al. |
| 4,536,893 A | 8/1985 | Parravicini |
| 4,546,759 A | 10/1985 | Solar |
| 4,554,284 A | 11/1985 | Stringer et al. |
| 4,685,446 A | 8/1987 | Choy |
| 4,705,502 A | 11/1987 | Patel |
| 4,705,507 A | 11/1987 | Boyles |
| 4,712,551 A | 12/1987 | Rayhanabad |
| 4,714,460 A | 12/1987 | Calderon |
| 4,723,939 A | 2/1988 | Anaise |
| 4,753,221 A | 6/1988 | Kensey et al. |
| 4,781,716 A | 11/1988 | Richelsoph |
| 4,817,586 A | 4/1989 | Wampler |
| 4,834,707 A | 5/1989 | Evans |
| 4,846,831 A | 7/1989 | Skillin |
| 4,861,330 A | 8/1989 | Voss |
| 4,863,461 A | 9/1989 | Jarvik |
| 4,888,011 A | 12/1989 | Kung et al. |
| 4,902,272 A | 2/1990 | Milder et al. |
| 4,902,291 A | 2/1990 | Kolff |
| 4,906,229 A | 3/1990 | Wampler |
| 4,909,252 A | 3/1990 | Goldberger |
| 4,911,163 A | 3/1990 | Fina |
| 4,919,647 A | 4/1990 | Nash |
| 4,925,377 A | 5/1990 | Inacio et al. |
| 4,925,443 A | 5/1990 | Heilman et al. |
| 4,927,407 A | 5/1990 | Dorman |
| 4,927,412 A | 5/1990 | Menasche |
| 4,938,766 A | 7/1990 | Jarvik |
| 4,950,226 A | 8/1990 | Barron |
| 4,957,477 A | 9/1990 | Lundback |
| 4,964,864 A | 10/1990 | Summers et al. |
| 4,976,691 A | 12/1990 | Sahota |
| 4,976,692 A | 12/1990 | Atad |
| 4,990,139 A | 2/1991 | Jang |
| 4,995,864 A | 2/1991 | Bartholomew et al. |
| 5,002,531 A | 3/1991 | Bonzel |
| 5,002,532 A | 3/1991 | Gaiser et al. |
| 5,053,023 A | 10/1991 | Martin |
| 5,059,178 A | 10/1991 | Ya |
| 5,067,960 A | 11/1991 | Grandjean |
| 5,069,662 A | 12/1991 | Bodden |
| 5,069,680 A | 12/1991 | Grandjean |
| 5,073,094 A | 12/1991 | Dorman et al. |
| 5,089,019 A | 2/1992 | Grandjean |
| 5,096,442 A | 3/1992 | Grandjean |
| 5,098,370 A | 3/1992 | Rahat et al. |
| 5,112,301 A | 5/1992 | Fenton et al. |
| 5,112,349 A | 5/1992 | Summers et al. |
| 5,119,804 A | 6/1992 | Anstadt |
| 5,129,883 A | 7/1992 | Black |
| 5,131,905 A | 7/1992 | Grooters |
| 5,135,474 A | 8/1992 | Swan et al. |
| 5,158,540 A | 10/1992 | Wijay et al. |
| 5,163,910 A | 11/1992 | Schwartz et al. |
| 5,167,628 A | 12/1992 | Boyles |
| 5,180,364 A | 1/1993 | Ginsburg |
| 5,205,810 A | 4/1993 | Guiraudon et al. |
| 5,226,888 A | 7/1993 | Arney |
| 5,256,141 A | 10/1993 | Gencheff et al. |
| 5,257,974 A | 11/1993 | Cox |
| 5,282,784 A | 2/1994 | Willard |
| 5,290,227 A | 3/1994 | Pasque |
| 5,308,319 A | 5/1994 | Ide et al. |
| 5,308,320 A | 5/1994 | Safar et al. |
| 5,312,343 A | 5/1994 | Krog et al. |
| 5,320,604 A | 6/1994 | Walker et al. |
| 5,326,374 A | 7/1994 | Ilbawi et al. |
| 5,328,470 A | 7/1994 | Nabel et al. |
| 5,332,403 A | 7/1994 | Kolff |
| 5,345,927 A | 9/1994 | Bonutti |
| 5,358,519 A | 10/1994 | Grandjean |
| 5,364,337 A | 11/1994 | Guiraudon et al. |
| 5,370,617 A | 12/1994 | Sahota |
| 5,383,840 A | 1/1995 | Heilman et al. |
| 5,397,307 A | 3/1995 | Goodin |
| 5,411,479 A | 5/1995 | Bodden |
| 5,421,826 A | 6/1995 | Crocker et al. |
| 5,429,584 A | 7/1995 | Chiu |
| 5,453,084 A | 9/1995 | Moses |
| 5,464,449 A | 11/1995 | Ryan et al. |
| 5,476,453 A | 12/1995 | Mehta |
| 5,478,331 A | 12/1995 | Heflin et al. |
| 5,484,385 A | 1/1996 | Rishton |
| 5,505,701 A * | 4/1996 | Anaya Fernandez de Lomana ............ 604/101.03 |
| 5,509,428 A | 4/1996 | Dunlop ..................... 128/898 |
| 5,536,250 A | 7/1996 | Klein et al. |
| 5,558,617 A | 9/1996 | Heilman et al. |
| 5,599,306 A | 2/1997 | Klein et al. |
| 5,609,628 A | 3/1997 | Keranen |
| 5,613,949 A | 3/1997 | Miraki |
| 5,613,980 A | 3/1997 | Chauhan |
| 5,617,878 A | 4/1997 | Taheri |
| 5,643,171 A | 7/1997 | Bradshaw et al. ............. 600/1 |
| 5,643,215 A | 7/1997 | Fuhrman et al. |
| 5,702,343 A | 12/1997 | Alferness |
| 5,713,860 A | 2/1998 | Kaplan et al. |
| 5,720,735 A | 2/1998 | Dorros |
| 5,755,779 A | 5/1998 | Horiguchi |
| 5,762,599 A | 6/1998 | Sohn |
| 5,766,151 A | 6/1998 | Valley et al. |
| 5,776,190 A | 7/1998 | Jarvik |
| 5,797,876 A | 8/1998 | Spears et al. |
| 5,807,895 A | 9/1998 | Stratton et al. |
| 5,817,046 A | 10/1998 | Glickman |
| 5,902,229 A | 5/1999 | Tsitlik et al. |
| 5,902,336 A | 5/1999 | Mishkin |
| 5,913,852 A | 6/1999 | Magram |
| 5,928,132 A | 7/1999 | Leschinsky |
| 5,935,924 A | 8/1999 | Bunting et al. |
| 5,968,013 A | 10/1999 | Smith et al. |
| 5,971,910 A | 10/1999 | Tsitlik et al. |
| 5,984,955 A | 11/1999 | Wisselink |
| 6,039,721 A | 3/2000 | Johnson et al. |
| 6,068,629 A | 5/2000 | Haissaguerre et al. |
| 6,077,256 A | 6/2000 | Mann |
| 6,086,527 A | 7/2000 | Talpade |
| 6,117,117 A | 9/2000 | Mauch |
| 6,165,120 A | 12/2000 | Schweich et al. |
| 6,287,608 B1 | 9/2001 | Levin et al. |
| 6,387,037 B1 | 5/2002 | Bolling et al. |
| 6,390,969 B1 | 5/2002 | Bolling et al. |
| 6,468,241 B1 | 10/2002 | Gelfand et al. |
| 6,508,787 B2 | 1/2003 | Erbel et al. |
| 6,514,226 B1 | 2/2003 | Levin et al. |
| 6,533,747 B1 | 3/2003 | Polaschegg et al. |
| 6,537,495 B1 | 3/2003 | Cambron et al. |
| 6,554,819 B2 | 4/2003 | Reich |
| 6,592,567 B1 | 7/2003 | Levin et al. |
| 6,595,959 B1 | 7/2003 | Stratienko |
| 6,699,231 B1 | 3/2004 | Sherman et al. |
| 6,699,232 B2 | 3/2004 | Hart et al. |

| | | | |
|---|---|---|---|
| 6,733,474 | B2 | 5/2004 | Kusleika |
| 6,749,598 | B1 | 6/2004 | Keren et al. |
| 6,780,174 | B2 | 8/2004 | Mauch |
| 2001/0031907 | A1 | 10/2001 | Downey et al. |
| 2002/0090388 | A1 | 7/2002 | Humes et al. |
| 2002/0091349 | A1 | 7/2002 | Reich |
| 2002/0091355 | A1 | 7/2002 | Hayden |
| 2002/0169413 | A1* | 11/2002 | Keren et al. ............ 604/101.03 |
| 2003/0069468 | A1 | 4/2003 | Bolling et al. |
| 2003/0083617 | A1* | 5/2003 | Germain et al. ............ 604/104 |
| 2003/0144636 | A1 | 7/2003 | Liu |
| 2003/0153898 | A1 | 8/2003 | Schon et al. |
| 2004/0044302 | A1 | 3/2004 | Bernard et al. |
| 2004/0059277 | A1* | 3/2004 | Maguire et al. ............ 604/6.16 |
| 2004/0064089 | A1* | 4/2004 | Kesten et al. ............ 604/93.01 |

FOREIGN PATENT DOCUMENTS

| | | |
|---|---|---|
| GB | 2 239 675 | 7/1991 |
| WO | WO 97/11737 | 4/1997 |
| WO | WO 98/03213 | 1/1998 |
| WO | WO 98/17347 | 4/1998 |
| WO | WO 98/52639 | 11/1998 |
| WO | WO 99/22784 | 5/1999 |
| WO | WO 99/33407 | 7/1999 |
| WO | WO 99/51286 | 10/1999 |
| WO | WO 00/41612 | 7/2000 |
| WO | WO 01/083016 | 4/2001 |
| WO | WO 01/41861 A1 | 6/2001 |
| WO | WO 01/97687 | 12/2001 |
| WO | WO 01/97717 | 12/2001 |
| WO | WO 01/97878 | 12/2001 |
| WO | WO 01/97879 | 12/2001 |

OTHER PUBLICATIONS

Beregi, et al., Doppler Flow Wire Evaluation of Renal Blood Flow etc. CardioVascular and Interventional Radiology, vol. 23, pp. 340-346 (2000).

Kim et al. Fluoroscopic Landmarks for Optimal Visualization of the Proximal Renal Arteries, JVIR, 10:37-39 (1999).

Thomas, et al. Glomerrular filtration dynamics during renal vasodilation etc. Am. J. Physiol. 244:F606-F611 (1983).

Agostoni, et al., Sustained Benefit from Ultrafiltration in Moderate Congestive heart Failure, Cardiology 2001;96:183-189.

Chatterjee, Refractory heart failure-drugs and devices, European Heart Journal, 2001; 22:2227-2230.

Chu, et al. Fenoldopam in the Prevention of Contrast Media-Induced Acute Renal Failure, The Annals of Pharmacotherapy, 35:1278-1282 (2001).

Del Greco, The Kidney in Congestive Heart Failure, Modern Concepts of Cardiovascular Disease, Sep. 1975, vol. 44, No. 9, pp. 47-52.

D'Elia, et al., Nephroloxicity from angiographic Contrast Material, A prosepctive Study, Am J Med, May 1982, vol. 72, pp. 719-725.

Diaz-Sandoval, et al., Acetylcysteine to Prevent Angiography-Related Tissue Injury, The American Journal of Cardiology, Feb. 1, 2002: vol. 89, pp. 356-358.

Drescher, et al., Prevention of Contrast Medium-Induced Renal Vasospasm by Phosphodiesterase Inhibition, Invest Radiol 1998;33:858-862.

Eisenberg, et al., Renal Failure after Major Angiography Can be Avoided with Hydration, AJR, May 1981; 136:859-861.

Eisenberg, et al., Renal Failure After Major Angiography, Am J Med, Jan. 1980, vol. 68, pp. 43-46.

Elkayam, et al., Renal Hemodynaic Effects of Vasodilation with Nifedipine and Hydralazine in Patients With Heart Failure, JACC Dec. 1984; vol. 4, No. 6, pp. 1261-1267.

Elkayam, et al., Renal Vasodilatory Effect of Endothelial Stimulation in Patients with Chronic Congestive Heart Failure, J Am Coll Cardiol 1996; 28:176-182.

Freeman, et al., Nephopathy Requiring Dialysis After Percutaneous Coronary Intervention etc., Am J Cardiol, 2002;90:1068-1073.

Gerlach, et al., Contrast Medium-Induced Nephrotoxicity: Pathophysiology and Prevention, Pharmacotherapy, 2000, 20(5):540-548.

Gruberg, et al., The Prognostic Implications of Further Renal Function Deterioration Within 48 h of Interventionary etc., J Am Coll Cardiol 2000;36:1542-1548.

Halpenny, et al., The effects of fenoldopam on fenal blood flow and tubular function during aortic cross-clamping in anaesthetized dogs, Eur J Anaesthesiol, 2000 Aug;17(8);491-8 ABSTRACT ONLY.

Heyman, et al., Pathophysiology of Radiocontrast Nephropathy, A Role for Medullary Hypoxia, Invest Radiol, 1999;34:685-691.

Hobbs, et al., An update on nesiritide for treatment of decompensated heart failure, Exp. Opin. Invest. Drugs, 2001;10(5):935-942.

Hooman, Clinical Experience with the Use of Fenoldopam for Prevention of Radiocontrast Hephropathy etc, Rev Cardiovasc Med. 2001;2(suppl 1);S26-S30.

Houghton, et al., Basal and Reserve Renal Artery Blood Flow: Effect of Endothelium-Dependent and Independent Vasoactive Agonists etc., J invas Cardiol 2000;12:211-215.

Kini et al,. A Protocol for Prevention of Radiographic Contrast Nephropathy etc., Catheterization and Cardiovascular Interventions, 2002;55:169-173.

Kini, et al., Managing the High-Risk Patient: Experience with Fenoldopam, etc., Rev Cardiovasc Med. 2001;2(suppl 1):S19-S25.

Kotaro, et al., Selective Renal Vasodilation etc., The Journal of Pharmacology and Experimental Therapeutics, vol. 298, No. 3 pp. 1154-1160 (2001).

Lass, et al., Cardiovascular and Renal Hemodynamic Effects of Intravenous Infusions of the Selective DA1 Agonist etc., Circulation 1988;78:1310-1315.

Madyoon, Use of Fenoldopam to Prevent radiocontrast Nephropathy etc., Catherization and Cardiovascular Interventions 2001;53:341-345.

Margulies, et al., Induction and prevention of radiocontrast-induced nephropathy in dogs with heart failure, Kidney Int. 1990; vol. 38:1101-1108.

Margulies, et al., Intra-Arterial Atrial Natriuretic Factor (ANF) Attenuates Radiocontrast-Induced etc., Renal Pathology, unknown date, pp. 666, Abstract only.

Mason, et al., Renal Dysfunction After Arteriography, JAMA, 1985;253:1001-1004.

Mathur, et al., The effects of fenoldopam, a selective dopamine receptor agonist, on renal hemodynamics etc. Abstract only. Crit Cre Med Sep. 1999;27(9):1832-1837.

McCarthy, Animal Models in Medical Device Development and Qualification, Charles River laboratories, vol. 10(2) 1997.

McCullough, et al., Acute Renal Failure after Coronary Intervention: Incencence, Risk Factors, and Relationship to Mortality, Am J Med. 1997;103:368-375.

Mehran, et al., Radiocontrast-Induced Acute Renal Failure: Allocations and Outcomes, Rev Cardiovasc Med 2001;2(suppl 1):S9-S13.

Muller, et al., Prevention of Contrast Media-Associated Nephropathy, Arch Intern med, Feb. 2002, vol. 162, pp. 329-336.

Nohria, et al., Medical Management of Advanced Heart Failure, JAMA, Feb. 6, 2002; vol 287, No. 5, pp. 628-640.

Paganini, et al., Severity scores and outcomes with acute renal failure in the ICU setting, Contrib Nephrol 2001; 132:181-195.

Parfrey, et al., Contrast Material-Induced Renal Failure in Patients with Diabetes Mellitus, Renal Insufficiency, or Both, N Engl J Med 1989; 320:143-149.

Patel, et al. Intravenous Fenoldopam Infusion in Severe Heart Failure, Cardiovasc Drugs Ther 1993;7:97-101.

Ramanathan, et al., Ameliorating Contrast-Induced Nephropathy, Journal of Invasive Cardiology, Nov., 2001. www.invasivecardiology.com/fic_20011/jic_200111f6.html.

Rihal, et al., Incidence and Prognostic Importance of Acute Renal Failure After Percutaneous Coronary Intervention, Circulation, 2002, 105:2259-2264.

Robinson, et al., Congestive Heart Failure: Targeted Drug Therapy and Invasive Interventions, www.speroff.com/articles/Textbook/66_CHF2.htm, printed Sep. 4, 2002.

Rudnick, et al., Nephrotoxicity of ionic and noionic contrast media in 1196 patients: A randomized trial, Kidney International, 1995;47:254-261.

Schwab, et al., Contrast Nephrotoxicity: A Randomized Controlled Trial of a Nonionic and an Ionic Radiographic Contrast Agent, N Engl J Med, 1989, 320:149-153.

Shusterman, et al., Fenoldopam, But Not Nitroprusside, Improves Renal Function etc. Am J of Medicine, 95:161-168 (1993).

Solomon, et al., Effects of Saline, Mannitol, and Furosemide on Accute Decreases in Renal Function etc., N Engl J med 1994; vol. 331 No. 21 pp. 1416-1420.

Stevens, et al., A Prospective Randomized Trial of Prevention Measures in Patients at High Risk for Contrast Nephropathy, J Am Coll Cardiol, 1999;33:403-411.

Strick, et al., Direct measurement of renal medullary blood flow in the dog, Am J. Physiol. 267 (Regulatory Integrative Comp. Physiol. 36): R253-R2259, 1994.

Taliercio, et al., Risks for Renal Dysfunction with Cardiac Angiography, Annals of Internal Medicine, 1986;104:501-504.

Thomas, et al., Influence of Bradykinin and Papaverine on Renal etc., Renal Physiology, Basel 5:197-205 (1982).

Tumlin, et al., Fenoldopam mesylate blocks reductions in renal plasma flow after radiocontrast dye infusion, Am Heart J 2002;143:894-903.

Umrani, et al., Beneficial effects of fenoldopam treatment on renal function in streptozotocin-induced diabetic rats, Clin Exp Hypertens, 2002 Apr;24(3):207-19 Abstract Only.

Vari et al., Induction, prevention and mechanisms of contrast media-induced acute renal failure, Kidney International, 1988; 33:669-707.

Zacherl, et al. Periarterial Papaverine Applications Improves Intraoperative Kidney Function etc., Journal of Surgical Research 103:268-271 (2002).

Bergey, E.A. et al.; "Transhepatic Insertion of Vascular Dialysis Catheters in Children: A Safe, Life-Prolonging Procedure," Pediatr. Radiol., vol. 29, No. 1, pp. 42-50, Jan. 1999. Abstract Only.

Canaud, B. et al.; "Temporary Vascular Access for Extracorporeal Renal Replacement Therapies in Acute Renal Failure Patients," Kidney Int. Suppl., vol. 66, pp. S142-S150, May, 1998. Abstract Only.

Cohn, Jay N.; "The Management of Chronic Heart Failure," The New England Journal of Medicine, pp. 490-498, Aug. 15, 1996.

Fox, S. I.; "Mechanisms of Contraction," Human Physiology, Fourth Edition, pp. 300-323.

Garwood, Susan et al.; "Renal Preservation Strategies for High Risk Patients," University of Chico School of Medicine, Cover Page, Table of Contents Page, pp. 1-19, (1998).

Iannone, L.A. et al.—"Effect of Primary Balloon Expandable Renal Artery Stents on Long-Term Patency Renal Function and Blood Pressure in Hypertensive and Renal Insufficient Patients with Renal Artery Stenosis," Cathet. Cardiovase.

Jacobs, M.J. et al.; "Reduced Renal Failure Following Thoracoabdominal Aortic Aneurysm Repair by Selective Perfusion," Eur. J. Cardiothorac. Surg., vol. 14, No. 2, pp. 201-5, Aug. 1998. Abstract Only.

Levin, Howard R. et al.; "Reversal of Chronic Ventricular Dilation in Patients with End-Stage Cardiomyopathy by Prolonged Mechanical Unloading," vol. 91, No. 11, pp. 2717-2718, Jun. 1, 1995.

Linden, R.J. et al.; "The Nature of the Atrial Receptors Responsible for a Relfex Decrease in Activity in Renal Nerves in the Dog," The Physiological Society, pp. 31-40, (1980).

Novick, A.C.; "Atherosclerotic Ischemic Nephropathy. Epidemiology and Clinical Considerations," Urol. Clin. North AM, vol. 21, No. 2, pp. 195-200, May, 1994. Abstract Only.

Postma, C.T. et al.; "Treatment of Renal Artery Stenosis with Intra-Arterial Stents," Ned Tijdschr Geneeskd, vol. 142, No. 39, pp. 2132-7, Sep. 26, 1998. Abstract Only.

White, C.J. et al.; "Renal Artery Stent Placement: Utility in Lesions Difficult to Treat with Balloon Angioplasty," J. Am. Coll. Cardiol., vol. 30, No. 6, pp. 1445-1450, Nov. 15, 1997. Abstract Only.

Akaba, N. et al.; "A Cylinder-shaped Balloon Catheter for the Management of Dissecting Aneurysms in Acute Stage," herz, vol. 17, No. 6, pp. 390-393, Dec. 1992. Abstract Only.

Bischoff, W. et al.; "Modified in Situ Perfusion of the Kidney Using Balloon Catheters," vol. 94, No. 30, pp. 1695-1697, Oct. 21, 1976. Abstract Only.

Eisenberger, F. et al.; "transfemoral Cannulation of the Renal Vessels. Diagnostic and Therapeutic Use in Urology," Urologe [A], vol. 16, No. 1, pp. 1-5, Jan. 1977. Abstract Only.

Greco, B.A. et al.; "Atherosclerotic Ischemic Renal Disease," Am J. Kidney Dis., vol. 29, No. 2, pp. 167-187, Feb., 1997. Abstract Only.

Katsumata, T. et al.; "Newly-Developed Catheter for Cardio-Renmal Assist During Intraaortic Balloon Counterpulsation," Kyobu Geka, vol. 46, No. 9, pp. 767-770, Aug. 1993. Abstract Only.

Kehrer, G. et al.; "Construction and Experimental Application of a Catheter for Selective Arterial Kidney Perfusion in Situ," Urol. Res., vol. 13, No. 2, pp. 85-89, (1985). Abstract Only.

Kobayashi, A., et al.; "Experimental Study on the Usefulness of the Autoperfusion Balloon Catheter in Maintaining the Blood Supply to the Distal Organs," Nippon Igaku Hoshasen Gakkai Zasshi, vol. 52, No. 5, pp. 682-684, May.

Masaki, Z. et al.:"In-Situ Perfusion by Retrograde Cannullation of a Tumor Artery for Nephron-Sparing Surgery," Int. J. Urol, vol. 2, No. 3, pp. 161-165, Jul. 1995. Abstract Only.

Mathis, J.M. et al.; "Use of a Guide Catheter as a Temporary Stent During Microcatheter Intervention," AJNR Am. J. Neuroradiol, vol. 19, No. 5, pp. 932-933, May, 1998. Abstract Only.

Middleton, J.P.; "Iscremic Disease of the Kidney: How and Why to Consider Revascularization," J. Nephrol., vol. 11, No. 3, pp. 123-136, May-Jun., 1998. Abstract Only.

Seiter, H. et al.; "Modified T-Catheter and its use for Transvenous Hypothermic In Situ Perfusion in the Surgical Restoration of the Kidney with Staghorn Calculi," Z. Urol Nephrol., vol. 76, No. 6, pp. 403-406, Jun. 1983. Abstract Only.

Walker, H.S. et al.; "Use of a Balloon-Tipped Perfusion Catheter for Renal Preservation During Suprarenal Abdominal Aortic Operations," J. Vasc. Surg., vol. 2, No. 2, pp. 337-339, Mar., 1985. Abstract Only.

Williams, D.M. et al.; "Design and Testing of a High-FLO2 Autoperfusion Catheter: An Experimental Study," J. Vasc. Interv. Radiol., vol. 3, No. 2, pp. 285-290, May, 1992. Abstract Only.

* cited by examiner

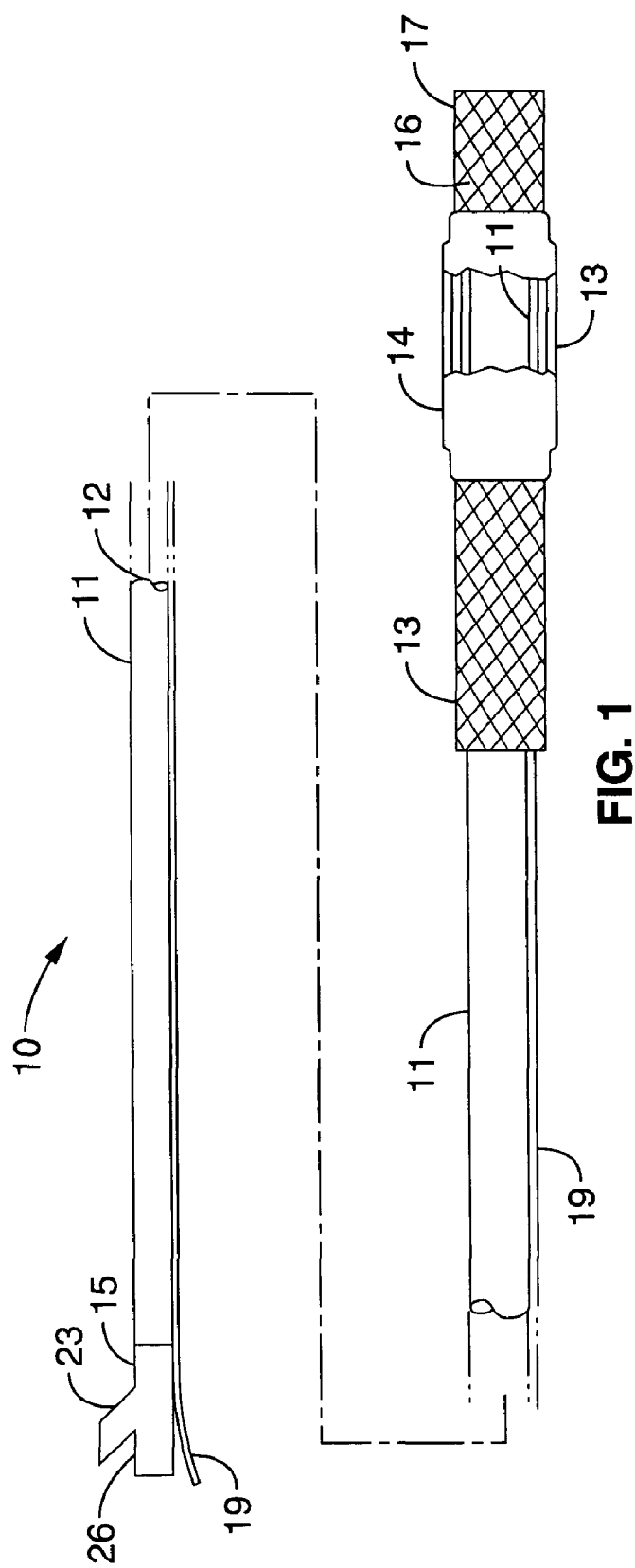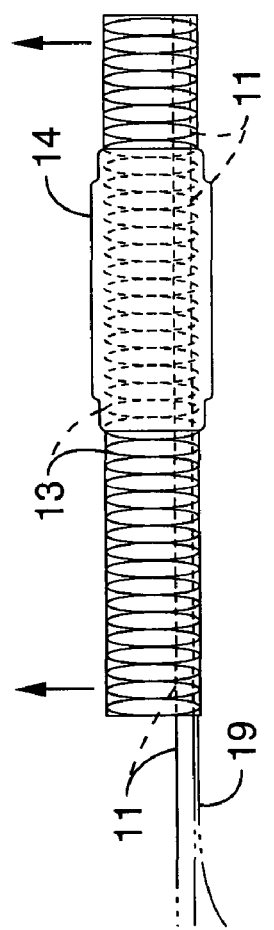
FIG. 1
FIG. 2

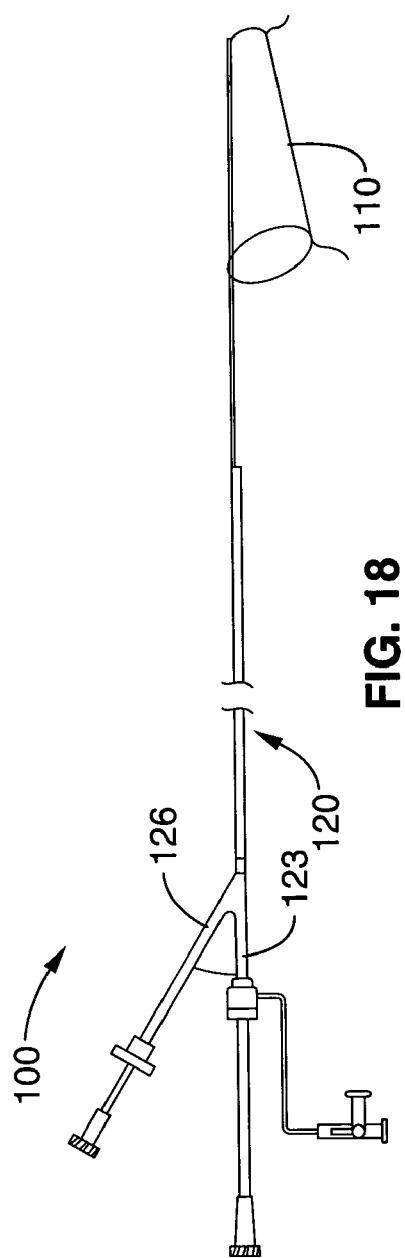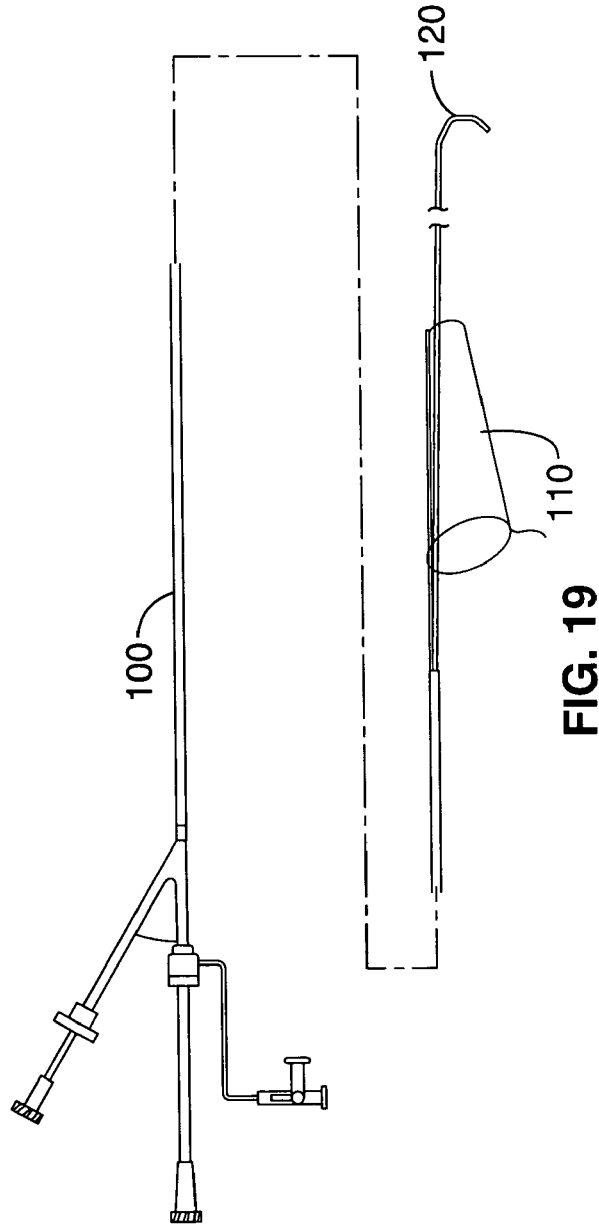

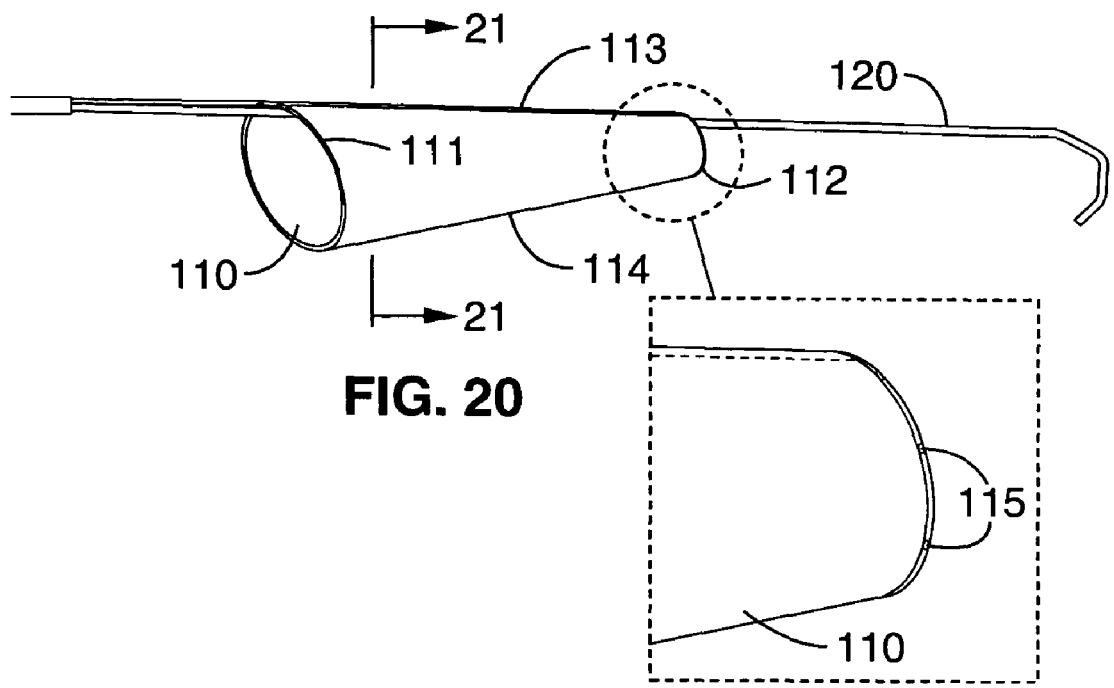
FIG. 20
FIG. 20A
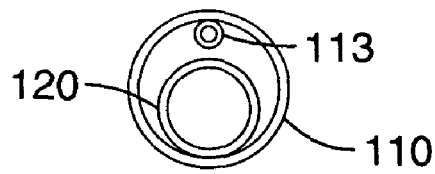
FIG. 21
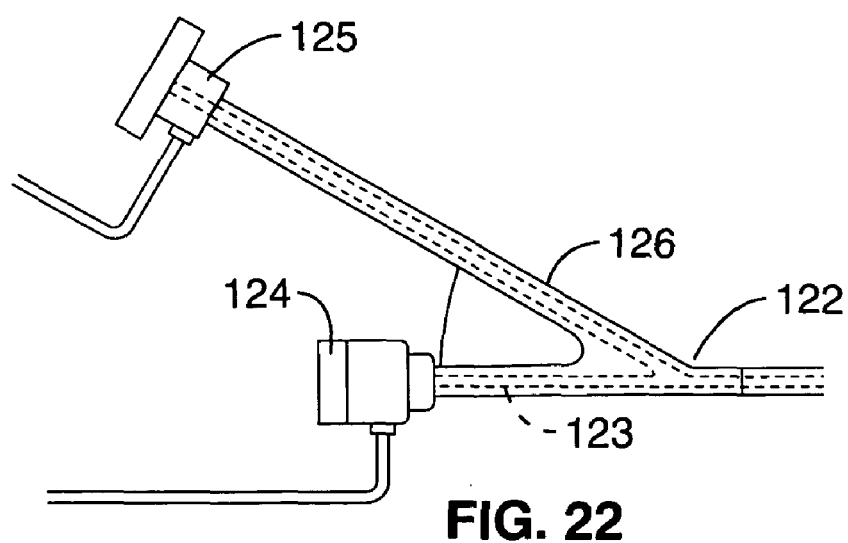
FIG. 22

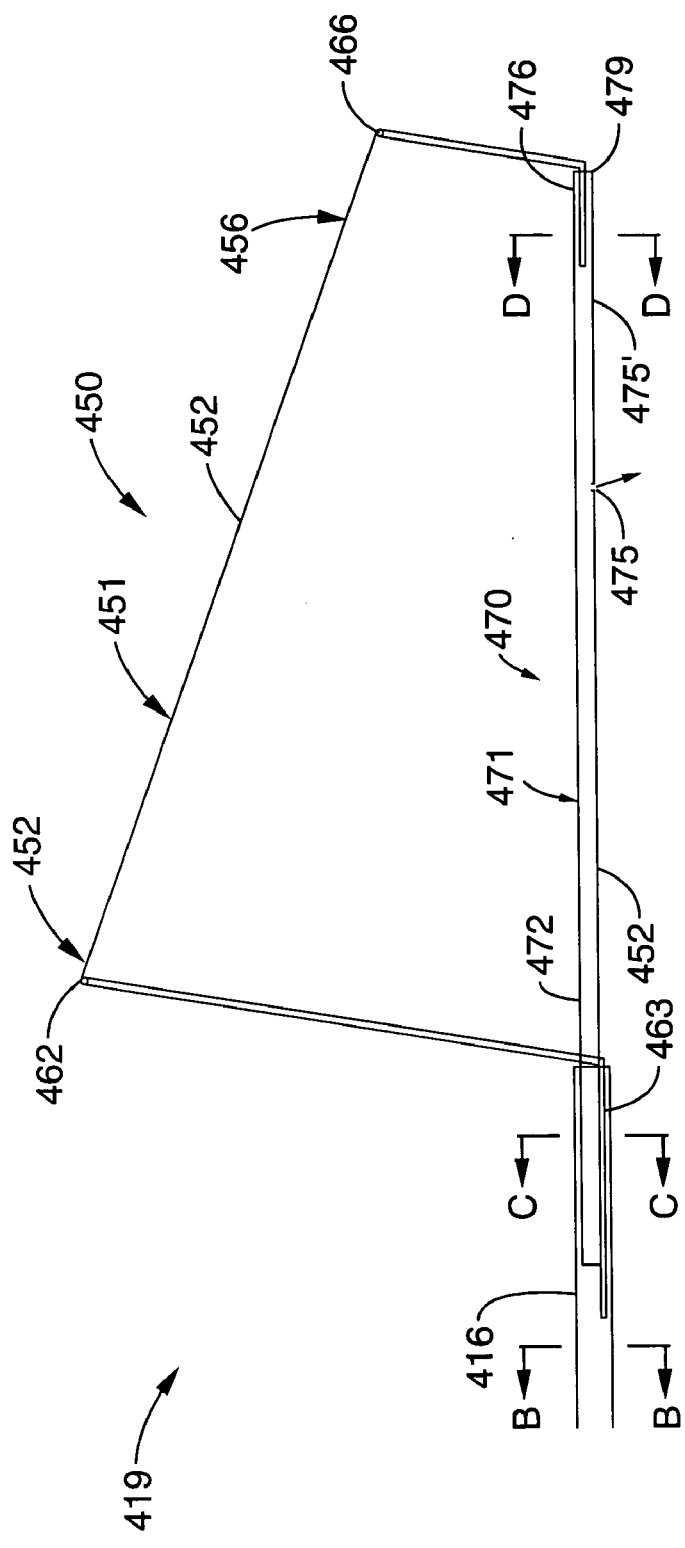
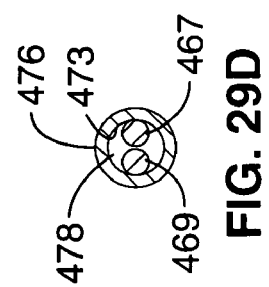
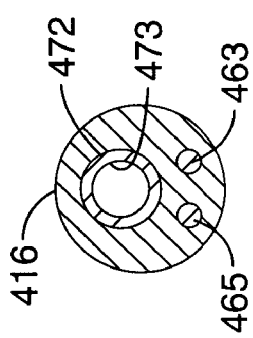
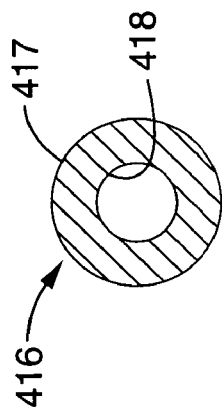
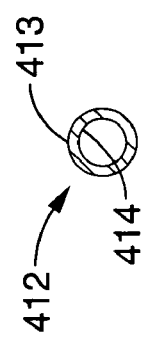

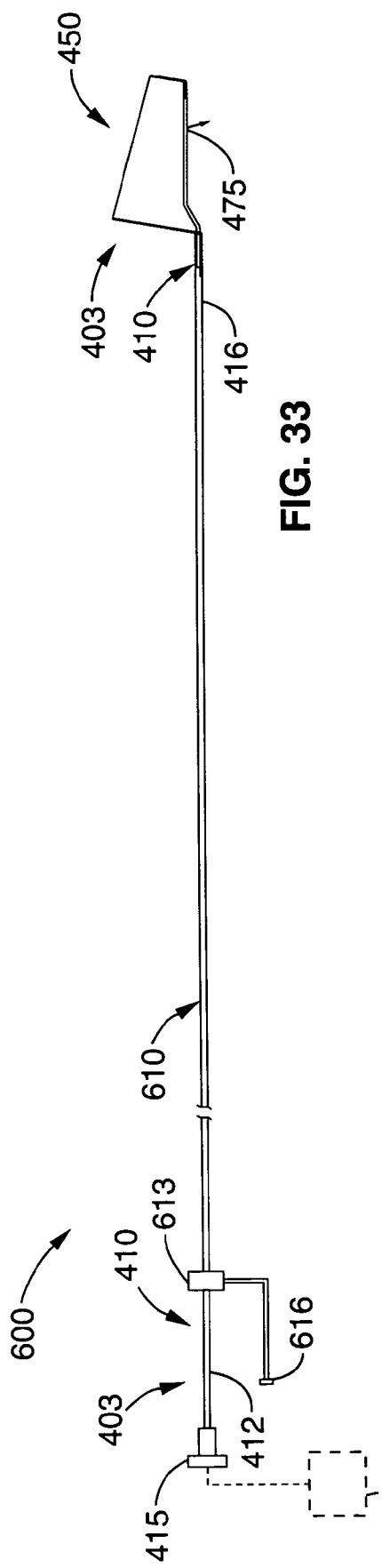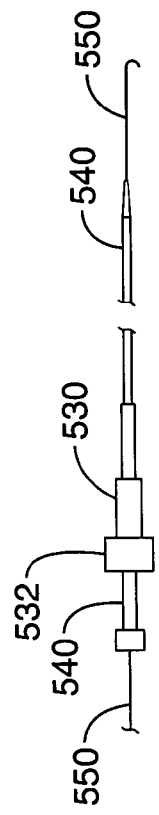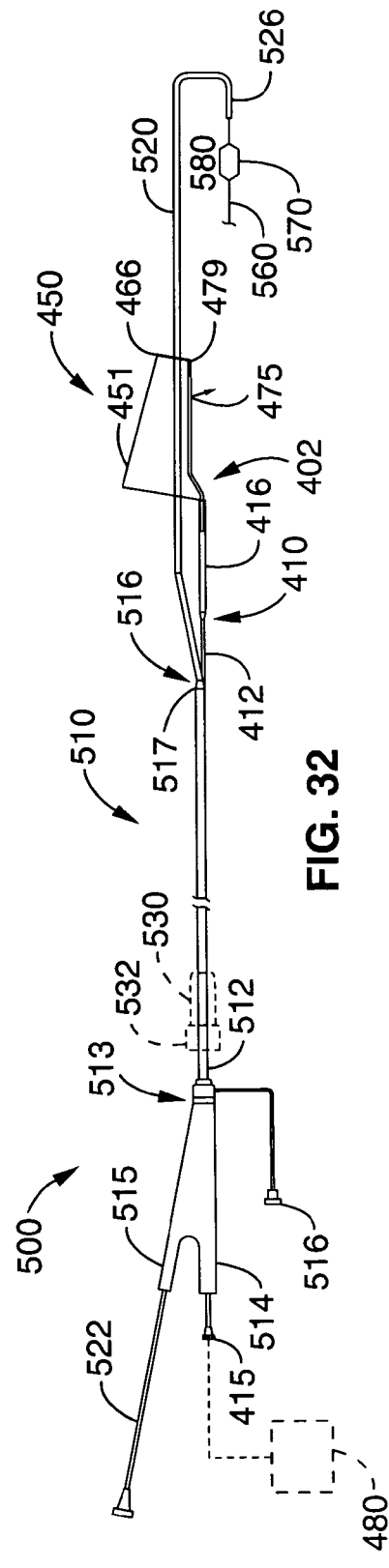
FIG. 33
FIG. 32A
FIG. 32

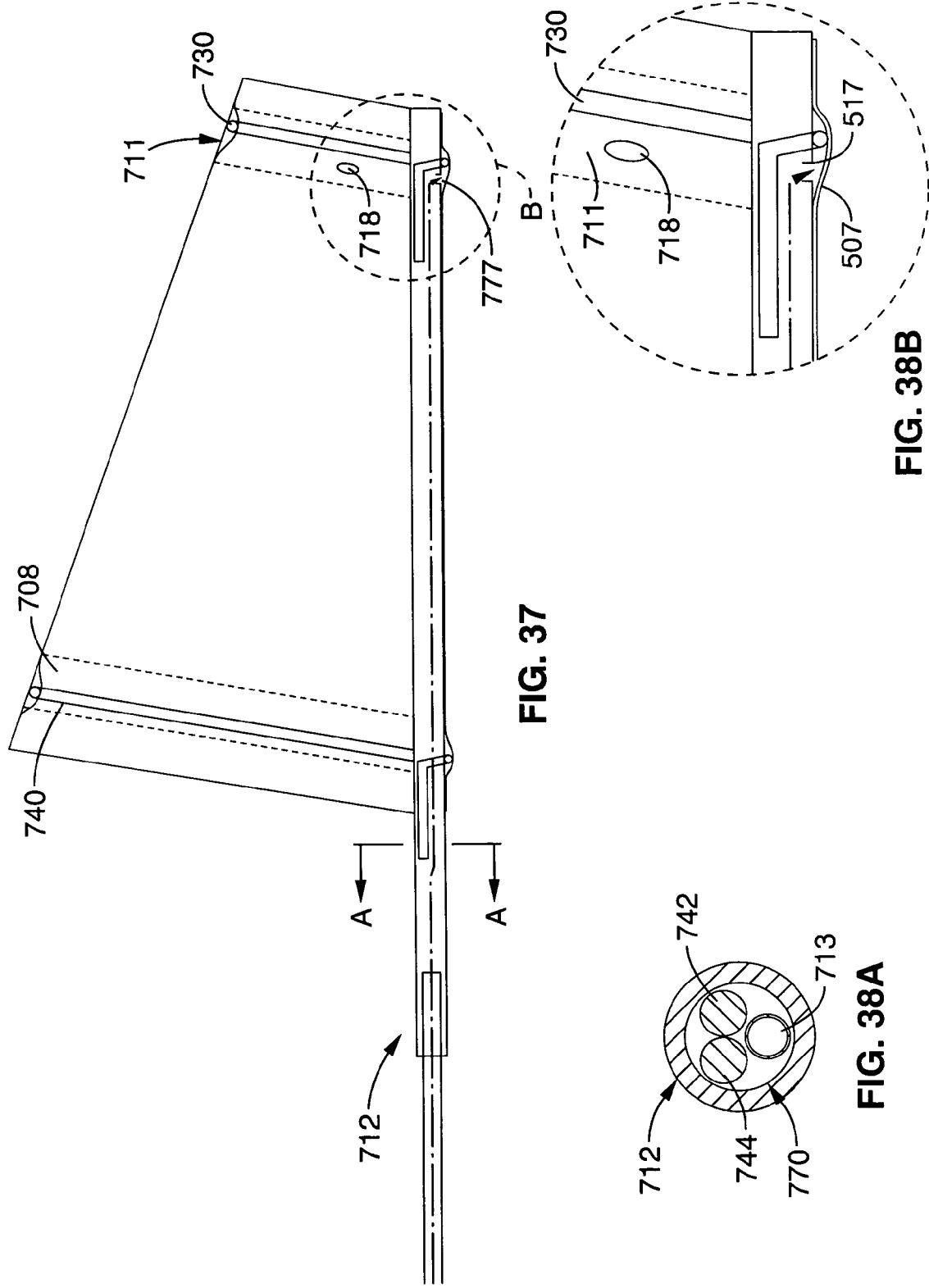

INTRA-AORTIC RENAL DELIVERY CATHETER

CROSS-REFERENCE TO RELATED APPLICATIONS

This application claims priority as a continuation of co-pending application Ser. No. 10/251,915, filed on Sep. 20, 2002, which is herein incorporated in its entirety by reference thereto.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

This invention relates to the field of medical devices, and more particularly to a system and method for locally delivering fluids or agents within the body of a patient. Still more particularly, it relates to a system and method for locally delivering fluids or agents into branch blood vessels or body lumens from a main vessel or lumen, respectively, and in particular into renal arteries extending from an aorta in a patient.

2. Description of the Background Art

Many different medical device systems and methods have been previously disclosed for locally delivering fluids or other agents into various body regions, including body lumens such as vessels, or other body spaces such as organs or heart chambers. Local "fluid" delivery systems may include drugs or other agents, or may even include locally delivering the body's own fluids, such as artificially enhanced blood transport (e.g. either entirely within the body such as directing or shunting blood from one place to another, or in extracorporeal modes such as via external blood pumps etc.). Local "agent" delivery systems are herein generally intended to relate to introduction of a foreign composition as an agent into the body, which may include drug or other useful or active agent, and may be in a fluid form or other form such as gels, solids, powders, gases, etc. It is to be understood that reference to only one of the terms fluid, drug, or agent with respect to local delivery descriptions may be made variously in this disclosure for illustrative purposes, but is not generally intended to be exclusive or omissive of the others; they are to be considered interchangeable where appropriate according to one of ordinary skill unless specifically described to be otherwise.

In general, local agent delivery systems and methods are often used for the benefit of achieving relatively high, localized concentrations of agent where injected within the body in order to maximize the intended effects there and while minimizing unintended peripheral effects of the agent elsewhere in the body. Where a particular dose of a locally delivered agent may be efficacious for an intended local effect, the same dose systemically delivered would be substantially diluted throughout the body before reaching the same location. The agent's intended local effect is equally diluted and efficacy is compromised. Thus systemic agent delivery requires higher dosing to achieve the required localized dose for efficacy, often resulting in compromised safety due to for example systemic reactions or side effects of the agent as it is delivered and processed elsewhere throughout the body other than at the intended target.

Various diagnostic systems and procedures have been developed using local delivery of dye (e.g. radiopaque "contrast" agent) or other diagnostic agents, wherein an external monitoring system is able to gather important physiological information based upon the diagnostic agent's movement or assimilation in the body at the location of delivery and/or at other locations affected by the delivery site. Angiography is one such practice using a hollow, tubular angiography catheter for locally injecting radiopaque dye into a blood chamber or vessel, such as for example coronary arteries in the case of coronary angiography, or in a ventricle in the case of cardiac ventriculography.

Other systems and methods have been disclosed for locally delivering therapeutic agent into a particular body tissue within a patient via a body lumen. For example, angiographic catheters of the type just described above, and other similar tubular delivery catheters, have also been disclosed for use in locally injecting treatment agents through their delivery lumens into such body spaces within the body. More detailed examples of this type include local delivery of thrombolytic drugs such as TPA™, heparin, cumadin, or urokinase into areas of existing clot or thrombogenic implants or vascular injury. In addition, various balloon catheter systems have also been disclosed for local administration of therapeutic agents into target body lumens or spaces, and in particular associated with blood vessels. More specific previously disclosed of this type include balloons with porous or perforated walls that elute drug agents through the balloon wall and into surrounding tissue such as blood vessel walls. Yet further examples for localized delivery of therapeutic agents include various multiple balloon catheters that have spaced balloons that are inflated to engage a lumen or vessel wall in order to isolate the intermediate catheter region from in-flow or out-flow across the balloons. According to these examples, a fluid agent delivery system is often coupled to this intermediate region in order to fill the region with agent such as drug that provides an intended effect at the isolated region between the balloons.

The diagnosis or treatment of many different types of medical conditions associated with various different systems, organs, and tissues, may also benefit from the ability to locally deliver fluids or agents in a controlled manner. In particular, various conditions related to the renal system would benefit a great deal from an ability to locally deliver of therapeutic, prophylactic, or diagnostic agents into the renal arteries.

Acute renal failure ("ARF") is an abrupt decrease in the kidney's ability to excrete waste from a patient's blood. This change in kidney function may be attributable to many causes. A traumatic event, such as hemorrhage, gastrointestinal fluid loss, or renal fluid loss without proper fluid replacement may cause the patient to go into ARF. Patients may also become vulnerable to ARF after receiving anesthesia, surgery, or α-adrenergic agonists because of related systemic or renal vasoconstriction. Additionally, systemic vasodilation caused by anaphylaxis, and anti-hypertensive drugs, sepsis or drug overdose may also cause ARF because the body's natural defense is to shut down, i.e., vasoconstrict, non-essential organs such as the kidneys. Reduced cardiac output caused by cardiogenic shock, congestive heart failure, pericardial tamponade or massive pulmonary embolism creates an excess of fluid in the body, which can exacerbate congestive heart failure. For example, a reduction in blood flow and blood pressure in the kidneys due to reduced cardiac output can in turn result in the retention of excess fluid in the patient's body, leading, for example, to pulmonary and systemic edema.

Previously known methods of treating ARF, or of treating acute renal insufficiency associated with congestive heart failure ("CHF"), involve administering drugs. Examples of such drugs that have been used for this purpose include, without limitation: vasodilators, including for example papavarine, fenoldopam, calcium channel blockers, atrial natriuretic peptide (ANP), acetylcholine, nifedipine, nitroglycerine, nitroprusside, adenosine, dopamine, and theophylline; antioxidants, such as for example acetylcysteine; and diuretics, such as for example mannitol, or furosemide. However, many of these drugs, when administered in systemic doses, have undesirable side effects. Additionally, many of these drugs would not be helpful in treating other causes of ARF. While a septic shock patient with profound systemic vasodilation often has concomitant severe renal vasoconstriction, administering vasodilators to dilate the renal artery to a patient suffering from systemic vasodilation would compound the vasodilation system wide. In addition, for patients with severe CHF (e.g., those awaiting heart transplant), mechanical methods, such as hemodialysis or left ventricular assist devices, may be implemented. Surgical device interventions, such as hemodialysis, however, generally have not been observed to be highly efficacious for long-term management of CHF. Such interventions would also not be appropriate for many patients with strong hearts suffering from ARF.

The renal system in many patients may also suffer from a particular fragility, or otherwise general exposure, to potentially harmful effects of other medical device interventions. For example, the kidneys as one of the body's main blood filtering tools may suffer damage from exposed to high density radiopaque contrast dye, such as during coronary, cardiac, or neuro angiography procedures. One particularly harmful condition known as "radiocontrast nephropathy" or "RCN" is often observed during such procedures, wherein an acute impairment of renal function follows exposure to such radiographic contrast materials, typically resulting in a rise in serum creatinine levels of more than 25% above baseline, or an absolute rise of 0.5 mg/dl within 48 hours. Therefore, in addition to CHF, renal damage associated with RCN is also a frequently observed cause of ARF. In addition, the kidneys' function is directly related to cardiac output and related blood pressure into the renal system. These physiological parameters, as in the case of CHF, may also be significantly compromised during a surgical intervention such as an angioplasty, coronary artery bypass, valve repair or replacement, or other cardiac interventional procedure. Therefore, the various drugs used to treat patients experiencing ARF associated with other conditions such as CHF have also been used to treat patients afflicted with ARF as a result of RCN. Such drugs would also provide substantial benefit for treating or preventing ARF associated with acutely compromised hemodynamics to the renal system, such as during surgical interventions.

There would be great advantage therefore from an ability to locally deliver such drugs into the renal arteries, in particular when delivered contemporaneous with surgical interventions, and in particular contemporaneous with radiocontrast dye delivery. However, many such procedures are done with medical device systems, such as using guiding catheters or angiography catheters having outer dimensions typically ranging between about 4 French to about 12 French, and ranging generally between about 6 French to about 8 French in the case of guide catheter systems for delivering angioplasty or stent devices into the coronary or neurovascular arteries (e.g. carotid arteries). These devices also are most typically delivered to their respective locations for use (e.g. coronary ostia) via a percutaneous, translumenal access in the femoral arteries and retrograde delivery upstream along the aorta past the region of the renal artery ostia. A Seldinger access technique to the femoral artery involves relatively controlled dilation of a puncture hole to minimize the size of the intruding window through the artery wall, and is a preferred method where the profiles of such delivery systems are sufficiently small. Otherwise, for larger systems a "cut-down" technique is used involving a larger, surgically made access window through the artery wall.

Accordingly, a local renal agent delivery system for contemporaneous use with other retrogradedly delivered medical device systems, such as of the types just described above, would preferably be adapted to: allow for such interventional device systems, in particular of the types and dimensions just described, to pass upstream across the renal artery ostia (a) while the agent is being locally delivered into the renal arteries, and (b) while allowing blood to flow downstream across the renal artery ostia, and (c) in an overall cooperating system that allows for Seldinger femoral artery access. Each one of these features (a), (b), or (c), or any sub-combination thereof, would provide significant value to patient treatment; a local renal delivery system providing for the combination of all three features is so much the more valuable.

Notwithstanding the clear needs for and benefits that would be gained from such local drug delivery into the renal system, the ability to do so presents unique challenges as follows.

In one regard, the renal arteries extend from respective ostia along the abdominal aorta that are significantly spaced apart from each other circumferentially around the relatively very large aorta. Often, these renal artery ostia are also spaced from each other longitudinally along the aorta with relative superior and inferior locations. This presents a unique challenge to locally deliver drugs or other agents into the renal system on the whole, which requires both kidneys to be fed through these separate respective arteries via their uniquely positioned and substantially spaced apart ostia. This becomes particularly important where both kidneys may be equally at risk, or are equally compromised, during an invasive upstream procedure—or, of course, for any other indication where both kidneys require local drug delivery. Thus, an appropriate local renal delivery system for such indications would preferably be adapted to feed multiple renal arteries perfusing both kidneys.

In another regard, mere local delivery of an agent into the natural, physiologic blood flow path of the aorta upstream of the kidneys may provide some beneficial, localized renal delivery versus other systemic delivery methods, but various undesirable results still arise. In particular, the high flow aorta immediately washes much of the delivered agent beyond the intended renal artery ostia. This reduces the amount of agent actually perfusing the renal arteries with reduced efficacy, and thus also produces unwanted loss of the agent into other organs and tissues in the systemic circulation (with highest concentrations directly flowing into downstream circulation).

In still a further regard, various known types of tubular local delivery catheters, such as angiographic catheters, other "end-hole" catheters, or otherwise, may be positioned with their distal agent perfusion ports located within the renal arteries themselves for delivering agents there, such as via a percutaneous translumenal procedure via the femoral arteries (or from other access points such as brachial arteries, etc.). However, such a technique may also provide less than completely desirable results.

For example, such seating of the delivery catheter distal tip within a renal artery may be difficult to achieve from within the large diameter/high flow aorta, and may produce harmful intimal injury within the artery. Also, where multiple kidneys must be infused with agent, multiple renal arteries must be cannulated, either sequentially with a single delivery device, or simultaneously with multiple devices. This can become unnecessarily complicated and time consuming and further compound the risk of unwanted injury from the required catheter manipulation. Moreover, multiple dye injections may be required in order to locate the renal ostia for such catheter positioning, increasing the risks associated with contrast agents on kidney function (e.g. RCN)—the very organ system to be protected by the agent delivery system in the first place. Still further, the renal arteries themselves, possibly including their ostia, may have pre-existing conditions that either prevent the ability to provide the required catheter seating, or that increase the risks associated with such mechanical intrusion. For example, the artery wall may be diseased or stenotic, such as due to atherosclerotic plaque, clot, dissection, or other injury or condition. Finally, among other additional considerations, previous disclosures have yet to describe an efficacious and safe system and method for positioning these types of local agent delivery devices at the renal arteries through a common introducer or guide sheath shared with additional medical devices used for upstream interventions, such as angiography or guide catheters. In particular, to do so concurrently with multiple delivery catheters for simultaneous infusion of multiple renal arteries would further require a guide sheath of such significant dimensions that the preferred Seldinger vascular access technique would likely not be available, instead requiring the less desirable "cut-down" technique.

In addition to the various needs for locally delivering agents into branch arteries described above, much benefit may also be gained from simply locally enhancing blood perfusion into such branches, such as by increasing the blood pressure at their ostia. In particular, such enhancement would improve a number of medical conditions related to insufficient physiological perfusion into branch vessels, and in particular from an aorta and into its branch vessels such as the renal arteries.

Certain prior disclosures have provided surgical device assemblies and methods intended to enhance blood delivery into branch arteries extending from an aorta. For example, intra-aortic balloon pumps (IABPs) have been disclosed for use in diverting blood flow into certain branch arteries. One such technique involves placing an IABP in the abdominal aorta so that the balloon is situated slightly below (proximal to) the branch arteries. The balloon is selectively inflated and deflated in a counterpulsation mode (by reference to the physiologic pressure cycle) so that increased pressure distal to the balloon directs a greater portion of blood flow into principally the branch arteries in the region of their ostia. However, the flow to lower extremities downstream from such balloon system can be severely occluded during portions of this counterpulsing cycle. Moreover, such previously disclosed systems generally lack the ability to deliver drug or agent to the branch arteries while allowing continuous and substantial downstream perfusion sufficient to prevent unwanted ischemia.

It is further noted that, despite the renal risks described in relation to radiocontrast dye delivery, and in particular RCN, in certain circumstances local delivery of such dye or other diagnostic agents is indicated specifically for diagnosing the renal arteries themselves. For example, diagnosis and treatment of renal stenosis, such as due to atherosclerosis or dissection, may require dye injection into a subject renal artery. In such circumstances, enhancing the localization of the dye into the renal arteries may also be desirable. In one regard, without such localization larger volumes of dye may be required, and the dye lost into the downstream aortic flow may still be additive to impacting the kidney(s) as it circulates back there through the system. In another regard, an ability to locally deliver such dye into the renal artery from within the artery itself, such as by seating an angiography catheter there, may also be hindered by the same stenotic condition requiring the dye injection in the first place (as introduced above). Still further, patients may have stent-grafts that may prevent delivery catheter seating.

Notwithstanding the interest and advances toward locally delivering agents for treatment or diagnosis of organs or tissues, the previously disclosed systems and methods summarized immediately above generally lack the ability to effectively deliver agents from within a main artery and locally into substantially only branch arteries extending therefrom while allowing the passage of substantial blood flow and/or other medical devices through the main artery past the branches. This is in particular the case with previously disclosed renal treatment and diagnostic devices and methods, which do not adequately provide for local delivery of agents into the renal system from a location within the aorta while allowing substantial blood flow continuously downstream past the renal ostia and/or while allowing distal medical device assemblies to be passed retrogradedly across the renal ostia for upstream use. Much benefit would be gained if agents, such as protective or therapeutic drugs or radiopaque contrast dye, could be delivered to one or both of the renal arteries in such a manner.

Several more recently disclosed advances have included local flow assemblies using tubular members of varied diameters that divide flow within an aorta adjacent to renal artery ostia into outer and inner flow paths substantially perfusing the renal artery ostia and downstream circulation, respectively. Such disclosures further include delivering fluid agent primarily into the outer flow path for substantially localized delivery into the renal artery ostia. These disclosed systems and methods represent exciting new developments toward localized diagnosis and treatment of pre-existing conditions associated with branch vessels from main vessels in general, and with respect to renal arteries extending from abdominal aortas in particular.

However, such previously disclosed designs would still benefit from further modifications and improvements in order to: maximize mixing of a fluid agent within the entire circumference of the exterior flow path surrounding the tubular flow divider and perfusing multiple renal artery ostia; use the systems and methods for prophylaxis and protection of the renal system from harm, in particular during upstream interventional procedures; maximize the range of useful sizing for specific devices to accommodate a wide range of anatomic dimensions between patients; and optimize the construction, design, and inter-cooperation between system components for efficient, atraumatic use.

A need still exists for improved devices and methods for locally delivering agents principally into the renal arteries of a patient from a location within the patient's aorta adjacent the renal artery ostia along the aorta wall while at least a portion of aortic blood flow is allowed to perfuse downstream across the location of the renal artery ostia and into the patient's lower extremities.

A need still exists for improved devices and methods for substantially isolating first and second portions of aortic blood flow at a location within the aorta of a patient adjacent the renal artery ostia along the aorta wall, and directing the first portion into the renal arteries from the location within the aorta while allowing the second portion to flow across the location and downstream of the renal artery ostia into the patient's lower extremities. There is a further benefit and need for providing passive blood flow along the isolated paths and without providing active in-situ mechanical flow support to either or both of the first or second portions of aortic blood flow. Moreover, there is a further need to direct the first portion of blood along the first flow path in a manner that increases the pressure at the renal artery ostia.

A need still exists for improved devices and methods for locally delivering agents such as radiopaque dye or drugs into a renal artery from a location within the aorta of a patient adjacent the renal artery's ostium along the aorta wall, and without requiring translumenal positioning of an agent delivery device within the renal artery itself or its ostium.

A need still exists for improved devices and methods for locally isolating delivery of fluids or agents such as radiopaque dye or drugs simultaneously into multiple renal arteries feeding both kidneys of a patient using a single delivery device and without requiring translumenal positioning of multiple agent delivery devices respectively within the multiple renal arteries themselves.

A need still exists for improved devices and methods for locally isolating delivery of fluids or agents into the renal arteries of a patient from a location within the patient's aorta adjacent the renal artery ostia along the aorta wall, and while allowing other treatment or diagnostic devices and systems, such as angiographic or guiding catheter devices and related systems, to be delivered across the location.

A need still exists for improved devices and methods for locally delivering fluids or agents into the renal arteries from a location within the aorta of a patient adjacent to the renal artery ostia along the aorta wall, and other than as a remedial measure to treat pre-existing renal conditions, and in particular for prophylaxis or diagnostic procedures related to the kidneys.

A need still exists for improved devices and methods for locally isolating delivery of fluids or agents into the renal arteries of a patient in order to treat, protect, or diagnose the renal system adjunctive to performing other contemporaneous medical procedures such as angiograms other translumenal procedures upstream of the renal artery ostia.

A need still exists for improved devices and methods for delivering both a local renal drug delivery system and at least one adjunctive distal interventional device, such as an angiographic or guiding catheter, through a common delivery sheath.

A need also still exists for improved devices and methods for delivering both a local renal drug delivery system and at least one adjunctive distal interventional device, such as an angiographic or guiding catheter, through a single access site, such as a single femoral arterial puncture.

A need also still exists for improved devices and methods for treating, and in particular preventing, ARF, and in particular relation to RCN or CHF, by locally delivering renal protective or ameliorative drugs into the renal arteries, such as contemporaneous with radiocontrast injections such as during angiography procedures.

In addition to these particular needs for selective fluid delivery into a patient's renal arteries via their ostia along the aorta, other similar needs also exist for locally isolated fluid delivery into other branch vessels or lumens extending from other main vessels or lumens, respectively, in a patient.

BRIEF SUMMARY OF THE INVENTION

The various aspects, modes, features, variations, and embodiments of the present invention variously address the yet unmet needs described above as follows.

One aspect of the invention is a renal flow system with a renal flow device that provides substantially isolated, local delivery of fluids into the renal system from within the aorta and that also cooperates with an interventional medical device for performing interventional procedures upstream from the location. The renal flow device includes a renal flow assembly that is adapted to be positioned at a location within the aorta adjacent to at least one renal artery ostium and to locally direct a volume of fluid from the location and substantially into the at least one renal artery while allowing a substantial volume of aortic blood to flow downstream across the location. While the renal flow device is providing local renal fluid delivery from the location within the aorta, it also allows the interventional medical device to be positioned across the location with its distal end positioned at an upstream location that is upstream from the renal artery ostium, and also with the interventional device's proximal end positioned externally of the patient's body.

In one mode of this system, the interventional device is a delivery catheter with a delivery lumen extending between proximal and distal ports located on proximal and distal end portions, respectively, of the delivery catheter.

In another mode, the renal flow assembly is located along a distal end portion of a delivery shaft and is adjustable between a first configuration and a second configuration. In the first configuration, the renal flow assembly is adapted to be delivered to the location through a guide lumen of a guide sheath. The renal flow assembly is adapted to be adjusted to the second configuration at the location so that the assembly divides the aorta at the location into a first flow path and a second flow path. The renal flow assembly also directs a first volume of aortic blood flowing along the first flow path to flow substantially into only the at least one renal artery ostium, and also allows a second volume of aortic blood flowing along the second flow path to flow substantially downstream across the location.

In one embodiment of this mode, the renal flow assembly is adapted to allow the interventional device such as a delivery catheter to be positioned across the location within the second flow path.

In another embodiment of this mode, the renal flow assembly also allows the delivery catheter to be positioned across the location within the second flow path while at the same time allowing a substantial volume of blood to continue to flow downstream across the location through the second flow path sufficient to prevent substantial downstream ischemia.

In a further mode, the system further includes a guide sheath with a guide lumen having an inner diameter. Both the renal flow device and the interventional device are delivered to the location through the guide lumen.

In one embodiment of this mode, the inner diameter of the guide lumen is greater than a first sum of an outer diameter of the proximal end portion of the delivery shaft of the renal flow device plus an outer diameter of the delivery catheter. However, the inner diameter of the guide lumen is less than a second sum of an outer diameter of the renal flow assembly in the first configuration plus the outer diameter of the delivery catheter.

Further to this mode, the guide sheath is adapted to deliver the distal end portion of the renal flow device through the guide lumen with the renal flow assembly in the first configuration such that the renal flow assembly may be extended distally from the guide lumen at the location in the second configuration. The guide sheath also delivers the delivery catheter through the guide lumen to the location while the renal flow assembly is in the second configuration distally from the guide lumen at the location.

In various further embodiments of this mode, the inner diameter of the guide lumen may be between about 6 French and about 12 French; or the outer diameter of the proximal end portion of the delivery shaft of the renal flow device is equal to or less than about 1 French and about 4 French, and beneficially may be about 2 French; or the diameter of the second flow path of the renal flow assembly is at least about 3 mm to about 20 mm; or the delivery catheter has an outer diameter of at least about 4 French, generally between about 6 French and about 8 French.

In another type of embodiment, the delivery catheter is an angiographic catheter such that the selective renal flow delivery is done adjunctive to performing an upstream angiography procedure. In another such embodiment, the delivery catheter is a coronary guiding catheter with a proximal end portion, a distal end portion, and a guide catheter lumen extending between a proximal port along the proximal end portion and a distal port along the distal end portion. The distal end portion of the coronary guiding catheter is adapted to be positioned upstream across the location with the distal port located within a coronary artery. In a further variation according to this embodiment, the system further includes a coronary interventional catheter system that is adapted to be delivered through the guide catheter lumen to a site of coronary occlusion within the coronary artery.

According to another highly beneficial mode of the present and various other aspects elsewhere summarized herein, the renal flow assembly is adapted to substantially direct the volume of fluid or agent within an aorta to flow substantially into multiple renal arteries via their respective unique ostia.

In one particular beneficial embodiment of this mode, the renal flow assembly includes an expandable tubular member. The tubular member has a tubular wall that extends between a first and second end portions, and also has an interior passageway that extends between first and second open ends along the respective end portions. The expandable tubular member is adjustable between a radially collapsed condition and a radially expanded condition as follows. In the radially collapsed condition, the expandable tubular member has a collapsed outer diameter that is adapted to be delivered to the location through a delivery lumen of a delivery sheath. However, once delivered to the location, the expandable tubular member is expandable to the radially expanded condition with an expanded outer diameter that is greater than the collapsed outer diameter, and also with the first end portion located downstream from the multiple renal artery ostia and the second end located upstream from the multiple renal artery ostia. Also in the radially expanded condition, the tubular wall divides aortic blood flow at the location into an exterior flow path located within an exterior circumferential space between an outer circumferential surface of the tubular member and a wall of the aorta that includes the multiple renal artery ostia, and an interior flow path located within the interior passageway. The tubular member also directs the volume of fluid into the multiple renal arteries along the exterior flow path, and allows the substantial volume of aortic blood to flow downstream across the location along the second flow path within the interior passageway.

According to one variation of this embodiment, the tubular member in the radially expanded condition further comprises a frustroconical shape with a tapering outer diameter between end portion having varied outer diameters. One feature according to this variation provides the tubular member with a varied taper along its length between its end portions. According to another feature, the expandable tubular member further includes first and second radial support members each with a shape-retaining wire ring member and secured to the tubular member along its opposite ends. In the radially expanded condition, the first radial support member has a larger outer diameter than the second radial support member. The tubular member according to this feature also includes a sheet of substantially flexible material that extends between the first and second radial support members and forms at least in part the tubular wall of the expandable tubular member. According to still further features: the first and second radial support members may be formed from a nickel-titanium metal alloy; or the sheet forming the tubular wall may be constructed from a fluoropolymer material, such as a polytetrafluoroethylene (PTFE) material; or the radial support members may be connected by a spine member extending along the tubular wall, which spine member may be shaped to provide a stand-off adapted to space the tapered tubular wall away from the wall of the aorta at the location.

In still a further mode at least according to the present aspect, the system further includes a fluid agent delivery system cooperating with the renal flow assembly. More specifically, the fluid agent delivery assembly delivers a volume of fluid agent to a location within the aorta from a source externally of the patient, which location is positioned such that the fluid agent is substantially directed by the renal flow assembly to flow principally into the renal artery via its ostium.

Another aspect of the invention is a flow isolation assembly for dividing and substantially isolating first and second paths of blood flowing within a blood vessel in a patient. The assembly includes a delivery shaft, a tubular member, and at least one radial support member. The tubular member has a tubular wall formed by a sheet of substantially flexible material that is substantially impermeable to blood, and has an outer surface with an outer diameter, and also has an inner annular surface that defines an interior passageway. The interior passageway extends along an axis between opposite open ends along the tubular member. The radial support member is secured to the distal end portion of the delivery shaft, and has a ring-shaped support wire with a circumference. One end portion of the tubular member is secured substantially along the circumference of the ring-shaped support wire such that the tubular member extends along the axis from the radial support member to the other end portion.

According to this overall structure just described, the radial support member is also adjustable between a radially collapsed condition and a radially expanded condition relative to the axis as follows. In the radially collapsed condition the radial support member is relatively radially collapsed with respect to the axis such that the tubular member has collapsed outer and inner diameters that are sufficiently small so that the tubular member may be delivered to the location within the blood vessel through a radially confining delivery lumen of a delivery sheath with the first and second open end portions having respective downstream and upstream positions relative to blood flowing along the blood vessel. In the radially expanded condition at the location the radial support member is radially expanded relative to the axis such that the tubular member has expanded outer and inner diameters that are substantially larger than the collapsed outer and inner diameters, respectively, but wherein the outer diameter of the tubular member at least along the upstream end portion of the tubular member is less than an inner diameter of the blood vessel wall.

In addition, the tubular member in the radially expanded condition substantially prevents fluid communication through the tubular wall between an interior flow path along the interior passageway and an exterior flow path along a circumferential region of the blood vessel surrounding the outer surface of the tubular member and located between the outer surface of the tubular wall and the blood vessel wall at least along the upstream end portion of the tubular member.

In one mode of this aspect, the radial support member is located along the respective downstream end portion of the tubular member. In another mode, the radial support member is located along the respective upstream end portion of the tubular member.

In still another mode, the system further includes a second radial support member.

The tubular member is secured along one of its ends substantially to a first circumference of the first radial support member, and along its other end substantially to a second circumference of the second radial support member. When radially expanded, the tubular wall is supported by the opposite radial support members at the opposite respective ends, thus forming the tubular member with a shape that provides a first flow path through the interior passageway between the two opposite ends and across the location, and that also provides a second flow path that is substantially isolated from the first flow path in the exterior circumferential space surrounding the outer surface of the tubular member and between the outer surface and the body space wall.

In another mode, the adjustable ring-shaped support wire of the radial support member is constructed from a shape retaining material, such as a nickel-titanium alloy metal material.

According to another mode of the present aspect, a fluid agent delivery assembly cooperates with the tubular member and is adapted to deliver a volume of fluid agent primarily into the exterior flow path. The tubular member in the radially expanded condition at the location substantially prevents fluid communication with respect to the volume of fluid agent through the tubular wall and from the exterior flow path and into the interior flow path.

According to one embodiment of this mode, the fluid agent delivery assembly includes a delivery passageway extending between a distal port that is adapted to be positioned at an injection location within the blood vessel and a proximal port that is concurrently located externally of the patient's body where it is adapted to couple to a source of fluid agent. The delivery passageway is adapted to deliver the volume of fluid agent from the fluid agent source and through the distal port into the injection location within the blood vessel. According this embodiment in a further respect, the injection location is positioned to allow the volume of fluid agent to flow substantially along the exterior flow path and without substantial mixing of the fluid agent into the interior passageway of the tubular member along the location.

In one variation, the tubular wall further comprises a bladder along the upstream end portion that is defined at least in part by overlapping portions of the sheet of material and that defines a reservoir that is in fluid communication with and forms a portion of the delivery passageway. The distal port of the delivery passageway comprises an outer surface along the bladder that is permeable to the fluid agent and that is positioned to allow the fluid agent to flow from within the reservoir of the bladder, through the surface, and principally into the exterior flow path.

In various additional features applicable to this variation: the outer surface may include at least one aperture formed therethrough and through which the fluid agent is allowed to pass into the exterior flow path; or the sheet of material along the outer surface of the bladder may be sufficiently porous with respect to the fluid agent to allow flow therethrough into the exterior flow path.

In another applicable and beneficial feature, the bladder may be located around a circumference of the upstream end portion of the tubular member with the radial support member located within the reservoir formed by the bladder. The bladder may also be permeable to the fluid agent substantially around the circumference, such as by the bladder being permeable to the fluid agent continuously around the circumference, or by the bladder being permeable to the fluid agent at multiple discrete locations around the circumference.

In another mode of the present aspect, the sheet of material comprises a fluoropolymer material, such as a polytetrafluoroethylene (PTFE) material. One particular beneficial embodiment provides an expanded, or "ePTFE" material sheet.

According to yet another mode, in the radially expanded condition at the location the opposite ends of the tubular members corresponding to respective downstream and upstream positions have varied outer diameters, with the upstream outer diameter being less than the outer diameter at the downstream end and also less than the corresponding inner diameter of the blood vessel, such that the tubular member has a tapered shape with a reducing outer diameter from the first outer diameter to the second outer diameter.

According to one embodiment of this mode, the outer diameter of the downstream end portion of the tubular member is sufficient to substantially circumferentially engage the blood vessel wall of the blood vessel at the downstream position. For infrarenal aorta use, this is beneficially between about 20 mm and about 40 mm.

According to another embodiment, the opposite end portions of the tubular member corresponding to the respective downstream and upstream positions within the blood vessel are located proximally and distally, respectively, with respect to each other along the distal end portion of the delivery shaft.

Another aspect of the invention is a medical device system having a delivery shaft, a tubular member, a proximal radial support member secured to the distal end portion of the delivery shaft and also to a proximal end portion of the tubular member, and a distal radial support member secured to a distal end portion of the tubular member.

The tubular member has a tubular wall comprising a sheet of material formed into a tubular shape with an outer surface and an inner surface that defines an interior passageway extending along the axis between a proximal and distal open ends corresponding with proximal and distal end portions of the tubular member. Each of the proximal and distal radial support members includes a ring-shaped support wire that is secured substantially along a circumference of the respective proximal and distal end portions of the tubular member. The tubular member also has a distally tapered shape that tapers from a proximal outer diameter along the proximal end portion where secured to the proximal radial support member to a distal outer diameter that is less than the proximal outer diameter along the distal end portion of the tubular member where secured to the distal radial support member.

In one mode of this aspect, the distal radial support member is also secured to the distal end portion of the delivery shaft distally to the proximal radial support member.

In another mode, a longitudinal support member is also provided that extends along the axis and secured to the proximal and distal radial support members, respectively, and that also holds the respective radial support members at relatively fixed longitudinal positions relative to each other with respect to the longitudinal axis of the tubular member.

According to one embodiment of this mode, the longitudinal support member is a region of the distal end portion of the delivery shaft.

According to another embodiment, the longitudinal support member is the sole longitudinal support member secured to the tubular member and extends along the tubular wall of the tubular member relative to the longitudinal axis. The tubular member does not include other longitudinal or radial support members than the proximal and distal radial support members and the longitudinal support member, benefiting from simplicity of design and optimally low profiles for delivery and in-vivo use.

In another mode of the present aspect, each of the ring-shaped support wires of the proximal and distal radial support members, respectively, comprises a shape-retaining material, such as beneficially a nickel-titanium metal alloy material.

In one embodiment of this mode, each of the ring-shaped support wires is formed from an elongated wire having a length between two opposite ends and with an intermediate portion between the opposite ends that is ring-shaped, such that the two ends are positioned closely adjacent to each other. The two adjacently positioned ends are secured to a longitudinal support member or extending between the proximal and distal radial support members, or to the distal shaft, such as being secured within grooves, slots, or ports formed in the longitudinal support member or distal delivery shaft.

In another mode, the sheet of material forming the tubular member comprises a fluoropolymer material, such as a polytetrafluoroethylene (PTFE) material.

In another mode, the tubular member is adjustable between a radially collapsed condition and a radially expanded condition as follows. In the radially collapsed condition the tubular member has a respective collapsed outer diameter that is adapted to be delivered to a location within an aorta adjacent to at least one renal artery ostium in a patient with the proximal end portion of the tubular member positioned downstream from the ostium and the distal end portion of the tubular member positioned upstream from the tubular member. The tubular member is adjustable at the location to the radially expanded condition with a radially expanded outer diameter that is larger than the collapsed outer diameter, and such that tubular wall divides aortic flow along the location into exterior and interior blood streams that are substantially isolated from each other by the tubular wall along the location. The tubular wall in the radially expanded condition at the location directs the exterior blood stream along an exterior flow path within a circumferential area surrounding the tubular member and between the outer surface of the tubular member and the aortic wall into the renal artery ostium, and also allows the interior blood stream to flow along an interior flow path corresponding to the interior passageway and that perfuses downstream across the location.

According to one embodiment of this mode, a fluid agent delivery assembly cooperates with the tubular member and delivers a volume of fluid agent primarily into the exterior flow path. The tubular member in the radially expanded condition at the location substantially prevents fluid communication with respect to the volume of fluid agent through the tubular wall and from the exterior circumferential area and into the interior passageway.

In one variation of this embodiment, the fluid agent delivery assembly includes a delivery passageway extending between a proximal port located externally of the body of the patient and a distal port that is adapted to be positioned at an injection location within the blood vessel. The proximal port couples to a source of fluid agent, and the delivery passageway is adapted to deliver the volume of fluid agent from the fluid agent source and through the distal port into the injection location within the blood vessel. The injection location is positioned to allow the volume of fluid agent to flow substantially along the exterior flow path and without substantial mixing of the fluid agent into the interior passageway of the tubular member along the location.

Another aspect of the invention is a system for locally delivering a volume of a fluid agent to a desired location within a patient, and includes a delivery shaft and a tubular member secured to the distal end portion of the delivery shaft.

The tubular member has a proximal end portion, a distal end portion, and a tubular wall constructed from a sheet of material formed into a tubular shape with an outer surface and an inner surface that defines an interior passageway. The interior passageway extends between a proximal open end along the proximal end portion of the tubular member and a distal open end along the distal end portion of the tubular member. A bladder is located along the distal end portion of the tubular wall and defines a reservoir that is fluidly coupled to a fluid delivery passageway that is further coupled to a proximal port located along the proximal end portion of the delivery shaft and that is still further adapted to couple to a source of a fluid agent externally of the patient's body; and The bladder according to this aspect has an outer wall that is permeable to the fluid agent and is positioned to allow the fluid agent to flow from within the reservoir of the bladder, through the outer wall, and principally into an exterior circumferential area surrounding the outer surface of the tubular member.

In one mode of this aspect, the bladder is formed at least in part by overlapping portions of the sheet of material that forms the tubular wall of the tubular member.

In another mode, the outer wall of the bladder includes at least one aperture formed therethrough and through which the fluid agent is allowed to pass into the exterior circumferential area.

In yet another mode, the sheet of material along the outer wall of the bladder is sufficiently porous with respect to the fluid agent to allow flow therethrough into the exterior circumferential area.

In still a further mode, the bladder is located around a circumference of the distal end portion of the tubular member.

In various beneficial embodiments according to this mode: a radial support member is located within the circumferential bladder; or the bladder is permeable to the fluid agent at multiple locations around the circumference; or the bladder is permeable to the fluid agent continuously around the circumference.

According to another mode of the present aspect, the tubular member is adjustable between a radially collapsed condition and a radially expanded condition as follows. In the radially collapsed condition the tubular member has a respective collapsed outer diameter that is adapted to be delivered to a location within an aorta adjacent to at least one renal artery ostium in a patient with the proximal end portion of the tubular member positioned downstream from the ostium and the distal end portion of the tubular member positioned upstream from the tubular member. The tubular member is adjustable at the location to the radially expanded condition with a radially expanded outer diameter that is larger than the collapsed outer diameter, and such that tubular wall divides aortic flow along the location into first and second blood streams that are substantially isolated from each other by the tubular wall along the location. The tubular wall in the radially expanded condition at the location directs the first blood stream along an exterior flow path within the exterior circumferential area surrounding the tubular member and between the outer surface of the tubular member and the aortic wall, which exterior flow path is directed to flow primarily into the at least one renal artery ostium, and also allows the second blood stream to flow along an interior flow path corresponding to the interior passageway and that perfuses downstream across the location.

Another aspect of the invention is a renal flow system with a renal flow device having a delivery shaft and a renal flow assembly on the distal end portion distal end portion of the delivery shaft with an expandable tubular member, and also with a fluid agent delivery system cooperating with the renal flow assembly of the renal flow device. The tubular member is secured to the distal end portion of the delivery shaft and has a proximal end portion, a distal end portion, and a tubular body with an outer surface and an inner surface that defines an interior passageway extending between respective proximal and distal open ends located along the proximal and distal end portions of the tubular member, respectively.

The tubular member is adjustable between a radially collapsed condition and a radially expanded condition as follows. In the radially collapsed condition, the tubular member is adapted to be positioned at a location within an aorta of a patient adjacent to at least one renal artery ostium along the aorta and with the proximal end portion of the tubular member located downstream from the ostium and the distal end portion of the tubular member located upstream from the ostium. In the radially expanded condition at the location, the tubular member substantially divides aortic blood flow between an interior flow path within the interior passageway and an exterior flow path located within a exterior circumferential area surrounding the outer surface of the tubular member and between the outer surface and the wall of the aorta at the location. In the radially expanded condition the tubular member also directs the exterior flow path substantially into the renal artery via its ostium, and allows the aortic blood in the interior flow path to flow downstream past the location The fluid agent delivery assembly according to this aspect locally delivers a volume of fluid agent into the exterior flow path at a localized circumferential region around the circumference of the tubular member. However, the tubular member has a localized shape corresponding with the localized circumferential region around the tubular member and that forms a mixing region. This shape and resulting mixing region promotes substantial mixing of the fluid agent from the localized circumferential region and into blood flowing along other circumferential regions of the exterior flow path.

In one mode of this aspect, the tubular member in the radially expanded condition has a tapered tubular shape with a distally reducing tapered outer diameter from a first outer diameter along the proximal end portion to a second outer diameter along the distal end portion and that is less than the first outer diameter. The localized shape of the tubular member includes a localized region of relatively increased taper pitch corresponding to a more drastic reduction in the outer diameter of the tubular member over the length of the localized region. This area of relatively increased taper pitch further corresponds to an increased exterior space between the tubular member and the aortic wall along and distal to the localized region, which in turn allows for more efficient mixing of the fluid agent with blood flow within the exterior flow path around the tubular member.

According to one embodiment of this mode, the tapered shape along the localized region has a stepped increase in taper pitch going from the proximal end portion to the distal end portion of the tubular member.

In one variation of this embodiment, the tapered shape along the localized region has a stepped increase in taper pitch followed by a stepped decrease in taper pitch, both going from the proximal end portion to the distal end portion of the tubular member.

According to another mode, a longitudinal support member extends along and secured relative to the tubular wall of the tubular member along the localized circumferential region. The localized mixing region is formed at least in part by a corresponding localized shape of the longitudinal support member.

In one embodiment of this mode, the longitudinal support member further comprises an elongated tubular member with a distal fluid delivery lumen that communicates externally from the elongated tubular member through a distal port located along the localized circumferential region. The distal fluid delivery lumen is further coupled to a proximal port located externally of the body of the patient that is still further adapted to couple to the source of fluid agent. Accordingly, the longitudinal support member forms a distal portion of the fluid agent delivery assembly and is adapted to deliver the volume of fluid agent into the exterior flow path through the distal port.

In another highly beneficial mode, the tubular member directs the exterior flow path into multiple renal arteries via multiple respective ostia along the aorta wall, wherein each kidney is fed by at least one of the multiple renal arteries.

Another aspect of the invention is a renal flow system that includes a renal flow device with a delivery shaft and a renal flow assembly located along the distal end portion of the delivery shaft. The system according to this aspect also includes: means for dividing a cross-section of aortic blood flow at a location within an aorta adjacent to at least one renal artery ostium into an interior flow path flowing downstream across the location and an exterior flow path that substantially circumferentially surrounds the interior flow path; means for substantially directing the blood in the exterior flow path to flow substantially into the at least one renal artery ostium along the aorta at the location; means for allowing the blood in the interior flow path to flow substantially downstream from the location; means for substantially isolating the exterior and interior flow paths from each other along the location; means for locally delivering a volume of fluid agent substantially into a localized circumferential portion of the exterior flow path along the distal end portion of the tubular member; and means for mixing the volume of fluid agent that is delivered into the localized circumferential portion of the exterior flow path across a substantial circumferential portion of the exterior flow path circumferentially around the tubular member such that a substantial portion of the agent is delivered via the second flow path into each of the plurality of renal artery ostia.

According to one mode of this aspect, the means for dividing the aortic blood flow includes a tubular member that is adapted to be positioned within the aorta at the location.

According to another mode, the means for substantially directing the blood includes a tubular member with a tubular wall having an outer surface. The tubular member is adapted to be positioned within the aorta at the location with a shape such that: the exterior flow path is located between the outer surface of the tubular wall and a region of the aortic wall including the renal artery ostium at the location; the tubular wall substantially isolates blood in the exterior flow path from flowing across the location and escaping into downstream circulation from the location; and blood in the exterior flow path flows principally into the at least one renal artery via its ostium located along the exterior flow path.

According to still a further mode, the means for allowing the blood in the interior flow path to flow substantially downstream from the location includes a tubular member having first and second end portions and an interior passageway extending between a first open end along the first end portion of the tubular member and a second open end along the second end portion of the tubular member. The tubular member is adapted to be positioned within the aorta at the location with the first and second end portions on upstream and downstream sides of the at least one ostium, respectively. Accordingly, an inner flow component of aortic blood flowing into the location from an upstream location is allowed to enter the interior passageway through the first open end and is thereafter allowed to flow downstream across the location through the interior passageway.

According to yet another mode, the means for substantially isolating the interior and exterior flow paths respectively from each other along the location includes a tubular wall of a tubular member that is adapted to be positioned within the aorta at the location and that is substantially impermeable to blood. The tubular wall is thus located between the exterior flow path that is located within an exterior circumferential space surrounding the tubular member and between an outer surface of the tubular wall and the aortic wall, and the interior flow path that is located within an interior passageway defined at least in part by an inner surface of the tubular wall.

According to still another mode, the means for locally delivering a volume of fluid agent substantially into a localized circumferential portion of the exterior flow path along the distal end portion of the tubular member includes a fluid delivery assembly having a fluid passageway extending between a proximal port and a distal port. The distal port is adapted to be positioned within the aorta along the localized circumferential portion of the exterior flow path and with the proximal port located externally of the body of the patient, and the proximal port is adapted to couple to a source of the fluid agent. Accordingly, the volume of fluid agent is delivered into the localized circumferential portion of the exterior flow path through the distal port via the fluid passageway and proximal port coupled to the source.

In another mode, the means for mixing the volume of fluid agent across a substantial circumferential portion of the exterior flow path circumferentially around the tubular member includes a tubular member that is adapted to be positioned at the location with a proximal end portion of the tubular member located downstream from the ostia and a distal portion of the tubular member located upstream from the ostia. The tubular member is shaped such that the exterior flow path flows externally around the tubular member and between an outer surface of a tubular wall of the tubular member and the aortic wall. In addition, the tubular member further has a localized shape corresponding with the localized circumferential portion of the exterior flow path that forms a localized mixing region of locally increased space between the tubular wall and the aortic wall. The locally increased space is adapted to increase mixing of the fluid agent with blood flowing substantially around the tubular member in the exterior flow path.

Other aspects of the invention include various methods corresponding to treating patients, including without limitation various modes related to intended uses of other aspects of the invention such as those summarized immediately above and elsewhere throughout this disclosure, including in particular the following.

One such aspect of the invention is a method for providing localized medical care to a renal system in a patient. This method includes: positioning a renal flow assembly at a location within the patient's aorta that is adjacent to an ostium of at least one renal artery extending from the aorta; using the renal flow assembly from the location within the aorta, directing a volume of fluid within the aorta to be substantially locally delivered into the at least one renal artery via its ostium; and while locally delivering the volume of fluid substantially into the at least one renal artery from the location, allowing a substantial volume of aortic blood to flow downstream past the location and into the patient's circulation downstream from the renal artery ostium.

One further mode of this aspect further includes, while performing the other steps above, substantially isolating the volume of fluid being directed into the at least one renal artery from mixing with the substantial volume of aortic blood flowing downstream from the location.

Another mode includes conducting an interventional medical procedure at least in part at an upstream location upstream from the location while locally directing the volume of fluid into the at least one renal artery. This mode may also beneficially be performed while also performing one or both of: allowing the substantial volume of aortic blood to flow downstream from the ostium; or while substantially isolating the volume of fluid from mixing with the volume of aortic blood flowing downstream.

According to another mode, the volume of fluid is an outer blood flow component of aortic blood, and the method further includes passively directing the outer blood flow component into the at least one renal artery at an increased pressure at the respective ostium that is artificially elevated by the catheter to be greater than a normal physiologic pressure at the ostium for that patient.

One further embodiment of this mode further includes preventing a portion of the outer blood flow component from passively flowing downstream across the location and past the renal artery ostium, in addition to passively directing the portion of outer aortic blood flow component toward the at least one renal artery ostium using the distal end portion of the catheter.

In another mode, the volume of fluid is a fluid agent, and the method further includes: while the renal flow assembly is at the location within the aorta, delivering a volume of the fluid agent to the location within the aorta; and directing the volume of fluid agent to flow from the location within the aorta and substantially into the at least one renal artery via its ostium.

One embodiment of this mode includes providing the renal flow assembly on the distal end portion of a catheter; providing a fluid delivery lumen in the catheter with a proximal port at a proximal end portion of a catheter in fluid communication with a source of the fluid agent externally of the patient while a distal port on the distal end portion of the catheter is positioned at the location; and delivering the volume of fluid agent into the outer blood flow component via the fluid delivery lumen.

In another mode, the interventional medical procedure includes injecting a radiopaque contrast agent into the patient's arterial system at a location that is upstream from the renal ostium.

One embodiment of this mode further includes providing the volume of fluid being directed into the renal artery with an agent that is adapted to treat or protect the patient's renal system with respect to the radiopaque contrast agent being injected at the upstream location.

Still another mode of this aspect further includes providing the volume of fluid being locally directed into the least one renal artery with an agent comprising at least one of a vasodilator, an antioxidant, or a diuretic agent, or combinations or blends thereof.

In one embodiment of this mode, the agent comprises a vasodilator. In further beneficial variations, the vasodilator comprises at least one of papavarine, fenoldopam, calcium channel blockers, atrial natriuretic peptide (ANP), acetylcholine, nifedipine, nitroglycerine, nitroprusside, adenosine, dopamine, or theophylline, or combinations or blends thereof. In another embodiment, the agent comprises an antioxidant agent. In further beneficial variations of this embodiment, the antioxidant agent comprises acetylcysteine. In another embodiment, the agent comprises a diuretic agent. In further beneficial variations of this embodiment, the diuretic agent comprises at least one of mannitol or furosemide, or combinations or blends thereof.

Another mode includes positioning a delivery device at least in part within the patient's aorta at an upstream location that is upstream from the renal artery ostium.

In various further embodiments of this mode: the delivery device is an angiographic catheter; or the delivery device is a guiding catheter; or the delivery device is positioned at least in part within a coronary artery ostium; or the delivery device is positioned at least in part within a carotid artery ostium.

According to another mode, the method further includes locally directing the volume of fluid into multiple renal arteries via multiple respective ostia that are located at unique, relatively spaced positions along the aorta, and wherein each kidney is perfused by at least a respective one of the multiple renal arteries.

One highly beneficial embodiment of this mode further includes mixing the volume of fluid agent in an outer, circumferential region of the aortic blood flowing along the location adjacent the wall of the aorta and while substantially isolating the volume of agent from mixing with an inner region of aortic blood flowing downstream past the location and that is substantially surrounded by the outer, circumferential region. This embodiment may further include directing the aortic blood and mixed agent in the outer, circumferential region to principally flow into the multiple renal arteries via their respective ostia.

Another mode also includes: positioning a tubular member with a distal end portion of the tubular member located upstream from the location of the ostia and a proximal end portion of the tubular member located downstream from the location; with the proximal and distal end portions at the downstream and upstream locations, respectively, providing the tubular member with a distally reducing tapered shape such that the proximal end portion has a first outer diameter that is sufficient to substantially circumferentially engage the aorta wall at the downstream location, and further such that the distal end portion has a second outer diameter that is sufficiently less than the inner diameter of the aorta wall at the upstream location; and wherein the outer, circumferential region of aortic blood is located between an outer surface of the tubular member and the aortic wall between the distal tip of the distal end portion and the ostia.

A beneficial embodiment of this mode includes delivering the volume of fluid agent into the outer, circumferential region of blood flow at a first isolated radial position; and providing the shape of the tubular member with a mixing region having a different taper than other regions of the tubular member and that is associated with the first isolated circumferential position, using the mixing region to enhance the mixing of the agent with blood circumferentially around the tubular member to thereby more evenly distribute the agent to renal arteries having respective ostia at respectively unique circumferential locations around the aorta at the location.

According to another mode, the volume of aortic blood is allowed to flow passively downstream across the location during the delivery of the agent into the at least one renal artery.

Another aspect of the invention is a method for directing fluid to a renal system in a patient that includes: locally delivering a volume of fluid to at least one renal artery in the patient; and while locally delivering the volume of fluid to the at least one renal artery, positioning a medical device within an aorta of the patient upstream from an ostium of the at least one renal artery along the aorta of the patient.

Still another aspect of the invention is a renal flow device that is adapted to divide aortic flow into a first flow path and a second flow path, and to direct a volume of fluid in the first flow path into the renal artery ostia while allowing the second flow path to flow downstream past the ostia. The device is adapted to provide such localized fluid delivery into the renal system over a wide range of aorta diameters.

In one mode of this aspect, the device includes a tubular member with a proximal end portion that has a variable outer diameter and is adapted to substantially circumferentially engage a wall of an aorta downstream from the ostia over that range.

In one embodiment, the proximal end portion includes a radial support member with a ring-shaped wire support that is adapted to adjust its plane relative to the longitudinal axis of the tubular member, thereby ovalizing along its plane of curvature but while maintaining a shape relative to the orthogonal plane to the long axis that circumferentially engages a wide range of vessel walls.

In another embodiment, the radial support member along the proximal end has a ring shape in a first transverse plane to the long axis of the tubular member, but also has a second shape orthogonal to that plane, such as a sinusoidal or serpentine shape. This allows varied circumferences in the orthogonal plane to the long axis, though over a constant true circumference of the serpentine or sinusoidal support ring that stretches the distance between peaks, and reduces their relative amplitude, during expansion.

The invention according to another aspect is a method that locally delivers a drug to at least one renal artery from a location within an aorta in a patient adjunctive to in order to treat or prevent RCN. In one particular mode, the method is prophylactic. In one embodiment of this mode, the method includes first identifying a patient as being in a particular risk group for developing RCN, and then locally delivering the drug contemporaneous with radiocontrast delivery in the patient prophylactically before observing a symptom for RCN. Another embodiment includes delivering the protective drug during radiocontrast delivery in the patient.

Further modes of this aspect include delivering at least one of a vasodilator, antioxidant, or diuretic agent, or combination or blend thereof.

In one embodiment of this mode, the agent comprises a vasodilator. In further beneficial variations, the vasodilator comprises at least one of papavarine, fenoldopam, calcium channel blockers, atrial natriuretic peptide (ANP), acetylcholine, nifedipine, nitroglycerine, nitroprusside, adenosine, dopamine, or theophylline, or combinations or blends thereof. In another embodiment, the agent comprises an antioxidant agent. In further beneficial variations of this embodiment, the antioxidant agent comprises acetylcysteine. In another embodiment, the agent comprises a diuretic agent. In further beneficial variations of this embodiment, the diuretic agent comprises at least one of mannitol or furosemide, or combinations or blends thereof.

Another aspect of the invention is a method that includes delivering a renal flow assembly and an interventional catheter device for use across the renal flow assembly through a common delivery catheter. In one particular mode, the method includes delivering a guide catheter through the common delivery catheter while the renal flow assembly is located within the delivery catheter and extending therefrom into a location within an aorta adjacent renal artery ostia; and, delivering the guide catheter further distally across the location where the renal flow assembly is positioned and while directing a volume of fluid into a renal artery with the renal flow assembly. In a further embodiment, the method also includes simultaneously allowing a substantial volume of aortic blood to flow downstream across the location sufficient to prevent substantial ischemia. The method may further include delivering a volume of radiocontrast dye from the interventional catheter. A further variation includes delivering the radiocontrast dye into at least one coronary artery.

BRIEF DESCRIPTION OF THE DRAWINGS

The invention will be more fully understood by reference to the following drawings which are for illustrative purposes only:

FIG. 1 is an elevational view, partially in section, of a catheter that embodies features of the invention, illustrating the expandable tubular member and balloon in an unexpanded configuration.

FIG. 2 is an enlarged view, partially in phantom, of a distal section of the catheter shown in FIG. 1, with the tubular member in the expanded configuration.

FIG. 18 is an elevational view of a catheter assembly made in accordance with another embodiment of the present invention.

FIG. 19 is an elevational view similar to FIG. 18 further illustrating the placement of a guiding catheter.

FIG. 20 is an elevational view, partially broken away, illustrating further details of a balloon used in certain embodiments of the present invention.

FIG. 20A is a close up view of certain details of FIG. 20.

FIG. 21 is a cross-section of the assembly taken at line 21—21 of FIG. 20.

FIG. 22 is an elevational view, partially broken away, illustrating further details of a proximal sheath sidearm used in certain embodiments of the present invention.

FIG. 28 is an exploded view of the distal end portion of the renal flow device shown in FIG. 27, and shows various details of the renal flow assembly in relation to its attachment to the shaft of the device.

FIG. 29A shows a transverse cross-section taken along lines A—A in FIGS. 27 and 28.

FIG. 29B shows a transverse cross-section taken along lines B—B in FIGS. 27 and 28.

FIG. 29C shows a transverse cross-section taken along lines C—C in FIGS. 27 and 28.

FIG. 29D shows a transverse cross-section taken along lines D—D in FIGS. 27 and 28.

FIG. 32 shows an elevational view of a further embodiment for a renal flow system according to the invention that includes a similar renal flow device to that shown in FIG. 31.

FIG. 32A shows a partially segmented elevational view of various further interrelated components that are adapted for cooperative use within the system shown in FIG. 32.

FIG. 33 shows an elevational view of another embodiment for a renal flow system of the invention.

FIG. 37 shows an exploded view of another renal flow assembly embodiment of the invention.

FIG. 38A shows a transverse cross-sectional view taken along lines A—A in FIG. 37.

FIG. 38B shows an exploded view of the region designated B in FIG. 37 and shows certain details of the distal end of the renal flow assembly shown in FIG. 37.

DETAILED DESCRIPTION OF THE INVENTION

Figure 3:
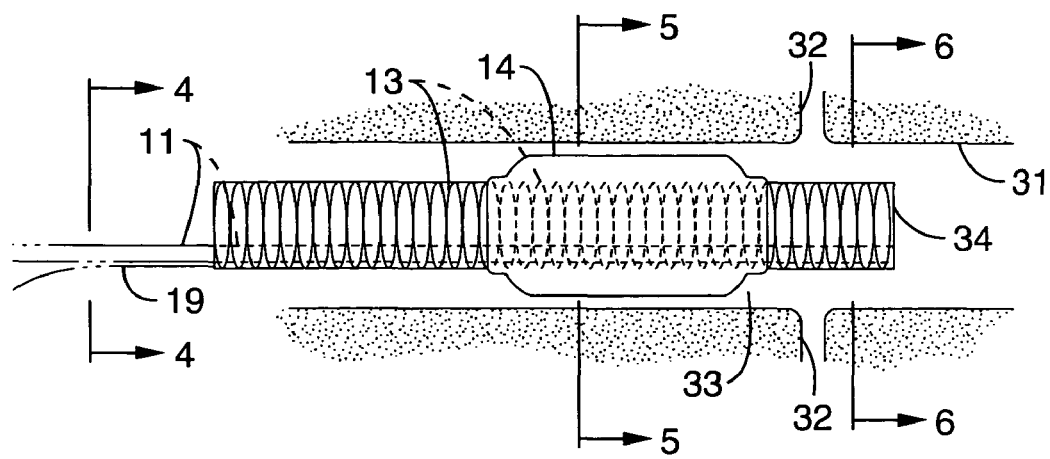
FIG. 3 is an enlarged view, partially in phantom, of a distal section of the catheter shown in FIG. 2, illustrating the catheter in the patient's descending aorta proximate the renal arteries, with the balloon in the inflated configuration.

As will be appreciated by reference to the detailed description below and in further respect to the Figures, the present invention is principally related to selective renal flow systems and methods, which are thus related to similar subject matter disclosed in the following prior filed, co-pending U.S. patent applications that are commonly owned with the present application: Ser. No. 09/229,390 to Keren et al., filed Jan. 11, 1999; Ser. No. 09/562,493 to Keren et al., filed May 1, 2000; and Ser. No. 09/724,691 to Kesten et al., filed Nov. 28, 2000. The disclosures of these prior patent applications are herein incorporated in their entirety by reference thereto.

The invention is also related to similar subject matter disclosed in other Published International Patent Applications as follows: WO 00/41612 to Libra Medical Systems, published Jul. 20, 2000; and WO 01/83016 to Libra Medical Systems, published Nov. 8, 2001. The disclosures of these Published International Patent Applications are also herein incorporated in their entirety by reference thereto.

The description herein provided relates to various beneficial features of certain medical device systems and methods in the context of their relationship in use within a patient's anatomy. Accordingly, for the purpose of providing a clear understanding, the term proximal should be understood to mean locations on the catheter relatively closer to the operator during use of the catheter, and the term distal should be understood to mean locations on the catheter relatively further away from the operator during use of the catheter. The term up-stream should be understood to mean locations on the catheter relatively further upstream in the blood flow within the blood vessel, when the catheter is in place in the patient's blood vessel. The term down-stream should be understood to mean locations on the catheter relatively further down-stream in the blood flow within the blood vessel, when the catheter is in place in the patient's blood vessel. In addition, various places in this disclosure refer to "substantial" delivery of fluids or agents into branch arteries from a main artery (e.g. into renal arteries from an aorta). In this context, the term "substantial" is intended to mean at least a majority (or over 50%) of the fluid being delivered, and may be in some circumstances as much as 75%, and most beneficially is at least about 90% of the fluid or agent. Where elsewhere used, the term is to be considered in the overall context of the intended use within the medical context of the present embodiments. For example, where "substantial" aortic perfusion or flow is described, it is intended to mean sufficient to prevent harmful downstream ischemia—enough of the flow is allowed to pass in order to substantially protect the patient's lower abdominal aortic perfusion during the operation. The various embodiments below provide further guidance as to the context of such descriptions.

It is to be further appreciated that the various embodiments herein described are beneficially intended in one regard to provide systems, assemblies, and/or methods ultimately used for delivering fluids specifically into renal arteries, such as in particular from a location within an aorta adjacent the renal ostia, and specific reference to such "renal flow", devices, catheters or the like is variously made throughout this disclosure. However, it is to be further appreciated that other uses or adaptations may be made for other environments of use. For example, the devices may be used to feed other branch arteries from a main artery. Moreover, certain of the disclosures provide solutions to improve certain aspects of specified assembly components—such inventive embodiments may be useful in relation to other components used in other assemblies and for other applications, even completely removed from local fluid delivery in medicine.

Where certain materials or constructions or modes of manufacture or use are described, they are intended to be exemplary and not limiting unless specifically identified to be so, even where identified as highly beneficial and even perhaps as an origin of novelty for the particular disclosure.

In addition, various of the embodiments are illustrated as catheter implementations, and are further illustrated during in-vivo use. Other techniques for placing the required flow assemblies described may be used where appropriate, such as transthoracic or surgical placement that either use or don't use percutaneous translumenal catheter techniques. In addition, reference to the illustrative catheter embodiments thus portray specific proximal-distal relationships between the intercooperating components of a renal flow device in relation to blood flow and their relative orientations on a delivery catheter platform. For example, some embodiments illustrate or are otherwise described by reference to retrograde femoral approach to renal delivery, such that the distal end of the catheter including the renal flow assembly is located upstream form the proximal end of the catheter. Other embodiments may show an opposite relative positioning, such as via an antegrade delivery to the site of renal arteries, e.g. from a brachial or radial arterial access procedure. However, it is to be further understood that such embodiments, though shown or described in relation to one such mode, may be appropriately modified by one of ordinary skill for use in the other orientation approach without departing from the intended scope.

Where considered illustrative to a thorough understanding of the embodiments or otherwise relevant, specific dimensions or ranges, materials, or modes or methods of construction or inter-cooperation between elements are described. While such specific parameters may be highly beneficial, in particular for certain indications or applications, they are not intended to be limiting and other substitutes may be made according to one of ordinary skill without departing from the scope of the invention.

Reference is often made herein to a "system" for performing a particular function, such as a renal flow system" for locally delivering fluids into renal arteries. Whereas such systems may beneficially use combinations of many different components as herein described, mere reference to the term "system" is not intended to require all such components, and therefore such references to "system" contemplate only one such disclosed component—the system merely grows as inter-cooperating elements or components are combined.

FIG. 1 illustrates a catheter 10, which embodies features of the invention, generally comprising an elongated shaft 11 having a proximal end, a distal end, and at least one lumen 12 extending therein, a tubular member 13 on a distal section of the catheter shaft 11 and a radially expandable member 14 on the tubular member 13. Adapter 15 on the proximal end of the shaft provides access to the catheter lumen. FIG. 1 illustrates the tubular member and the radially expandable member in low profile, unexpanded configurations for entry into the patient's blood vessel.

In the embodiment illustrated in FIG. 1, the radially expandable member 14 comprises an inflatable balloon. The balloon has proximal and distal ends secured to an outer surface of the tubular member 13, and an interior in fluid communication with an inflation lumen 21 (FIG. 4) in the shaft 11. The balloon 14 can be formed of a variety of suitable materials typically used in the construction of catheter occlusion balloons, and in a presently preferred embodiment is highly compliant and is formed of a material such as latex, polyisoprene, polyurethane, a thermoplastic elastomer such as C-Flex. In alternative embodiment, the balloon may be noncompliant or semi-compliant. While discussed below primarily in terms of a radially expandable member comprising a balloon, it should be understood that the radially expandable member might have a variety of suitable configurations.

In the embodiment illustrated in FIG. 1, the tubular member 13 comprises braided filaments 16, such as wire, ribbon, and the like, having a sheath 17, and having a lumen or interior passageway 18 therein. A pull line 19 having a distal portion secured to the tubular member is configured to be retracted or pulled proximally to radially expand the tubular member 13. Specifically, the braided filaments 16 can reorient from a longer, smaller diameter configuration and a shorter, larger diameter configuration cause the tubular member to shorten, thereby radially expanding the tubular member 13. When the pull line is not under tension, the spring force of the elastomeric material of the sheath 17 will cause the tubular body defined by the braided filaments 16 to elongate and reduce in diameter. The sheath 17 is preferably an elastomeric polymer on the braided filaments. The sheath 17 can be on an inner or outer surface of the braided filaments, or the braided filaments can be completely or partially embedded within the sheath 17. In the embodiment in which the sheath is on a surface of the filaments, the sheath is preferably secured to a surface of the filaments as for example with adhesive or heat bonding. The braided filaments 16 can be formed of a variety of suitable materials such as metals or stiff polymers. A variety of suitable polymeric materials can be used to form the sheath 17. While discussed below primarily in terms of a tubular member comprising a braided tube, it should be understood that the tubular member may have a variety of suitable configurations.

FIG. 2 illustrates the tubular member 13 in the expanded configuration after retraction of the pull line 19. As best illustrated in FIG. 2, showing the distal section of the shaft 11 within the inner lumen of the tubular member 13 in dotted phantom lines, the distal end of the shaft 11 is located proximal to the distal end of the expanded tubular member 13. In the embodiment illustrated in FIG. 2, the balloon 14 is in a non-expanded configuration. The section of the tubular member under the balloon is illustrated in dashed phantom lines.

Figure 4:
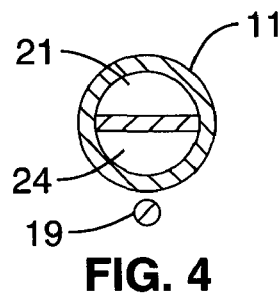
FIG. 4 is a transverse cross sectional view of the balloon shown in FIG. 3, taken along line 4—4.
Figure 5:
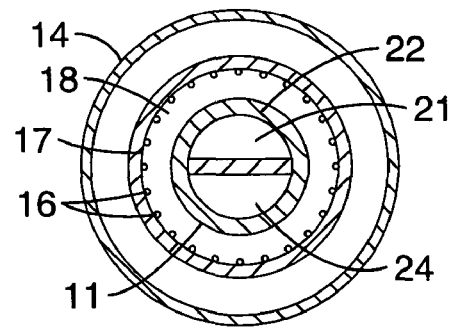
FIG. 5 is a transverse cross sectional view of the balloon shown in FIG. 3, taken along line 5—5.
Figure 6:
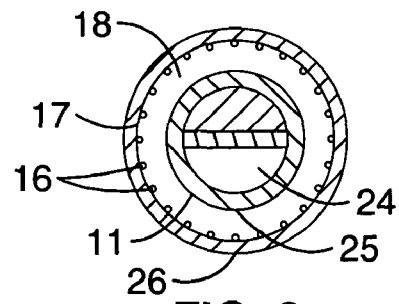
FIG. 6 is a transverse cross sectional view of the balloon shown in FIG. 3, taken along line 6—6.

FIG. 3 illustrates the catheter 10 with the balloon 14 in the expanded configuration. As best illustrated in FIGS. 4–6 showing transverse cross sections of the catheter shown in FIG. 3, taken along lines 4—4, 5—5, and 6—6, respectively, the shaft has an inflation lumen 21 extending from the proximal end of the shaft 11 to an inflation port 22 (FIG. 5) located on the shaft distal section, in fluid communication with the interior of the balloon. Arm 23 on adapter 15 provides access to the inflation lumen 21, and is in fluid communication with a source of inflation fluid (not shown). The shaft also has an agent delivery lumen 24 extending from the proximal end to an agent delivery port 25 in the distal end of the shaft 11. Arm 26 on adapter 15 provides access to the agent delivery lumen 24, and is in fluid communication with an agent source (not shown). The tubular member sheath 17 has an agent delivery opening 26 adjacent to the shaft agent delivery port 25, for providing a pathway for agent delivery from the lumen 24 to exterior to the tubular member 13. In the illustrated embodiment, the inflation lumen 21 and agent delivery lumen 24 are side-by-side in a multi-lumen shaft 11, with inflation port 22 extending through a sidewall of the shaft. However, a variety of suitable configurations may be used as are conventionally used in catheter shaft design including coaxial lumens in fluid communication with side ports or ports in the distal extremity of the shaft. The agent delivery port 25 is preferably in a sidewall of the shaft 11 distal section in fluid communication with the agent delivery lumen 24, however; alternatively, the agent delivery port 25 may be in the distal end of the shaft 11.

FIG. 3 illustrates the catheter 10 in a blood vessel 31, such as a descending aorta, of a patient, having branch vessels 32, such as the renal arteries, opening therein. The catheter 10 is introduced and advanced within the patient's blood vessel 31 in the low profile, unexpanded configuration illustrated in FIG. 1. The agent delivery port 25 is positioned proximate to (up-stream or in line with) the one or more branch vessels 32, and the distal end of the tubular member is preferably up-stream of the one or more branch vessels 32. The tubular member is then expanded to the expanded configuration, and, preferably, thereafter the balloon 14 is radially expanded by directing inflation fluid into the balloon interior. Specifically, in one embodiment of a method of the invention for delivery of a therapeutic or diagnostic agent to one or more of a patient's kidneys, the catheter is introduced into the femoral artery, as for example by the Seldinger technique, preferably slidingly over a guidewire (not shown), and advanced into the descending aorta 31. Although not illustrated, the shaft may be provided with a separate guidewire lumen, or the catheter may be advanced over a guidewire in agent delivery lumen 24 adapted to slidingly receive a guidewire. Alternatively, the catheter 10 may be advanced without the use of a guidewire. The agent delivery port 25 is positioned proximate to one or both renal arteries 32, as illustrated in FIG. 3, and the tubular member 13 extends within the aorta 31 up-stream and down-stream of the renal arteries 32. The tubular member 13 is radially expanded by retracting pull line 19. The interior passageway 18 of the tubular member 13 separates blood flow through the blood vessel 31 into an outer blood flow stream 33 exterior to the tubular member 13, and in inner blood flow stream 34 within the interior passageway 18 of the tubular member 13. The balloon 14 is expanded by directing inflation fluid into the inflation lumen. In the embodiment illustrated in FIG. 3, the balloon 14 is expanded to an outer diameter that does not completely occlude the patient's aorta 31. However, in an alternative embodiment, the balloon expands into contact with the wall of the aorta 21, to an outer diameter that completely occludes the aorta 31 (not shown). Balloon 14 may have a length and elongated configuration configured to provide mechanical stability for and coaxial centering of the operative distal section of the catheter in the blood vessel 31. A stabilizing member (not shown) may be provided on an outer surface of the distal end of the tubular member 13, such as for example unfoldable arms, which anchor the distal end of the catheter in the aorta 31 during delivery of agent. A variety of suitable imaging modalities may be used to position the catheter in the desired location in the blood vessel, such as fluoroscopy, or ultrasound. For example, radiopaque markers (not shown) on the shaft may be used in positioning the radially expandable member 14 and agent delivery port 25 at the desired location in the blood vessel 31.

A therapeutic or diagnostic agent (hereafter "agent") is delivered to the renal arteries 32 by introducing the agent into the agent delivery lumen 24 in the shaft 11, and out the agent delivery port 25. An agent delivery opening 26 in the tubular member 13 adjacent to the agent delivery port 25 provides a pathway for agent delivery from lumen 24 to external to the tubular member 13. The agent delivery port 25 is up-steam of the renal arteries 32 and proximal to the distal end of the tubular member 13. Thus, the outer blood flow stream 33 has a relatively high concentration of agent and the inner blood flow stream 34 has a relatively low concentration or no agent. Additionally, the balloon 14 in the expanded configuration restricts the flow of blood to decrease the blood flow exterior to the proximal portion of the tubular member 13 down-stream of the renal arteries 32 in comparison to the blood flow stream exterior to the distal portion of the tubular member 13 up-stream of the renal arteries 32. As a result, a relatively large amount of the agent delivered from the agent delivery port 25 is directed into the renal arteries 32, in comparison to the amount of agent that flows down-stream of the renal arteries 32 in the aorta 31.

In one embodiment, the outer blood flow stream is substantial. Preferably, the cross-sectional area of the inner lumen 18 of the tubular member 13 is about 4% to about 64% of the blood vessel 31 (i.e., aorta) cross-sectional area, or about 4 mm to about 16 mm for a blood vessel 31 having a 20 mm inner diameter. It should be noted that in some embodiments, the cross-sectional area of the wall of the tubular member 13 is not insignificant in relation to the cross-sectional area of the blood vessel 31. In the embodiment illustrated in FIG. 1 in which tubular member 13 comprises sheath 17 on a frame of filaments 16, this cross-sectional area is negligible. In alternative embodiments discussed below, such as the embodiments illustrated in FIGS. 10 and 13, the cross-sectional area of the wall of the tubular member 13 may be about 2% to about 50%, more specifically about 5% to about 20%, of the cross-sectional area of a section of the blood vessel 31 located at the up-stream most end of the catheter 10. Additionally, the aorta has multiple branch vessels in addition to the renal arteries that affect the total flow in the aorta at a given location therein. Thus, a percentage of the blood flow that enters the abdominal aorta, i.e., past the diaphragm, is delivered in the normal rest state of circulation to the celiac trunk, the superior and inferior mesenteric arteries, and the renal arteries. Nonetheless, the flow segmentation created by the presence of the deployed catheter 10 is such that the blood flow in the outer blood flow stream of a patient at rest is about 10% to about 90% of the total blood flow immediately up-stream of the up-stream or distal most end of the tubular member 13, i.e., of the total blood flow present in the section of the aorta immediately adjacent to the renal arteries. Similarly, the blood flow in the inner blood flow stream of a patient at rest is about 10% to about 90% of the total blood flow immediately up-stream of the up-stream or distal most end of the tubular member 13. The flow in the outer blood flow stream is sufficient to provide adequate kidney function, although the flow required will vary depending upon factors such as the presence of drugs which increase flow or increase the ability of the tissue to withstand ischemic conditions.

While the renal arteries are illustrated directly across from one another in FIG. 3, and the method is discussed primarily in terms of delivery of agent to both renal arteries together, it should be understood that the catheter may be positioned and used to deliver agent to the renal arteries individually, and specifically in anatomies having the renal arteries longitudinally displaced from one another. The flow of agent is then stopped. The tubular member 13 is contracted by urging the pull line distally, and the balloon 14 is collapsed by removal of the inflation fluid, and the catheter removed from the patient.

Figure 7:
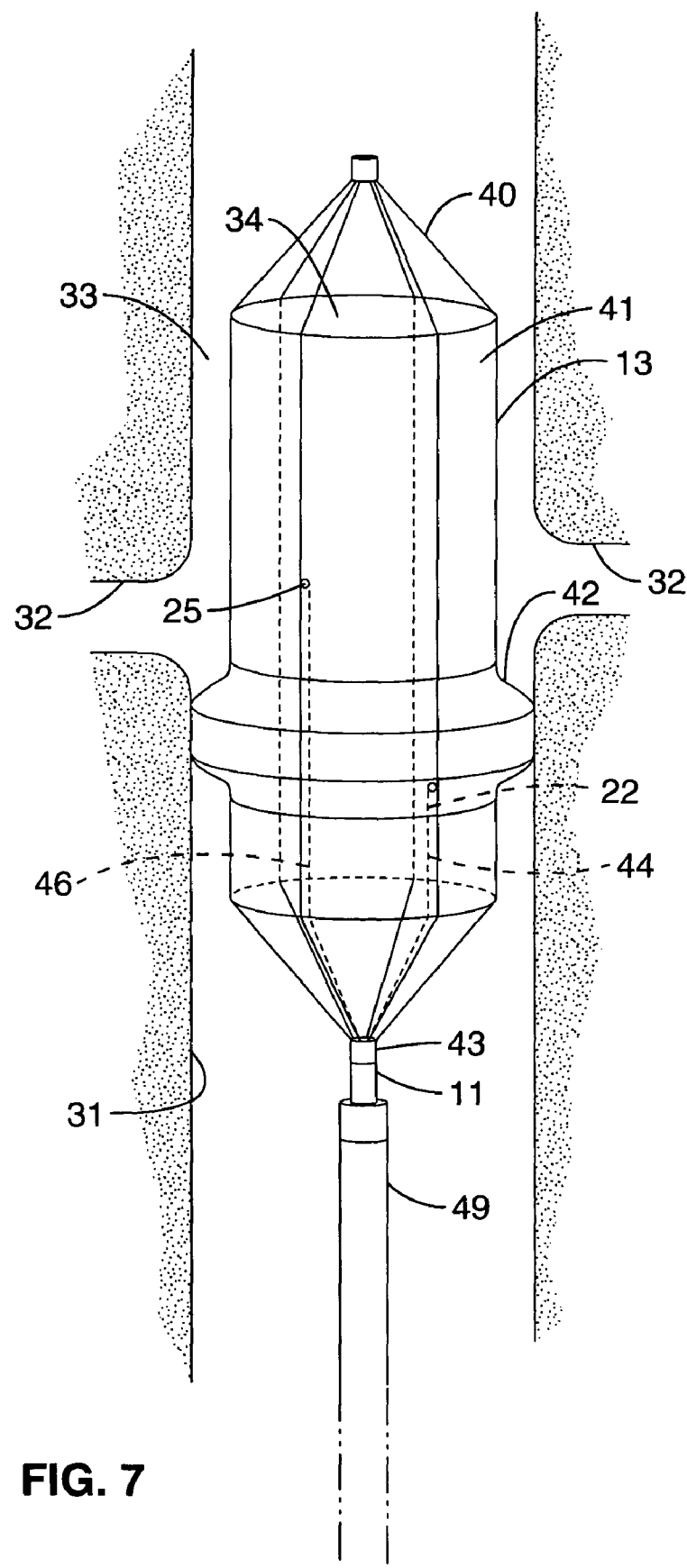
FIG. 7 is an enlarged view, partially in phantom, of a distal section of an alternative embodiment having an expandable tubular member comprising a sheath covered collapsible frame.

A variety of suitable radially expandable tubular members 13 may be used in the catheter 10 of the invention. FIG. 7 illustrates an alternative embodiment of distal end of the catheter 10 in which the tubular member 13 comprises a self-expanding frame 40 having a sheath 41 thereon. As discussed above in relation to the embodiment of FIG. 1, catheter shaft 11 defines an inflation lumen and an agent delivery lumen, and radially expandable member comprises a balloon 42 on an outer surface of sheath 41. For ease of illustration, the balloon 42 is shown as a transparent material. In the embodiment illustrated in FIG. 7, catheter shaft 11 comprises a multi-lumen proximal shaft 43 defining proximal sections of the inflation lumen 21 and agent delivery lumen 24, a first distal tubular member 44 defining a distal section of inflation lumen 21 extending to inflation port 22, and a second distal tubular member 46 defining a distal section of agent delivery lumen 24 extending to agent delivery port 25. First tubular member 44 extends distally from the distal end of the proximal section of the inflation lumen in the multi-lumen proximal shaft. Similarly, second tubular member 46 extends distally from the distal end of the proximal section of the agent delivery lumen in the multi-lumen proximal shaft. First and second tubular members 44/46 are typically formed of thin-walled polymeric material such as polyimide, with an inner diameter of about 0.002 inch to about 0.006 inch, and a wall thickness of about 0.0005 inch and about 0.002 inch. In alternative embodiments, catheter shaft comprises an outer tubular member with first and second inner tubular members defining inflation lumen and agent delivery lumen, respectively, extending within the outer member and out the distal end thereof. The agent delivery lumen 24 extends to a location proximal to the distal end of the tubular member 13 and distal to the balloon. One or more agent delivery ports 25 are provided in a distal section of the agent delivery lumens, as discussed above in relation to the embodiment of FIG. 1. In alternative embodiments, one or more additional agent delivery lumens may be provided.

In the illustrated embodiment, the frame 40 comprises longitudinally extending filaments or struts, such as wires, joined together at the proximal and distal ends thereof. In a preferred embodiment, frame 40 is formed of high strength metal, such as stainless steel, nickel-titanium alloy, and titanium. However a variety of suitable materials can be used including rigid polymers. The filaments typically have a round transverse cross section, with a diameter of about 0.006 inch to about 0.016 inch, or a rectangular transverse cross section with a thickness of about 0.001 inch to about 0.006 inch and a width of about 0.006 inch to about 0.016 inch. Sheath 41 is similar to sheath 17 discussed in relation to the embodiment of FIG. 1, and is preferably a thin walled elastomeric tubular member. The tubular member 13 is illustrated in FIG. 7 in the expanded configuration. The frame 40 is radially collapsible to a low profile configuration with the sheath 41 in a folded or pleated compact configuration for advancement within the patient's blood vessel. Once in place at a desired location within the blood vessel, a restraining member that applies a radially compressive force, which holds the frame in the collapsed smaller diameter configuration, is removed so that the frame expands. The frame may be held in the collapsed smaller diameter configuration by a variety of suitable restraining members such as a delivery catheter or removable outer sheath. For example, in one embodiment, the frame is deformed into the smaller diameter configuration within the lumen of a delivery catheter 49, and then expanded in the blood vessel lumen by longitudinally displacing the frame out the distal end of the delivery catheter 49 to thereby remove the radially compressive force of the delivery catheter 49. Although not illustrated, a pull line similar to pull line 19 discussed above in relation to the embodiment of FIG. 1 may be provided to apply additional radially expanding force to the filaments to supplement their inherent spring force, and is preferably provided in the embodiments having a radially expandable member 14 comprising an inflatable balloon where inflation of the balloon creates a radially compressive force on the tubular member 13.

In the embodiment illustrated in FIG. 7, balloon 42 is inflated into contact with the aorta wall 31 to an outer diameter that completely occludes the outer blood flow stream downstream of the renal arteries 32. Thus, the outer blood flow stream is directed into the branch vessels 32. However, the balloon may be configured to inflate to an outer diameter which does not completely occlude the downstream outer blood flow stream, as discussed above in relation to the embodiment of FIG. 3.

Figure 8A:
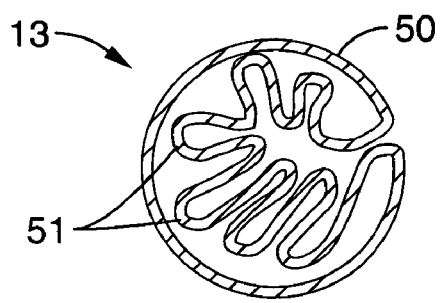
FIG. 8A is a transverse cross sectional view of an alternative embodiment having an expandable tubular member with a small profile wrapped configuration.
Figure 8B:
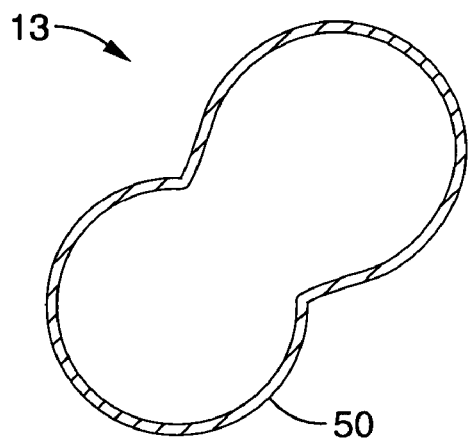
FIG. 8B is a transverse cross sectional view of the tubular member shown in FIG. 8A, illustrating the tubular member in the expanded unwrapped configuration.
Figure 9A:
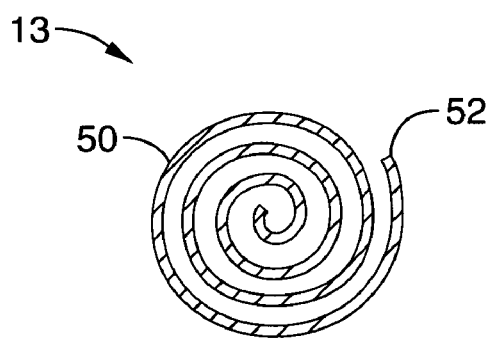
FIG. 9A is a transverse cross sectional view of an alternative embodiment having an expandable tubular member with a small profile wound configuration
Figure 9B:
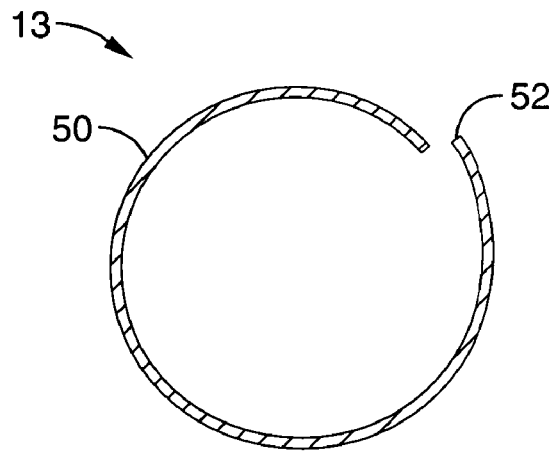
FIG. 9B is a transverse cross sectional view of the tubular member shown in FIG. 9A, illustrating the tubular member in the expanded unwound configuration.

FIGS. 8 and 9 illustrate transverse cross sectional views of an alternative embodiment in which the tubular member 13 comprises a sheet 50 configured to unwind from a wound low profile to an unwound radially expanded configuration to thereby radially expand the interior passageway 18 of the tubular member 13. FIG. 8A illustrates an embodiment in which the sheet 50 has a section wound back and forth into a plurality of folds 51. A restraining member (not shown) such as an outer sheath or delivery catheter is removed so that the sheet 50 unfolds as illustrated in FIG. 8B. The sheet section configured to be folded is preferably a thinner walled or otherwise more flexible than the section of the sheet that is not folded. In another embodiment illustrated in FIG. 9A, the sheet 50 is wound around itself into a rolled-up configuration having a free edge 52 extending the length of the sheet 50, which unrolls to the radially expanded configuration illustrated in FIG. 9B. A variety of suitable unfurling or uncoiling configurations may be used in a tubular member which is radially expandable in accordance with the invention including a rolled awning-type mechanism, and the like.

Figure 10:
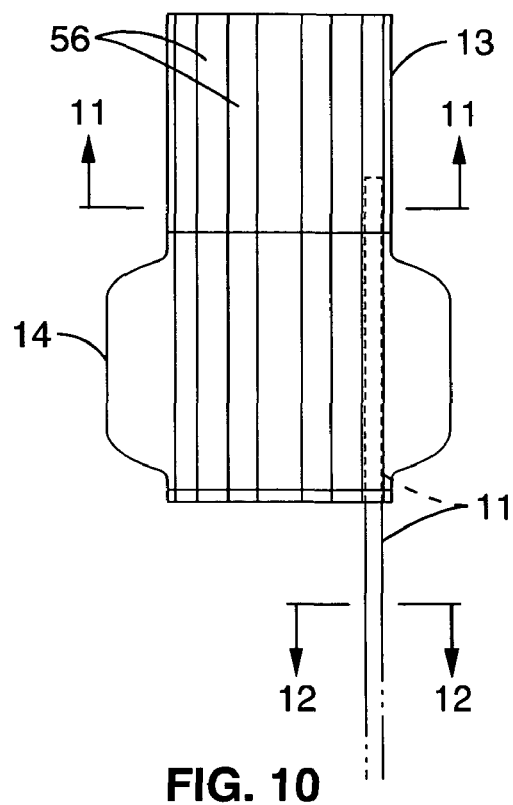
FIG. 10 illustrates an enlarged view of a distal section of an alternative embodiment having an expandable tubular member comprising a plurality of inflatable wall chambers or balloons secured together to form the tubular member.
Figures 16, 17:
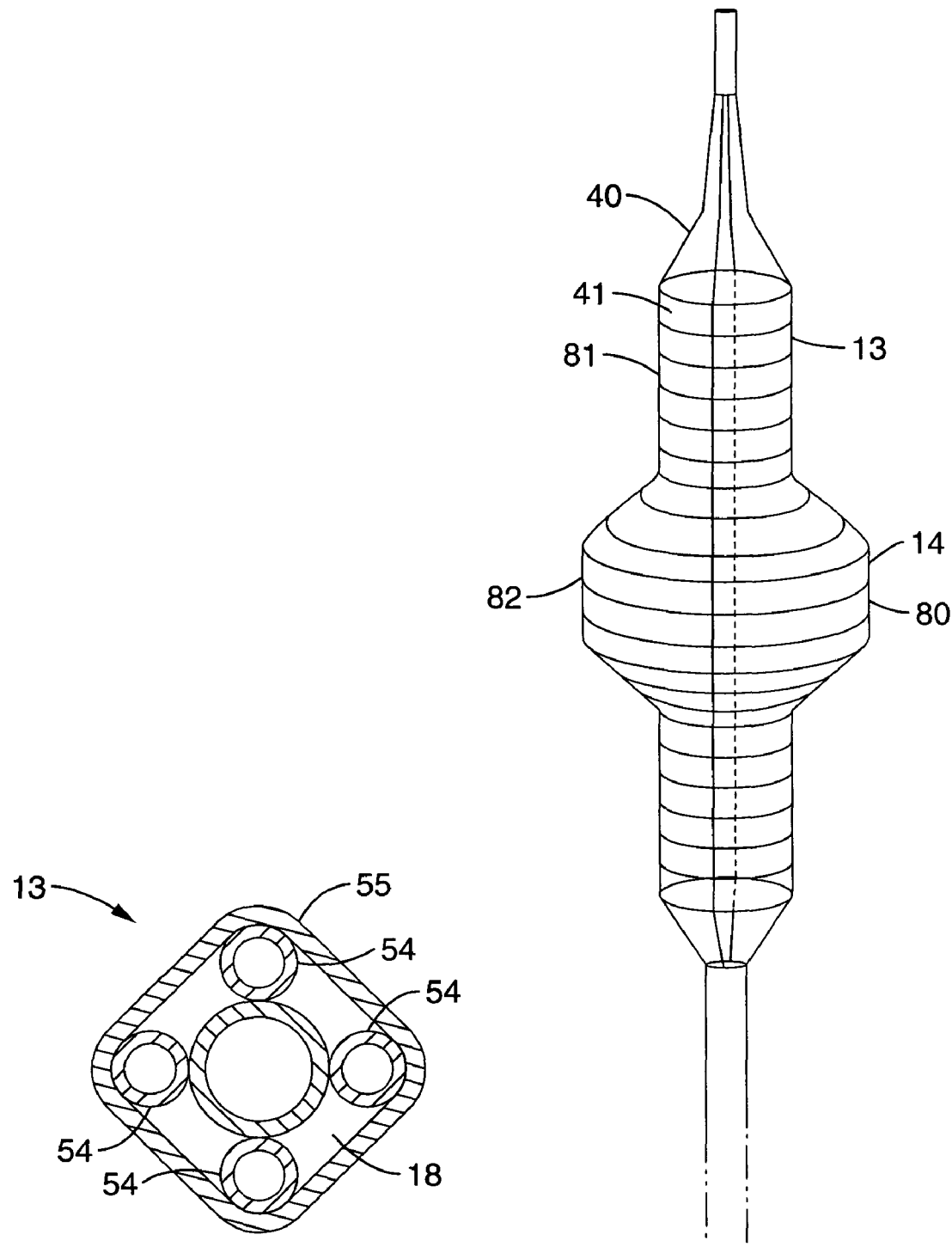
FIG. 16 is a transverse cross-sectional view of an alternative embodiment of an expandable tubular member comprising a plurality of inflatable balloons within an outer sheath.
FIG. 17 is an enlarged view, partially in phantom, of a distal section of an alternative embodiment having a radially expandable member comprising a radially enlarged section of the expandable tubular member.

FIG. 16 illustrates a transverse cross sectional view of an alternative embodiment in which the tubular member 13 comprises a plurality of inflatable balloons 54 within an outer sheath 55. The balloons 54 can be inflated from a non-inflated low profile configuration to an inflated configuration. In the inflated configuration illustrated in FIG. 10, inner passageway 18 is defined between the inflated balloons in part by the sheath 55. Preferably, three or more balloons 54 are provided to in part define the inner passageway 18. Balloons 54 are preferably formed of a noncompliant material such as PET, or a complaint material such as polyethylene having reinforcing members such as wire members. Although four, cylindrical balloons 54 are illustrated in FIG. 10, it should be understood that a variety of suitable configurations may be used, including balloons having outer channels such as a spiraled balloon defining an outer spirally extending blood flow channel, similar in many respects to perfusion balloons for dilatation. An inflation lumen is provided in the catheter shaft 11 in fluid communication with balloons 54.

Figure 11:
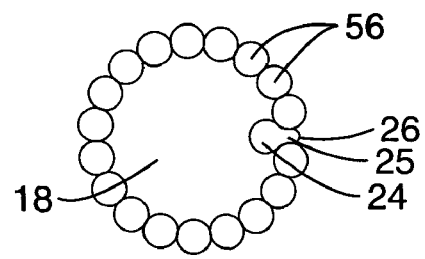
FIG. 11 is a transverse cross sectional view of the catheter shown in FIG. 10, taken along line 11—11.
Figure 12:
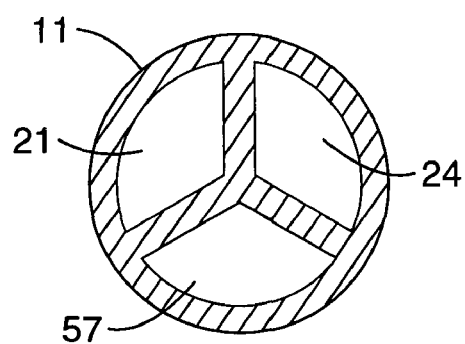
FIG. 12 is a transverse cross sectional view of the catheter shown in FIG. 10, taken along line 12—12.

FIGS. 10–12 illustrate an alternative embodiment in which tubular member 13 comprises a plurality of inflatable fluid-communicating wall chambers 56. In the embodiment of FIG. 10, the tubular member 13 comprises a plurality of tubular balloons joined together. For ease of illustration, the radially expandable member 14, which is an inflatable balloon, is shown as a transparent material. As best illustrated in FIG. 11 showing a transverse cross sectional view of the tubular member 13 taken along line 11—11, each tubular balloon 56 is joined to adjacent balloons along a length thereof, to thereby define the tubular member interior passageway 18. As best illustrated in FIG. 12 showing a transverse cross sectional view of the catheter shaft 11 taken along line 12—12, the multi-lumen shaft 11 defines an inflation lumen 21 in fluid communication with balloon 14 on an outer surface of the tubular member 13, an agent delivery lumen 24 in fluid communication with agent delivery port 25, and a second inflation lumen 57 in fluid communication with the tubular balloons 56. Agent delivery opening 26 adjacent to the shaft agent delivery port 25 provides a pathway for agent delivery from the lumen 24 to exterior to the tubular member 13. The balloons 56 can be bonded together using a variety of suitable methods including as adhesive, heat fusion bonding, or solvent bonding such as with hexa-fluoro isopropanol (HFIP) for PET balloons. The tubular member 13 defined by the balloons 56 can be deflated and compressed, folded, pleated or otherwise reduced in size for introduction and advancement within the patient's blood vessel. In a presently preferred embodiment, the pressure required to inflate the balloon 14 is significantly lower than the pressure used to inflate the balloons 56 forming the tubular member 13, so that inflation of the balloon 14 does not deform the tubular member 13.

Figure 13:
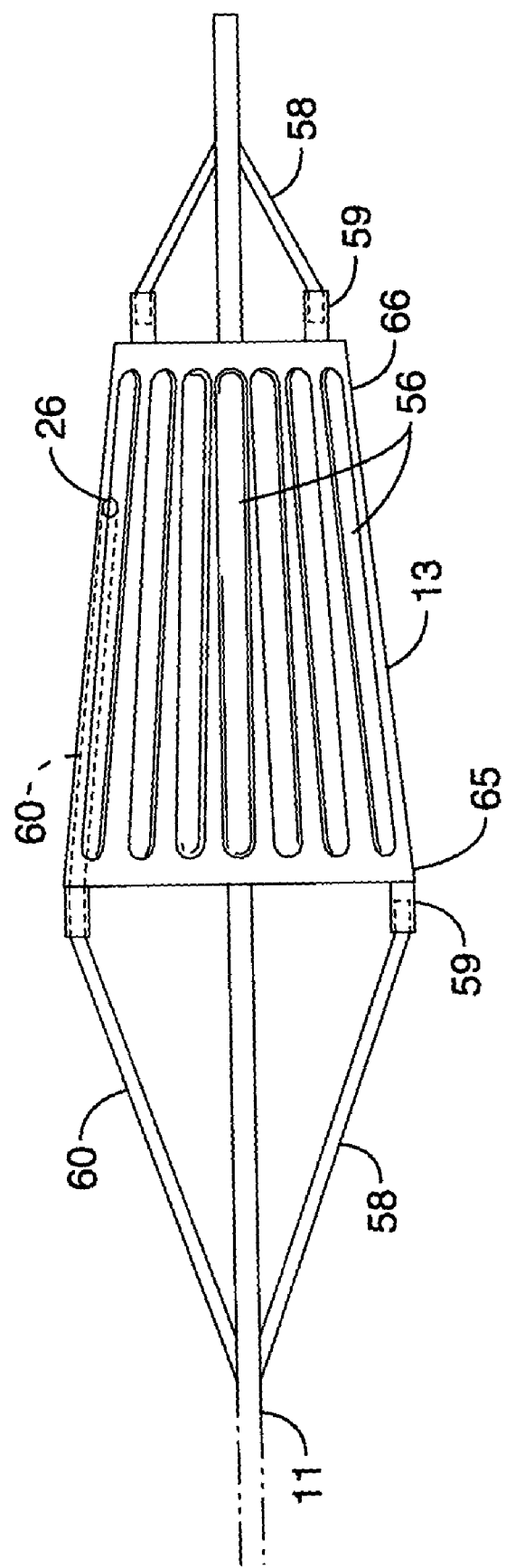
FIG. 13 illustrates an enlarged view of a distal section of an alternative embodiment having an expandable tubular member comprising a plurality of fluid-communicating wall chambers, wherein the tubular member has a conical shape.
Figure 14:
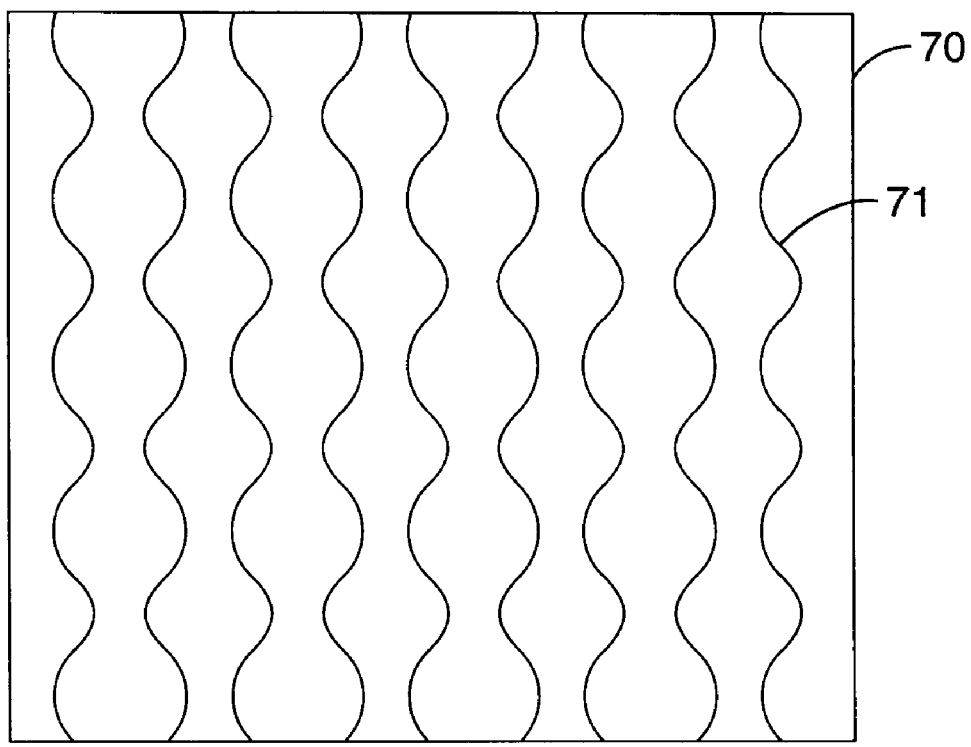
FIG. 14 is an elevational view of fused polymeric sheets used to form the tubular member, having curved seal lines forming the fluid-communicating chambers.

FIG. 13 illustrates an enlarged distal end of one embodiment having a tubular member 13 formed of a plurality of inflatable fluid-communicating wall chambers 56, in which one or more inflation tubes 58 extend from a port in the sidewall of shaft 11 in communication with inflation lumen 57 to the distal and/or proximal end of the tubular member. The inflation tubes 58 are in fluid communication with the wall chambers of the tubular member 13, and are used for delivering inflation fluid into the wall chambers 56 to thereby inflate the tubular member 13. In the embodiment of FIG. 13, the inflation tube 58 is secured to tubular member 13 by an adapting member or channel 59 at an end of the tubular member 13. One or more agent delivery tubes 60 extend from a port in the shaft 11 in fluid communication with agent delivery lumen 24 and into a wall chamber 56 of the tubular member 13. Agent delivery port 25 at the distal end of the agent delivery tube 60 extends to and in fluid communication with an agent delivery opening 26 in a wall defining a wall chamber of the tubular member 13. The section of the agent delivery tube 60 located within a wall chamber of the tubular member is illustrated in phantom in FIG. 13. Thus, one or more wall chambers of the tubular member can be used for agent delivery rather than inflation of the tubular member 13.

In the embodiment illustrated in FIG. 13, the tubular member 13 is conical. The conical tubular member 13 tapers from a large diameter down-stream end 65 to a smaller diameter up-stream end 66, so that the large diameter down-stream end 65 of the tubular member 13 forms the radially expandable member 14. Consequently, a separate radially expandable member 14 is not provided.

Figure 15:
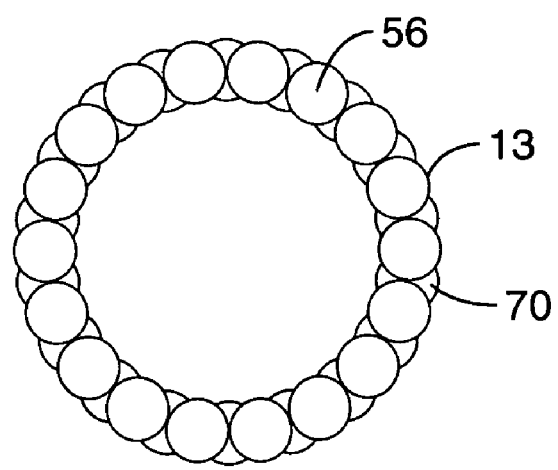
FIG. 15 is a transverse cross-sectional view of a tubular member formed of the sheets illustrated in FIG. 14.

The tubular member 13 comprising a plurality of inflatable fluid-communicating wall chambers 56 illustrated in FIG. 13 can be formed by heat sealing or fusing, as for example with a laser, two sheets of a polymeric film together with a plurality of longitudinally extending seal lines, so that each wall chamber is between adjacent seal lines. The seal lines forming the wall chambers do not extend to the proximal most and/or distal most end of the tubular member, so that the wall chambers are in fluid communication with one another. A variety of suitable materials can be used to form the sheets including polyolefins, low density polyethylene, polyurethane, polyamides, nylon, polyether block amide, polyethylene terephthalate, and other thermoplastics. The fused sheets are then wrapped into a cylindrical shape and the edges secured together to form a tubular member 13, which is collapsible and foldable into a compact configuration for advancement within the blood vessel. In the embodiments illustrated in FIGS. 10–13, the seal lines defining the wall chambers of the tubular member 13 extend in straight lines along a length of the tubular member. FIG. 15 illustrates an elevational view of fused sheets 70 for forming an alternative embodiment of a tubular member 13 in which the wall chambers 56 are defined by curvilinear seal lines 71 to form interleaved cells, so that a more complete occlusion is provided by the tubular member 13. FIG. 16 illustrates a transverse cross-sectional view of an expanded tubular member 13 formed from the curved seal lines.

FIG. 17 illustrates an alternative embodiment similar to the embodiment shown in FIG. 7 except that the radially expandable member 14 comprises a radially enlarged section 80 of the tubular member 13. Thus, the frame 40, with sheath 41 thereon, forming the tubular member 13 does not have a uniform outer diameter, but instead radially expands from a collapsed configuration to define a smaller diameter section 81 defining tubular member 13, and a larger diameter section 82 defining the radially expandable member 14.

The dimensions of catheter 10 are determined largely by the size of the blood vessel(s) through which the catheter must pass, and the size of the blood vessel in which the catheter is deployed. The length of the tubular member 13 is typically about 50 to about 150 mm, preferably about 80 to about 120 mm. The tubular member 13 has an unexpanded outer diameter of the tubular member is typically about 1 to about 5 mm, preferably about 2 to about 4 mm, and a radially expanded outer diameter of about 40 to about 140 mm, preferably about 60 to about 120 mm. The radially expanded interior passageway 18 of the tubular member 13 is typically about 30 to about 130 mm, preferably about 50 to about 110 mm to provide sufficient perfusion. The interior passageway 18 of the tubular member 13 has a radially expanded inner diameter, which may be between about 100% and 600% in many cases, or possibly even so much as about 1000% to about 6000% larger than the unexpanded inner diameter of the passageway 18. The radially expandable member 14 has a length of about 10 to about 50 mm, preferably about 20 to about 40 mm. The expanded outer diameter of the radially expandable member 14 is about 10 to about 35 mm, preferably about 15 to about 30 mm. In the embodiment having a conically shaped tubular member 13, the tubular member dimensions given above should be understood to refer to the distal most (i.e., up-stream) or smaller diameter end of the conical member, unless otherwise stated. Similarly, in the embodiment in which the radially expandable member 14 comprises the larger diameter end of a conically shaped tubular member, the radially expandable member dimensions should be understood to refer to the proximal most (i.e., down-stream) or larger diameter end of the conical member.

Typically, the shaft 11 has an outer diameter of about 1 to about 5 mm. The inflation lumen 21 has an inner diameter of about 0.02 to about 0.06 mm, and the agent delivery lumen has an inner diameter of about 0.01 to about 0.04 mm. The length of the catheter is about 40 to about 100 cm, preferably about 60 to about 90 cm.

Referring now to FIGS. 18–26, additional embodiments of the present invention are illustrated. These additional embodiments are generally further refinements of the embodiments shown in FIG. 7 and FIG. 13 above, wherein the expandable member is comprised of a frustro-conical collapsible frame. However, in these embodiments as generally described, the collapsible frame is comprised of proximal (downstream) and distal (upstream) loops, with the open conical tubular member extending therebetween, which renal flow assembly is attached to the longitudinal catheter shaft. The frame/sheath is configured to expand when released from the delivery catheter such that the proximal (downstream) loop engages and seals against the aortic wall, thereby creating a seal without the need for a secondary inflatable member. Further, in these embodiments, the loops of the collapsible renal flow assembly radially expand as they move from the collapsed state by standing up into a generally orthogonal orientation to the catheter shaft and thus generally orthogonal to the cross-section of aortic flow when deployed in-vivo.

As seen in FIG. 18, an assembly 100 made in accordance with certain preferred embodiments of the present invention are illustrated. The system 100 is comprised of a delivery sheath 105 with the catheter shaft 113 and tubular member 110 slideably contained within the inner lumen of the delivery sheath 105. The proximal end of the delivery sheath 105 has two ports, 123,126, the function and use of which are similar to that described above with reference to FIG. 1 and which will be familiar to those of skill in the art. The distal end of the catheter shaft 113 includes a conical tubular member 110; the function and structure of which will be further described below. In preferred embodiments, the overall length of the delivery sheath will be about 50 cm (range of about 10 cm to 80 cm, in certain circumstances between about 40 cm and about 80 cm), and the length of the conical tubular member 110 is about 5 cm (range of about 3 cm to 10 cm). The distal end of the catheter shaft 113, carrying the tubular member 110, can typically be slideably deployed such that it extends about 5 cm from the distal opening of the delivery sheath 105, in a range of 0 cm to about 15 cm. FIG. 19 is similar to FIG. 18 and illustrates a separate guiding catheter (or other interventional catheter familiar to those skilled in the art) 120 being used in conjunction with the catheter assembly 100 described above with reference to FIG. 18.

Referring now to FIGS. 20–20A, further details of the distal end of the catheter assembly 100 shown in FIG. 18 are illustrated. The proximal opening of the conical tubular member 110 is maintained when deployed by use of a wire loop 111 preferably superelastic nickel-titanium (Nitinol™) or other resilient metallic or polymeric material, and preferably has a diameter of about 30 mm, with a range of about 15 mm to 40 mm). Similarly, an opening at the distal end is also maintained using a Nitinol™ loop 112 or similar technique and preferably has a diameter of about 15 mm, ranging from about 5 mm to 25 mm). The two wire loops that form the proximal and distal ends of the conical tubular member are attached to the catheter shaft. In a most preferred embodiment, the catheter shaft 113 is configured to be relatively small in outside diameter, preferably about 1.5 French (or about 0.020") so that a separate guiding catheter 120 of about 6 French (0.078") OD can be simultaneously contained within the delivery sheath 105 after the tubular member 110 is distally deployed. Yet, the catheter shaft 113 is also most preferred to be a fluid-delivery shaft, the structure and function of which is described below. In order to have all of these attributes, it is contemplated that the catheter shaft is preferably formed by a metallic hypotube made from either nickel titanium allow (NiTi) or stainless steel, although those skilled in the art would know that the catheter shaft could be a composite construction involving a polymeric extrusion, metallic stiffening members, and/or braided fibers.

Further details of the structure and arrangement of the distal portion of the catheter assembly 100 and conical tubular member 110 are illustrated in FIG. 20. The conical tubular member is formed by the larger diameter proximal loop 111, smaller diameter distal loop 112, and membrane 114, all of which are attached to the distal end of catheter shaft 113. Details of various illustrative examples for attaching loop elements 111,112 are shown in FIGS. 26A–D.

More specifically, FIG. 26A illustrates one useful embodiment of how loops 111, 112 can be attached to the catheter shaft 113 in an integrated fashion. In order to minimize the profile while maximizing robustness, the ends of the loop 119 are flattened, set within indentations formed in the wall of shaft 113, and secured there such as by welding. FIG. 26B illustrates how a loop 111, 112 can be attached to the catheter shaft can be attached to the catheter shaft 113 with the ends of the loop inserted into slots formed through the wall of the catheter shaft and thereafter secured by welding or soldering. The advantage of these embodiments is that the loop ends do not occupy the internal lumen of the catheter shaft and thereby do not impinge on the lumen for fluid delivery. FIG. 26C illustrates how a loop 111, 112 can be attached to the catheter shaft with the ends of the loop inserted into a hole formed in the top wall of the catheter shaft where the loop ends are inserted into the lumen of the catheter shaft and secured by one of several options, including welding, soldering, adhesive, swage and crimping. FIG. 26D illustrates how a loop 111, 112 can be attached to the catheter shaft similar to that shown in FIG. 26C except with the loop ends inserted into a hole formed in the bottom wall of the catheter shaft. FIG. 26D illustrates how a distal loop 112 can be attached to the shaft by inserting the loop ends into the axial end-hole of the catheter shaft, thereby eliminating the need for penetration into or through the wall of the catheter shaft.

FIG. 26E illustrates an alternate embodiment for the catheter shaft 113, where the proximal section of the shaft 113 is a triple-lumen configuration with the loop ends inserted and secured into each of the smaller lumens, and the distal catheter shaft extends as a single lumen to the distal end of the device. The membrane 114 is formed as a thin film or sheet attached in a frustro-conical shape by virtue of its attachment to the proximal loop 111 and distal loop 112 and thereby forms the surface of the conical tubular member. The membrane 114 is also attached to the catheter shaft 113 so that it is sealed along its length between the loops 111, 112. In a highly beneficial embodiment, the membrane 144 is comprised of a substantially non-porous material and therefore provides a shield that isolates fluid communication between the inner bore passageway within the tube and the external space surrounding the tube and between the outer surface of the membrane and the wall of the vessel in which it is deployed. This provides the benefit of isolating blood flow along the outer surface of the conical tubular member 110 to flow only around the outside of the tubular member, e.g. into renal ostia there, and substantially preventing leakage through the membrane 114 and into the inner lumen of the member where flow perfuses downstream from the device.

In still a further illustrative example of increasingly more detail, the membrane 114 may be a single layer material that is folded over the loops 111, 112 and back on itself and sealed there, such as via solvent, adhesive (e.g. adhesive glue, adhesive tape, etc.), heat, or other sealing techniques.

One exemplary method that is considered acceptable for attaching and sealing the ends of the membrane 114 to the loops 111, 112 is to thermally bond the material along a circumferential seam adjacent the loop, as seen in the broken away view shown in FIG. 20A.

Another embodiment, shown in FIG. 20B, illustrates multiple fluid infusion (exit) ports 115 provided in certain preferred embodiments of the present invention. If the infusion ports 115 are arranged around the circumference, even distribution of fluids is more likely accomplished, and also, by placing the infusion ports 115 on the outer surface, preferential release toward the outer surface of the conical tubular member 110 which acts as a deflector, and thus not down the center portion that leads distally, is ensured. As a result, a structure made in accordance with this embodiment of the present invention provides more evenly distributed delivery of fluid or agent around the circumference of a tubular delivery member, and therefore more evenly distributed delivery into multiple respective ostia of arteries or other body lumens having varied locations around the main vessel and surrounding the delivery device.

A cross-section of a further exemplary structure shown in FIG. 21A illustrates that the conical tubular member 110 comprises a longitudinal support member as a spine or "backbone" formed in this particular embodiment from a distal drug delivery shaft 113, that may be for example about 1.5F (0.02" diameter).

For the purpose of further illustration, one beneficial method for forming the tubular member, adapting it to proximal and distal radial support members or rings, and adapting that assembly to the spine of the delivery shaft is as follows (not shown). A flat sheet of the material is cut having 4 sides with one pair of opposite, parallel sides of differing lengths and another pair of opposite sides providing angled tapers between the ends of the first pair. Then the first pair of parallel ends are wrapped over onto themselves and secured, e.g. with adhesive tape, to form longitudinal pouches at each end. Next, straight wire is fed through these pouches, after which the opposite ends of the straight wires are brought together to form a loop therebetween that includes the sheet. This forms the sheet between the wires into substantially the tubular form but for the gap between the opposing ends of the sheet. Then the partially tubular sheet is adapted to a drug delivery or spine member extending distally from the distal end portion of a delivery shaft. This is done by wrapping the opposing ends of the sheet around the spine concurrent with applying adhesive or other sealing modality.

It can also be seen that a guiding catheter shaft 120 fits within the delivery sheath 100. In preferred embodiments the guiding catheter is an 6F (0.078" diameter) catheter and the delivery sheath 100 has an inner diameter of 8F (0.104") so that there is at least 0.5 F clearance between the backbone 113 and the guiding catheter 120. As will be readily understood by those skilled in the art, the complete product for use in a catheter lab could therefore comprise an 8F sheath that includes the conical tubular member 110 and an 8F dilator, and could further optionally include a 0.035 inch (or similar size) introducer length guide wire and a guide wire introducer. One skilled in the art will also understand that an off the shelf 8F introducer sheath set could also be used, wherein the drug infusion catheter assembly is a completely separate product used in combination.

Referring now to FIG. 22, further details of the proximal end of the sheath 100 illustrated in FIG. 18 are shown. The main shaft is split into a "Y" configuration at the proximal end 122, in accordance with conventional catheter and sheath construction and results in a straight port 123 and a side port 126, however, for purposes of this embodiment of the present invention, it is critical that the angle between the two branches 123,126 be chosen so that the advancement and retraction of the conical tubular member assembly 110 is facilitated. A sufficiently gentle curve with no sharp edges or abrupt turns must be provided. In certain embodiments, this structural requirement may result in additional structures being necessary, e.g., a specially shaped plunger may be required to occupy a section of the sheath so that a smooth turn is provided. The straight port 123 is preferably used for dilator placement during insertion of the guide catheter, and this section is preferably short so that standard guide catheter lengths can be utilized. The distal end of the straight port 123 includes a hemostasis valve 124 that is preferably of an 8F construction with a side flushing port. The side port 126 houses the conical tubular member assembly 110 during sheath insertion and therefore must be of sufficient length to house accommodate the collapsed device, and is therefore between 5–10 cm in length in preferred embodiments. The distal end of the side port 126 includes an O-ring assembly 125 with a side flushing port. The proximal ends of both the side port 126 and the straight port 123 typically include a stopcock (not illustrated) when in use. As will be understood by those familiar with catheter insertion, it is possible to have the functions of the sidearms 123,126 described below reversed and have the device retracted within the straight port 123 and operate the dilator and guiding catheter through the angled side port 126.

Figure 23A:
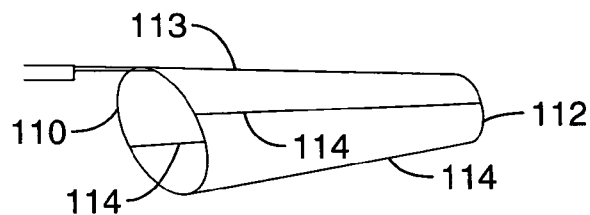
FIGS. 23A–23F are illustrative perspective views of various configurations of support wire that can be used with the balloons of the present invention.
Figure 23B:
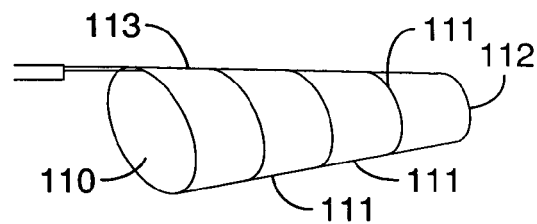
Figure 23C:
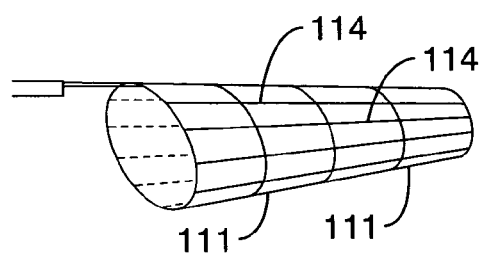
Figure 23D:
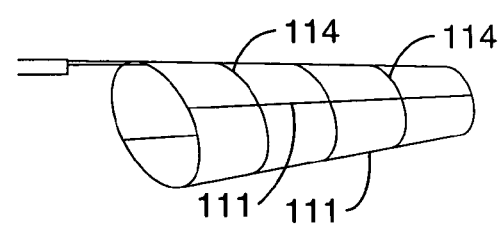
Figure 23E:
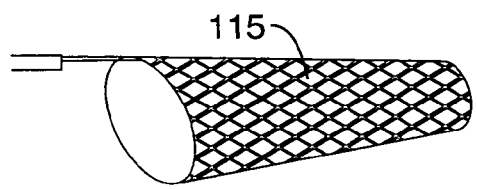
Figure 23F:
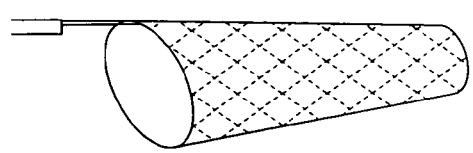
Figure 24:
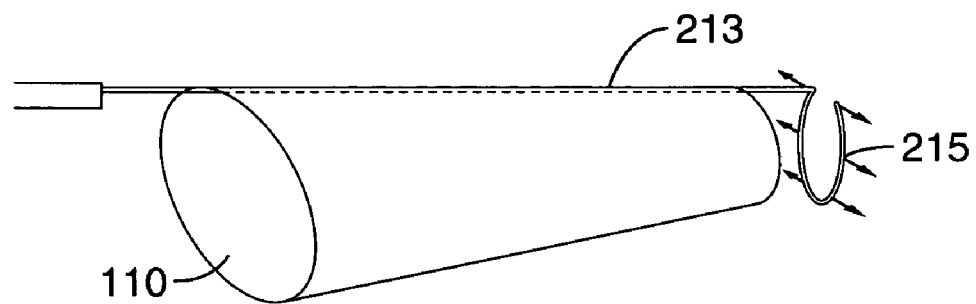
FIGS. 24–25 are illustrative perspective views of alternate embodiments for the distal tip and drug infusion portion of the device.
Figure 25:
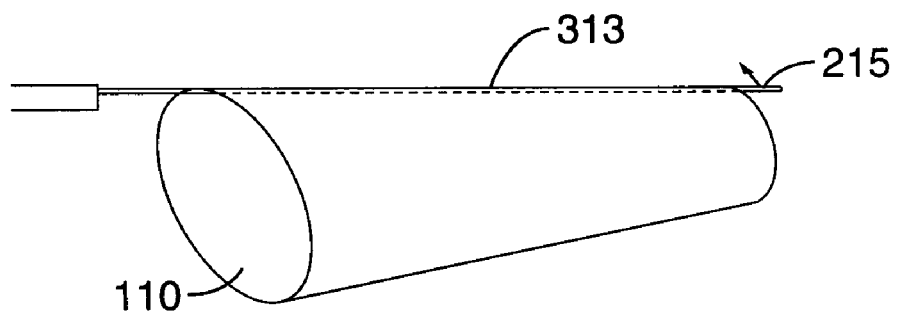
Figure 26:
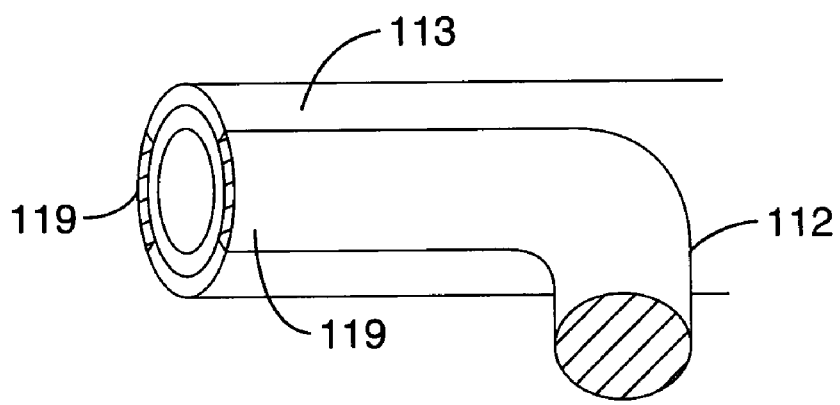
FIG. 26 is a perspective view of a detail showing the attachment of components that form the assemblies of the present invention.

As noted above with reference to FIG. 20, upon deployment, the shape of the conical tubular member 110 is maintained by structural members such as Nitinol wires that permit the sheath to be collapsed so that it may be delivered, yet which are shape retaining such that upon deployment within a body lumen, the desired shape is achieved and maintained. In order to facilitate folding of the sheath 100, prevent bunching and prevent loose material that could flutter or possibly interfere with openings in the main lumen, such as the openings of the renal arteries described above with reference to the use of other embodiments of the present invention, in certain preferred embodiments, additional multiple support members 114 are provided. As seen in FIG. 23A, multiple longitudinal support members 114 can be provided, and similarly, as seen in FIG. 23B, multiple radial or circumferential support members 111 can be provided that are disposed between the loops 111,112 described above. FIGS. 23C–23D illustrate how the structures of FIGS. 23A–23B can be combined in an orthogonal rid. S will be readily appreciated by those of skill in the art, the number of additional supporting members is chosen based on material characteristics, sheath construction and size, flexibility requirements, physician preference and a number of other factors. As seen in FIGS. 23E–23F the support members may be a mesh or grid or woven structure as well as the circumferential and longitudinal members described above. In such an embodiment, the mesh 115 may alternately be an exoskeleton in which the wires or other support members are on the outside, or they may be an endoskeleton (FIG. 23F, with the support wires on the inside and the material attached to the outside. The design of the mesh can be chosen to provide maximum support during expansion and preferential folding during collapse. Preferred embodiments will also prevent material from billowing during use, as mentioned above. However, a design consideration is that these embodiments might have a larger collapsed profile than those embodiments with less support wires, such as those illustrated in FIGS. 23A–23D Further details of the distal tip and drug infusion aspects of certain preferred embodiments of the conical tubular member 110 are illustrated in FIGS. 24–25. As explained above with reference to FIG. 20, the backbone 113 carries a fluid or drug to the distal portion of the conical tubular member 110 and infusion ports 115 admit this fluid into the vessel. In the embodiment shown in FIG. 24, the backbone 213 is of an alternate "pigtail" construction such that the drug infusion ports 215 are arrayed as shown on a shaft that forms a circle that is of a larger diameter than the distal end of the conical tubular member 110. The distal tip of the pigtail 213 is atraumatic and includes the multiple externally directed drug infusion ports 215, which among other benefits are intended to promote mixing of delivered agent into the outer flow path around the tubular flow deflector assembly.

Another embodiment of the distal end construction is shown in FIG. 25. In this embodiment a straight shaft 313 terminates in a single infusion port 315 disposed near the distal end of the shaft 313, which is shown in one variation to be located just behind the atraumatic tip that forms the distal end of the shaft 313. It is believed that proper positioning of a single infusion port 315 appropriately upstream of the renal arteries, together with an appropriately dimensioned (e.g. diameters, taper, length) for tubular member, will allow for sufficient mixing in the outer blood flow around tubular member 110 to provide even distribution of a drug or fluid both external to the outer surface of the conical tubular member 110 and circumferentially therearound to provide adequate distribution to any vessel branches. However, in certain particular circumstances such as for certain indications, the distribution may be acceptably uneven or even preferred, moreover, the simplified construction may provide other advantages, such as for example simplicity and cost of construction, as well as more cooperative design for the intended interrelationship between the renal flow device and delivery sheath or other devices as elsewhere herein described.

Methods of preparing and in-vivo placing and using the various renal flow device of the invention are described in significant detail below with respect to the embodiments of FIGS. 27–33. However, for the purpose of further illustrating the general beneficial aspects of the embodiments of FIGS. 18–26, their general methods of use are briefly herein introduced as follows.

The guide sheath 100 is initially inserted into an introduction site along a femoral artery, and is then advanced into the iliac artery and ultimately into the aorta (not shown). Typically, though not necessarily, this procedure is carried out under fluoroscopic guidance, and the tip of the sheath 100 is advanced until it is properly positioned with respect to the respective ostia of the renal arteries. Placement of the tip of the sheath within the abdominal aorta may be accomplished with or without first advancing a dilator over a guide wire to the location that may provide a coaxial rail for the guide sheath 100. Because of the bulk of the renal flow assembly 110 at the distal end of the sheath assembly, a vacuum may be created as the device is advanced. To avoid air being drawn into the system, it will be important to maintain positive pressure through the side ports of the device, typically via saline infusion. The size and structure of the large loop 111 is chosen so that when deployed, it seals against the aorta wall. The final position of the device prior to drug delivery may be verified by fluoroscopic techniques including bony structure visualization and antegrade dye injection as well as in some instances dye injection through the drug diffusion ports. After the device has been properly placed and deployed, the assembly is locked into place using an O-ring adapter around the device shaft, as known in the art. Positive saline flow may be maintained through the side flush port.

When the device is deployed, flow through the infusion ports can be initiated at any time the physician deems appropriate by connecting the infusion ports to an infusion pump or other source of fluid under sufficient pressure to create a flow through the device and into the body lumen, so that a desired rate of administration is achieved and maintained.

Using a guide wire, a coronary guiding catheter can be introduced through the hemostasis valve of the sheath, through the deployed device and into the heart. Proper engagement and preferential blood flow into branch vessels (such as the renal arteries) can be verified using the coronary guiding catheter or other angiographer catheter such as a pigtail catheter to inject dye distal to the device (with antegrade aortic flow).

After the interventional procedure is competed, post procedure removal is begun by first withdrawing the guide catheter through the device, which may or may not require a guide wire, all the way through the hemostasis valve. In a preferred method, a guide wire is not used and the deflector assembly is captured by the advancement of the sheath over the device, slowly collapsing the device inside the sheath. Most preferably, the device would be recaptured within the sheath and pulled back into the side arm 126, as described above, the position it was in prior to deployment. After the device has been retracted a guide wire can be introduced through the straight arm and through the sheath into the vessel, allowing removal of the sheath from the vessel while maintaining guide wire access for safety and subsequent wound sealing procedures Further beneficial embodiments for a renal flow system according to the invention are additionally herein described by reference to FIGS. 27–33 as follows.

Figure 27:
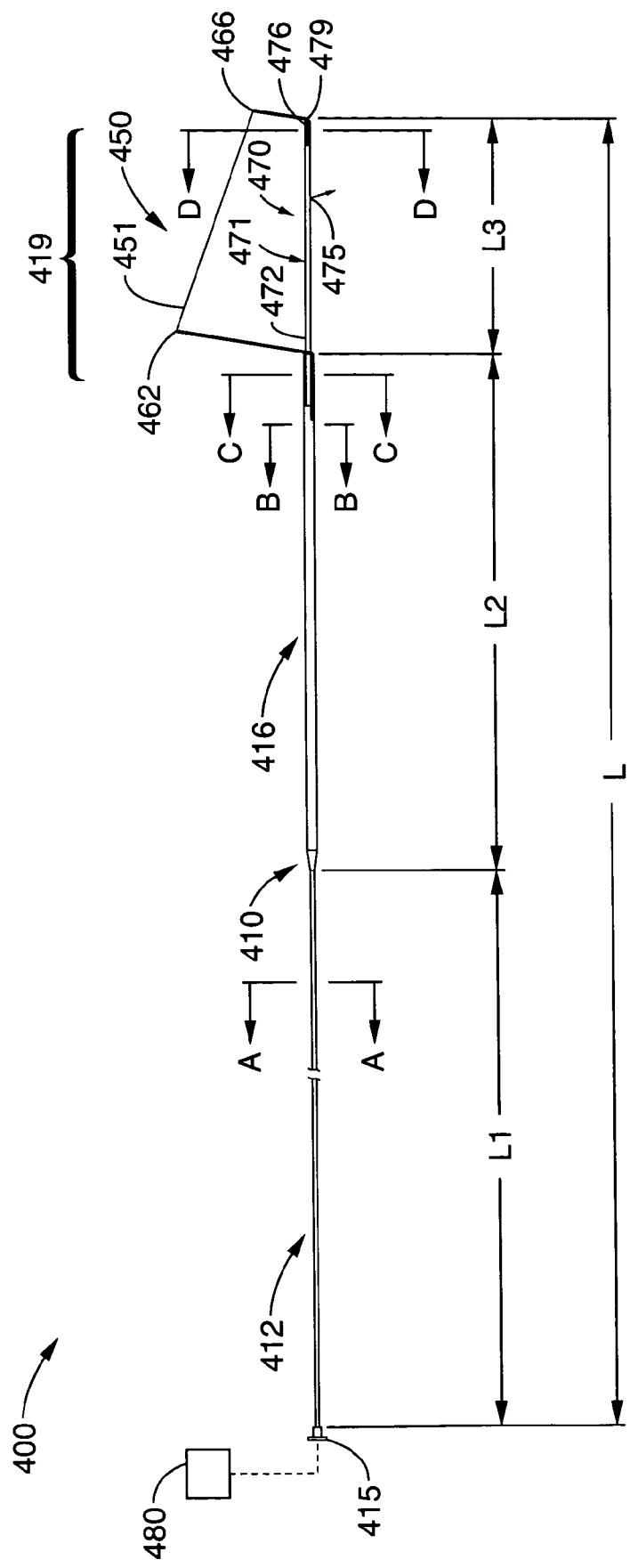
FIG. 27 is an elevational view of another embodiment for the renal flow device of the invention.

One further embodiment for another highly beneficial renal flow device is shown in FIG. 27 as follows. Generally speaking, renal flow device 400 includes a shaft 10 with a proximal shaft section 412 terminating proximally at a coupler 415 (e.g. such as a luer adapted) and a distal shaft section 416 that is attached to renal flow assembly 450 and local fluid delivery assembly 470 along a distal end portion 419 of device 400.

In one beneficial aspect of device 400, the relationship between proximal shaft section 412 and distal shaft section 416 according to this embodiment shown in FIGS. 27–29D provides for optimized inter-cooperation of the device 400 with other devices within a common delivery sheath. For example, this embodiment enhances the ability to use one guide sheath, and therefore one femoral puncture wound, to deliver device 400 to the renal area of the abdominal aorta for localized renal drug delivery, as well as deliver other devices distal to that area, such as coronary devices for procedures, e.g. for angiography and/or angioplasty or stenting. Further details of such system and methods of use are developed in detail below.

In another beneficial aspect, the design of shaft 410 according to the present embodiment also allows for optimal proximal stiffness and distal trackability. More specifically, proximal shaft section 412 is a substantially stiff member with a single tubular wall 413 that defines an interior lumen 414, as shown in finer detail in FIG. 29A. Wall 413 is typically of a relatively stiff construction in relation to distal shaft section 416, and may be for example a "hypotube" which is defined as a single tubular member constructed of metal, such as for example stainless steel or nickel-titanium alloy. Or, tubular wall 413 may be constructed of other sufficiently stiff material such as polyimide, high density polyethylene, or composite construction of reinforcing support members combined with polymer or other matrix material.

Distal shaft section 416 according to the embodiments shown in FIGS. 27–29D is also generally a single tubular member with a tubular wall 417 that defines an inner lumen 418. However, in contrast to proximal shaft section 412, distal shaft section 416 is constructed of a substantially more flexible material than the relatively stiff proximal shaft section 412, such as for example a polymer tube, such as for example PEBAX™, nylon, polyethylene, or polyurethane. According to this construction, distal shaft section 416 is more trackable in order to negotiate the tortuosities of the more distal anatomy within which it is to be disposed during use, such as within diseased sections of the abdominal aorta. Moreover, as the more distal component of the shaft 410, distal shaft section 416 must also first traverse the femoral bifurcation in a retrograde approach to renal artery positioning, and therefore the flexibility of that section is beneficial. While the proximal shaft section 412 may also follow to such location during distal advancement, the distal purchase of the distal shaft section makes such tracking more achievable, even with stiffer proximal shaft materials.

Distal shaft section is also shown in FIG. 27 to be larger than proximal shaft section 412. According to embodiments where distal shaft section 416 is provided as a heat-shrinkable material, such as a radiated or cross-linked material, the relatively larger distal shaft section 416 may be secured to the proximal shaft section 412 by heat shrinking the proximal end of distal shaft section 416 down over the distal end of proximal shaft section 412. The distal end of proximal shaft section 412 may be further treated for adhesion such as by etching, scoring, or otherwise processing the metallic tube end to accommodate a heat seal with the polymer of the distal shaft. In addition, adhesive may be used either together with or in the alternative with such heat-shrink coupling of the adjoining tubes 412,416.

Other variations of construction are contemplated, for example using similarly sized proximal and distal shaft sections 412,416 and using other techniques to secure them to each other. For example, a heat shrinkable distal shaft section 416 of similar size to proximal shaft section 412 may be expanded at its proximal end under heat and pressure, such as air pressure or being forced over a tapered mandrel or other tapered structure. Then the expanded proximal end of distal shaft section 416 may be placed over the distal end of proximal shaft section 412 and subsequently reheated to cause heat recovery, or shrinking, down onto proximal shaft section 412 as previously described immediately above. However, the relatively increased size of distal shaft section 416, or conversely the relatively decreased size of proximal shaft section 412, may in some circumstances provide benefits with respect to various modes of intercooperative use with coronary guiding catheters and other distal treatment devices within common guiding sheaths, as will be further developed below. Again, however, the relative sizes and construction of the shaft sections may be varied according to one of ordinary skill so long as the general objectives of the assembly may be achieved.

Referring again to the detailed components of device 400 shown in FIGS. 27–29D, distal shaft section 416 is secured to renal flow assembly 450 along a distal end portion 419 of device 400 that is intended to be positioned within the abdominal aorta in a region adjacent to the renal artery ostia. Renal flow assembly 450 is shown to include a tapered tubular member 451 having a tapered tubular wall 452 that tapers from an open annular proximal end portion 452 to an open annular distal end portion 456. Each end portion 452,456 is supported by an annular support ring 462,466, respectively, such that the renal flow assembly is adjustable between a collapsed condition and a radially expanded condition, respectively, which are characterized and operate in a similar manner as previously herein described with respect to the embodiments of FIGS. 13 and 18–26.

Moreover, each of the annular support rings 462,466 are beneficially constructed in a particular manner allowing for the desired annular support of conical tubular member 451, as well as optimizing the integration of the assembly of tubular member 451 and rings 462,466 into the overall device 400 as follows.

Each of annular support rings 462,466 has a ring-shaped portion that supports the respective end 452 or 456 of conical tubular member 451. Each of annular support rings 462,466 is constructed according to a beneficial embodiment from a nickel-titanium alloy. Such alloy may be in one variation in a super-elastic state. This allows the respective rings to be delivered through a delivery lumen of a guide sheath in a folded, collapsed condition to the abdominal aorta in the area adjacent the renal artery ostia; then when released from the confines of the delivery lumen, the support rings elastically recover to the substantially expanded, annular condition shown in FIGS. 27 and 28 that is adapted to isolate aortic flow to the renal ostia, as elsewhere herein described. In another variation, the alloy may be provided in a shape-memory mode, wherein at room temperature and prior to insertion into the body the rings are malleable into the collapsed condition for easy delivery through a delivery lumen of a guide sheath to the renal aortic location; upon exposure to body temperature and upon removing radial confinement from the guide sheath, the alloy "recovers" due to heat-induced memory to the expanded condition shown. Despite the highly beneficial embodiments just described, other superelastic or shape memory alloys, or further variant constructions or materials, may be appropriate substitutes for certain indications and custom tailored designs without departing from the intended scope herein.

As further shown in detail in FIG. 28 and variously in FIGS. 29C–D, the respective ring-shaped portions just described above for each annular support ring 462,466 also extend between two respective adjacent end portions that extend at similar angles from the plane of the respective ring-shaped portion. These end portions are used to secure the respective support rings to various structures in order to integrate the renal flow assembly 450 to shaft 410 of device 400 as follows.

For example, proximal support ring 462 has two end portions 463,475 extend lo proximally from the annular plane of support ring 462 and within the opening at the distal end of lumen 418 within distal shaft section 416. End portions 463,465 are secured within lumen 418 together with proximal end 472 of tubular member 471 of fluid delivery assembly 470 (described in more detail below), as shown in FIGS. 28 and 29C. These elements may all be secured together by heat shrinking the distal shaft section 416 down onto end portions 463,465,472, and/or may involve other securement modes in addition to or alternative to heat shrinking, such as for example solvent or adhesive bonding. In addition, in order to ensure an efficient seal around the various end portions that are generally stiff metal members, an additional layer of thermoplastic polymer, such as non-irradiated polymer tubing, (not shown) may be added coaxially within lumen 418 but around end portions 463, 465,472; by then heat treating the area, distal shaft section 416 shrinks down over the intermediate polymer layer which flows to sufficiently seal all areas that might otherwise create seal gaps in the assembly.

With respect to distal support ring 466 and by reference to FIGS. 28 and 29D, end portions 467,469 extend proximally from the annular plane of support ring 462 and within the opening at the distal tip 479 into lumen 473 of tubular member 471 of drug delivery assembly 470. These end portions 469,467 are secured within lumen 473 to create a closed distal tip 479, which may be accomplished according to a variety of modes. In one highly beneficial embodiment wherein tubular member 471 and end portions 469,467 are of metal construction, they may be secured by welding, soldering, swaging, or adhesives may be used. In the event tubular member 471 is of polymeric construction, a heat shrink process or adhesives may be used to secure tubular member 471 down over end portions 467,469, such as previously described above for securing proximal support ring 462 to distal shaft section 416.

Referring now to more detail of renal fluid delivery assembly 470 and by further reference to FIGS. 27–29D, lumen 473 is located within elongate tubular member 471 and extends between an open proximal end 472 and an open distal end 476 of tubular member 471. Lumen 473 communicates externally of tubular member 471 through drug delivery port 475 that is located in a side wall of tubular member 471 between proximal and distal ends 472,476 and closely adjacent distal end 476. Proximal end 472 of tubular member 471 is fit within the open distal end of distal shaft section 476 such that lumen 473 is in fluid communication with lumen 418 of distal shaft section 416, which is in fluid communication with lumen 414 of proximal shaft section 412, which further communicates exteriorly of device 400 through a proximal port at proximal coupler 415. However, lumen 473 is sealed at the distal end 479. Accordingly, renal flow device 400 is adapted to couple proximal coupler 415 to a pressurized source of fluid (as shown schematically at pressurized fluid source 480) in FIG. 27, such as for example of diagnostic or therapeutic agent, and transport fluid therefrom through lumens 413, 418, and 473 and out through local drug delivery port 475 for local delivery into blood flow surrounding expanded renal flow device 450. While local delivery port 475 may have varied locations along tubular member 471, in one highly beneficial embodiment it is located as close as possible to distal tip 479, such as for example as shown at 475', as such distal positioning optimizes the distance for mixing with the annular blood flowing proximally over renal flow assembly 450.

It is further contemplated that the interplay between local fluid delivery assembly 470 and renal flow assembly 450 may be further optimized by modifying the specific shape of conical tubular member 451 to other shapes that are adapted to enhance mixing between the local fluid delivery port and the renal ostia. One such modification that is believed to be highly beneficial provides the conical tubular member 451 with a localized stand-off from longitudinal axis L of distal shaft section 416 in order to provide wall clearance for adequate mixing around conical tube 451 in the event distal shaft section 416 is positioned against an aortic wall. This variation is shown in increasing detail in FIGS. 30–31, respectively, and is further described as follows (similar reference numerals are used for similar structures between the Figures).

Figure 30:
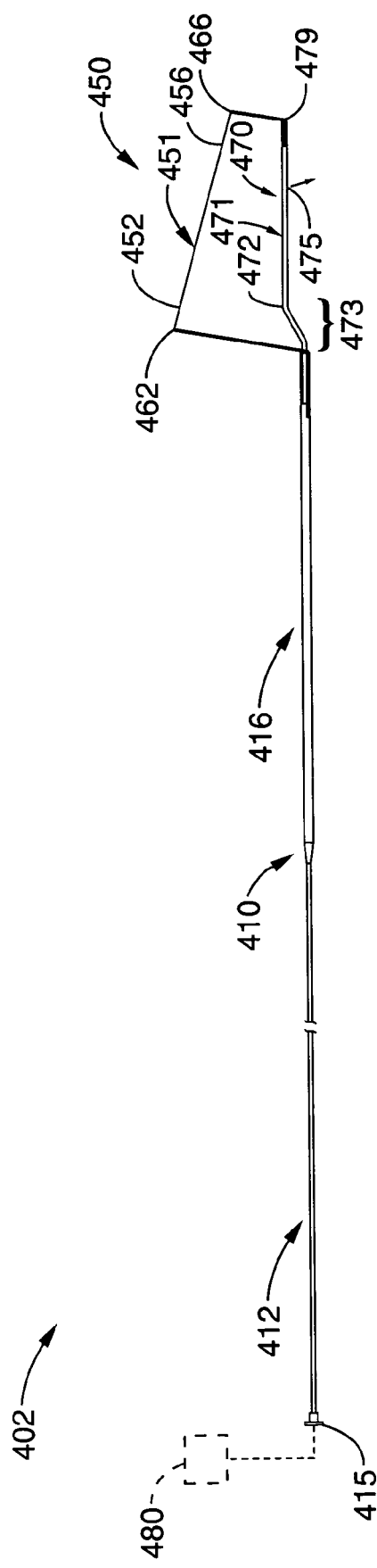
FIG. 30 shows an elevational view of another embodiment for the renal flow device of the invention.
Figure 31:
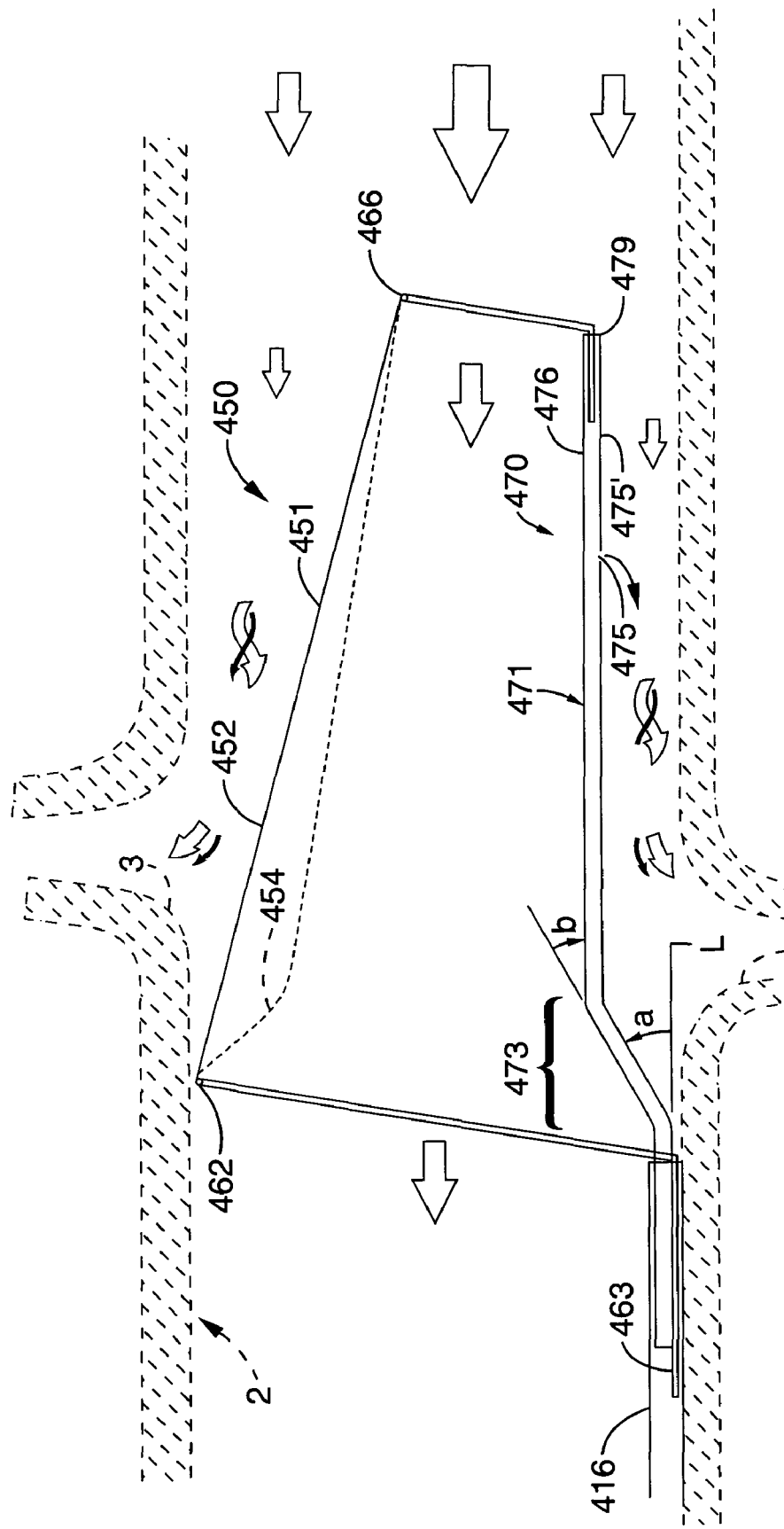
FIG. 31 shows an exploded view of the distal end portion of the renal flow device shown in FIG. 30, and shows various details of the renal flow assembly in relation to its attachment to the shaft of the device.

In the embodiment shown in FIGS. 30–31, renal flow assembly 450 beneficially includes a stand-off region 453 that is located: (i) in one longitudinal aspect, along the proximal end 452 of conical tubular member 451, and (ii) in another radial aspect, along the region corresponding to renal fluid delivery assembly 470. This stand-off region provides a more drastic taper than in other regions of the renal flow assembly 450, and therefore provides more clearance from aortic wall when positioned in the expanded condition in-vivo, as shown in FIG. 31 by reference to a position within an abdominal aorta 2 adjacent renal ostia 3,4 (shown in shadow). Such enhanced localized fluid mixing in the outer blood flow around conical member 451 is illustrated in FIG. 31 by way of large bolded arrows, representing aortic blood flow between outer and inner paths, and smaller bolded arrows representing locally delivered fluid flow from port 475.

Further to the specific embodiment shown in FIGS. 30–31, the stand-off region 453 is created at least in part by providing tubular member 471 of renal fluid delivery assembly 470 with a localized bend region that has a first bend at a first angle a from the longitudinal axis L of distal shaft section 416 and toward the plane of the proximal support ring 462. Stand-off region 453 further includes a second bend at a second angle b that is away from the plane of proximal support ring 462 such that the remainder distal portion of tubular member 471 extends in alignment with longitudinal axis L. While various values may be appropriate for bend angles a and b, one particular beneficial variation provides a sufficient stand-off of between about 1 to about 7 millimeters from longitudinal axis L (and therefore from arterial wall 2 when distal shaft section 416 is against the wall), and more particularly between about 2 to about 5 millimeters, and still more particularly between about 3 and about 5 millimeters.

Despite the particular beneficial aspects for the specific arrangement(s) just described for the stand-off of the embodiment in FIGS. 30–31, other angles or combinations of bends or shapes are also contemplated, in particular to the extent that mixing of fluid from port 475 and blood flowing around conical tubular member 451 is enhanced prior to filling the renal arteries. In one regard, additional variations for standoff "shapes" of the flow dividing conical member 451 may also be employed. One specific variation of this type extends the radially localized drastic taper region along region 473 just described to instead extend around the entire conical tubular member 451, such as shown in phantom at 454 in FIG. 31. Such circumferentially tapered wall shape may be provided for example in a pre-formed memory shape imparted to the material forming conical tubular member 451 itself, or may be provided by providing a restriction to expansion there, such as by a further radial reinforcing member similar to proximal and distal ring supports, except sized and positioned to restrain member 451 from expanding as it would when stretched between rings 462 and 466.

As previously introduced above, the embodiments shown and described by reference to FIGS. 27–31 beneficially provide for the ability to cooperate with additional devices within a common guide sheath in order to provide for localized drug delivery into the renal arteries while also providing for more distal procedures—all through one femoral introduction site. Further details of such cooperating system is described by reference to FIG. 32 as follows.

As shown in FIG. 32, a system 500 includes renal flow device 402, similar to the embodiment shown in FIGS. 30–31, aortic guide sheath 510, and coronary guide catheter 520. Guide sheath 510 includes a proximal coupler 513 with two proximal ports 514,515, in addition to a side flush port 616, which are all coupled to a common delivery lumen (not shown). Proximal ports 514,515 slideably receive renal flow device 402 and coronary guide catheter 520, respectively, within the common lumen according to an overall method of use to be further developed immediately below. The various components 402,510,520 are dimensioned to work together as a system: guide sheath 530 is adapted to house both renal flow device 402 and guide catheter 520 simultaneously while (i) renal flow device 402 is positioned to provide local drug delivery to the renal arteries through their ostia, and while (ii) coronary guide catheter 520 is positioned through renal flow device 402 and seated within a coronary artery (not shown) to facilitate a coronary intervention. As previously introduced above, this arrangement allows for isolated, localized renal drug delivery in conjunction with distal coronary procedures via one guide sheath 510, and thus via one femoral access site.

More specifically, such arrangement for system 500 shown in FIG. 32 may be accomplished in-vivo according to the following procedure, which though not shown in specific sequential steps is herein described by further reference to FIGS. 32–33 for the purpose of further illustration.

First, a femoral introduction site is established, such as according to the well-known Seldinger technique. This initial access includes (by reference to the sub-assembly shown in FIG. 33), placing an introducer sheath 530 across the puncture site and into the femoral artery with an upstream orientation toward the lower abdominal aortic bifurcation (not shown). Such introducer sheath 530 typically includes a proximal hemostatic valve 532 that allows for slideable engagement with devices therethrough while preventing substantial loss of blood. A dilator 540 is coaxially advanced through introducer sheath 530 and over a guide wire 550 that is steered, and guides dilator 540, to or beyond the region of the renal artery ostia in the abdominal aorta (not shown).

Once the guide wire 550 is positioned at the desired location in the aorta, dilator 540 is removed and guide sheath 510 is then placed over guide wire 550 and advanced through introducer sheath 530 so that the distal tip 516 of guide sheath 510 is positioned at least at the distal most region of renal flow device 402 is to be located during the desired selective renal flow procedure. In order to achieve such desired positioning for guide sheath 510, a radiopaque marker 517 may be provided at distal tip 516. Once guide sheath 510 is so positioned, guide wire 550 is removed proximally from guide sheath 510 through the port on proximal coupler 513 through which guide wire 550 had proximally extended during guide sheath delivery, such as for example through proximal port 514.

Thereafter, renal flow assembly 450 of renal flow device 402 is slideably engaged in a collapsed condition (not shown) within a delivery lumen of guide sheath 510 as follows. In one variation intended to reduce the possibility of air entrapment within folds of the tubular member 451, the conical tubular member 451 is collapsed and folded while submerged under a fluid, such as water, ringers lactate, or saline fluid. While still submerged, the conical tubular member 450 may then be introduced into the side port 514 also placed under the fluid bath. Or, conical tubular member may be inserted in the collapsed state into a catheter introducer (not shown) dimensioned for introduction into side port 514 while both are submerged; then the catheter introducer with collapsed tubular member 451 contained therein may then be inserted into side port 514, either while all components are submerged or after removing the tubular member/introducer sheath assembly from the fluid to the extent that the tubular member 451 is protected with the introducer sheath from substantial exposure to air. After introducing the tubular member into the side port 514 with the catheter introducer, the catheter introducer may then be removed, such as in the event a "peel-away" introducer is used as is known in the art; or, the catheter introducer may otherwise adapted to be removed proximally from the shaft of the renal flow device. Moreover, such introducer sheath may also be left resident in side port 514 during the procedure, in which case proximal withdrawal of tubular member 451 back into the catheter introducer after a procedure allows removal in the collapsed state inside of the catheter introducer.

Despite the chosen mode for initial introduction into guide sheath 510, collapsed renal flow assembly 450 is delivered distally through guide sheath 510 by pushing on proximal shaft section 512 until distal tip 479 is located at or closely adjacent to distal tip 516 of guide sheath 510. By then withdrawing guide sheath 510 proximally while maintaining positive pressure on renal flow device 402, renal flow assembly 450 is released from radial confinement by guide sheath 510 and adjusts to the desired expanded condition for selective renal blood flow, as elsewhere herein described.

Moreover, by proximally withdrawing guide sheath 510 sufficiently beyond distal shaft section 416 of renal flow device 402, then only the smaller diameter proximal shaft section 412 is located within guide sheath 510. This increases the available real estate within guide sheath 510 such that coronary guide catheter 520 may then be slideably introduced through proximal port 515 and advanced through guide sheath 510 along side of proximal shaft section 412 of renal flow device 402. This is done preferably over a coronary guide wire 560 which supports a typically pre-shaped tip 526 of guide catheter 520 in a substantially straightened condition, which aids advancing guide catheter 520 through guide sheath 510, and also through the inner flow lumen created by conical tubular member 451 of renal flow assembly 550.

Once the relationship is established between components as shown in FIG. 32, the guide catheter 520 and guide wire 560 may be advanced to the desired coronary artery ostium and used as desired for the intended coronary intervention. For example, a balloon angioplasty catheter 570 may be advanced through guide catheter 520 to a site of coronary occlusion in order to perform an angioplasty procedure there (either over wire 560, over another wire, or in a "fixed-wire" platform as would be apparent to one of ordinary skill). In addition, a stent 580 may be deployed at an occlusion site or site requiring stenting for protection against closure.

Various other devices may be used in system 500, either in addition or alternative to the devices herein described, and are still contemplated within the scope of the invention. For example, in addition or alternative to angioplasty or stent devices, atherectomy or other coronary treatment devices may be deployed. In another example, an angiographic catheter may be used as herein described similarly to references to a guide catheter 520, except merely for performing angiography. In this regard, it is believed that the provision of local renal drug delivery during an angiography procedure is one particular mode of the invention that is highly beneficial, as the concomitant dye delivery is known to present particular risks associated with kidney function. In still a further example, though system 500 has been previously described as a "coronary compatible system", other distal diagnostic or treatment devices may be used in combination with system 500 rather than coronary devices. Examples of such other devices which may be made compatible with the system of the present invention include without limitation: mitral valvuloplasty, annuloplasty, or other valve repair devices; endolumenal aortic graft anastomosis devices; cardiac electrophysiology devices such as ablation, mapping, or pacing devices; cardiac assist devices such as aortic balloon pumps; or neurovascular devices such as carotid artery filters or stroke treatment devices. Such devices may also be provided in a combination system kit according to the invention, such as being packaged together or otherwise bundled and sold or otherwise promoted for use together as a system.

In one regard, system 500 should be considered by reference to all of the components just described above by reference to FIGS. 32–33, which work together to achieve various highly beneficial results beyond a mere sum of their parts. In particular, such components may be packaged or sold together as a combination kit.

However, in another regard, system 500 should also be considered in view of the various beneficial combinations and sub-combinations of components described without requiring others of the described components. Certain combinations of components together achieve a particular objective that is in itself beneficial, even if such benefit provides one piece to an overall procedure that uses other components described. The combination of renal flow device 402 and guide catheter 520 is one such example. The further addition of guide sheath 510 provides yet another example. In some particular circumstances, certain components described above may not be necessary at all, depending upon the particular procedure to be performed as would be apparent to one of ordinary skill. For example, where only diagnostic angiography is intended in combination with local renal drug delivery, neither an angioplasty catheter nor a stent need be provided in the system. In another example, guide sheath 510 may be initially trackable over guide wire 550 to the site such that an elongated dilator 540 is not required.

It should be further appreciated that certain individual components, in particular renal flow device 402, define beneficial aspects of the invention when considered alone and are useful to the extent that they may be incorporated into systems such as herein described, or other systems not specifically herein described but apparent to one of ordinary skill based at least in part upon review of this disclosure. Moreover, it should also be appreciated that despite the highly beneficial stand-off aspect of device 402 shown in combination with system 500 in FIG. 32, other embodiments also herein described may also be suitable substitutes where appropriate, such as for example the embodiment shown in FIGS. 27–29D.

While many different particular dimensions, designs, and materials may be used for the various components of system 500 just described, one particular beneficial arrangement for a combination of guide sheath 510, renal flow device 402, and guide catheter 520 is provided as follows for the purpose of further illustration.

Guide catheter 520 may be chosen to have appropriate length, diameter, and tip shape dimensions for a particular case, but generally has a length between about 60 cm and about 120 centimeters, most typically about 80 centimeters, and has a diameter between about 5 French and about 8 French, more preferably about 6 French (which according to relatively recent advancements is sufficient to pass most desired coronary angioplasty and stenting devices therethrough).

Renal flow device 402 (or device 400 as an appropriate substitute) in the present variation is provided with the following dimensions. By reference to FIG. 27 (and by incorporation to the embodiment of FIG. 30), renal flow device has an overall length L between about 40 to about 80 centimeters, most usually between about 50 and about 70 centimeters, and still more typically about 55 centimeters long. Generally, the distal shaft section 416 is to be constructed according to a variety of factors whose relative weights may vary between particular indications. In one regard, distal shaft section 416 is desirably longer and/or more flexible construction for more tortuous aorta which may bias distal shaft section 416 away from the aortic wall such that the renal flow assembly 450 when expanded does not fully engage the aortic wall to provide the desired isolation of aortic flow around the assembly 450 into the renal arteries. In addition, the length of a larger distal shaft section 416 is directly proportional to the available flow rate for drug delivery through distal port 475, but is inversely proportional to the aortic blood flow rate over shaft 410. In other words, a larger diameter distal shaft section 416 increases flow therethrough for drug delivery, but also decreases flow thereover in the aorta (or in other words increases resistance to aortic flow downstream to the lower extremities).

Notwithstanding the foregoing, the length L2 of distal shaft section 416 is generally between about 1 and about 20 centimeters long, and in one particular variation is about 10 centimeter long. The diameter of distal shaft section 416 is generally about 5 French, whereas proximal shaft section 412 is generally about 1.5F, and is constructed of a stainless steel or nickel-titanium alloy hypotube having about a 0.020" outer diameter and about a 0.010" inner diameter. The length of proximal shaft section 412 is generally to be determined based upon the desired length for distal shaft section 416 and renal flow assembly 450, which generally has a length L3 between about 3 to about 10 centimeters, typically between about 4 and about 5 centimeters, and in one variation is about 4.5 centimeters.

According to the foregoing description by reference to FIGS. 27–32, one particular variation of a coronary intervention compatible renal flow system that is believed to be beneficial has the following dimensions: overall length L is about 55 centimeters; distal shaft section 416 has a length L2 of about 10 centimeters and a diameter of about 5F and of PEBAX™ tubular construction; proximal shaft section 412 has a length L1 of about 40.5 centimeters and a diameter of about 1.5F constructed of metal hypotube with 0.020" outer diameter and about 0.010" inner diameter; and renal flow assembly has a length of about 4.5 centimeters between a proximal support ring of nickel titanium having a diameter of 25 mm, a distal support ring of nickel titanium having a diameter of 10 mm, a proximal stand-off region extending from about 3 mm to about 5 mm from the longitudinal axis of the distal shaft section 416, and a sheet material tubular wall constructed of a ePTFE material having a wall thickness of 0.020 inches that forms conical tubular member 451.

Notwithstanding the many benefits of the coronary compatible renal flow system just described by reference to FIGS. 27–32, various aspects of the renal flow device embodiments according to those Figures may not be necessary, nor desired, in the event a compatibility with distal coronary procedures is not required. Such circumstance may occur for example, but without limitation, when localized renal drug delivery is intended for a congestive heart failure patient not receiving a coronary artery intervention. In such a case, certain design trade-offs otherwise made in order to provide the coronary intervention compatibility described now are not necessary sacrifices, and the device may be appropriately modified to optimize its performance specifically for renal drug delivery.

One beneficial example of such modification useful in cases where coronary device compatibility is not required is shown in FIG. 33 as follows. System 600 includes a renal flow device 403 that includes a shaft 410 with a substantially uniform outer diameter along proximal and distal shaft sections 412,416. In this construction, proximal shaft section 412 is not required to have a substantially reduced outer diameter versus the distal shaft section 416 because there is no requirement to cohabitate with a coronary guide catheter within a common lumen of guide sheath 610 as previously described above for the embodiments of FIGS. 27–32. Therefore, the construction for shaft 410 is simplified and more cost effective to make. In addition, a larger fluid flow lumen may be provided along the proximal shaft section 412 than was provided by lumen 413 shown in FIG. 29A. This larger inner lumen allows for less resistance and higher flow rates at a given applied pressure for delivering a drug from source 480 through exit port 475.

Notwithstanding the foregoing, it is to be appreciated that a renal flow assembly and interventional device such as a guiding catheter can be delivered through a common guide, whether or not tapered shafts are involved to maximize real-estate in sequential delivery (as elsewhere herein described for certain embodiments). In general, the tapered shaft embodiments provide the benefit of reducing the required size for a common delivery sheath, but larger delivery sheaths can always be used (though to some detriment of morbidity) for larger sized internally disposed shafts.

Moreover, though various of the embodiments beneficially provide for a combination device that includes a renal flow assembly that cooperates with an integrated, local fluid delivery assembly for providing localized agent delivery into the renal arteries from the aorta, it should be further appreciated that these components may be provided separately. For example, the various renal flow assembly embodiments may independently provide for the desired division of aortic blood flow between downstream and renal components, and a second separate device is delivered therethrough (or therearound) for local drug delivery into the isolated renal blood flow path into the aorta. A standard angiographic catheter may be used in some circumstances, though custom shapes such as for example a shaped tip with an acute radius that may essentially "hook" around the distal end of the tubular member after being delivered distally through its inner bore in a retrograde fashion.

It is to be appreciated that the various embodiments herein shown and described by reference to the Figures or otherwise may be further modified without departing from the scope of the present invention, in particular to the extent such modifications are substantially obvious or similar to the disclosed embodiments according to one of ordinary skill based upon this disclosure, and though such modifications may not be specifically herein shown or described.

In one regard, though the various embodiments are generally herein shown and described in relation to retrograde approaches to the renal ostia region of the aorta, antegrade access approaches are also contemplated, and the relationships of the devices, systems, and methods may be modified accordingly based upon this disclosure without departing from the presently intended scope.

In another regard, the various embodiments may be combined or substituted, or aspects thereof, without departing from the scope of the invention. For example, various beneficial embodiments are herein disclosed for providing a frustroconical flow dividing assembly to the area of renal artery ostia within the abdominal aorta, the description corresponding to each such embodiment or series of specifically related embodiments, such as FIGS. 13–15, 18–26, and 27–33; (such as for example regarding materials, design, methods of construction, and methods of use) is considered herein incorporated by reference with respect to the others of such embodiments, where appropriate according to one of ordinary skill.

For the purpose of further illustration, the inclusion of longitudinal or radial support members 114 described for the renal flow assembly embodiments of FIGS. 23A–F are further considered applicable to the various renal flow assembly embodiments in FIGS. 18–26, as well as the embodiments shown in FIGS. 27–33. In another illustrative example, the various aspects for renal flow device 402 that allow for the combined use in system 500 as described for FIGS. 32–33, as well as the combined methods of use therein described, may instead or in addition include other renal flow device embodiments elsewhere herein described as reasonable substitutes where appropriate.

Figure 34:
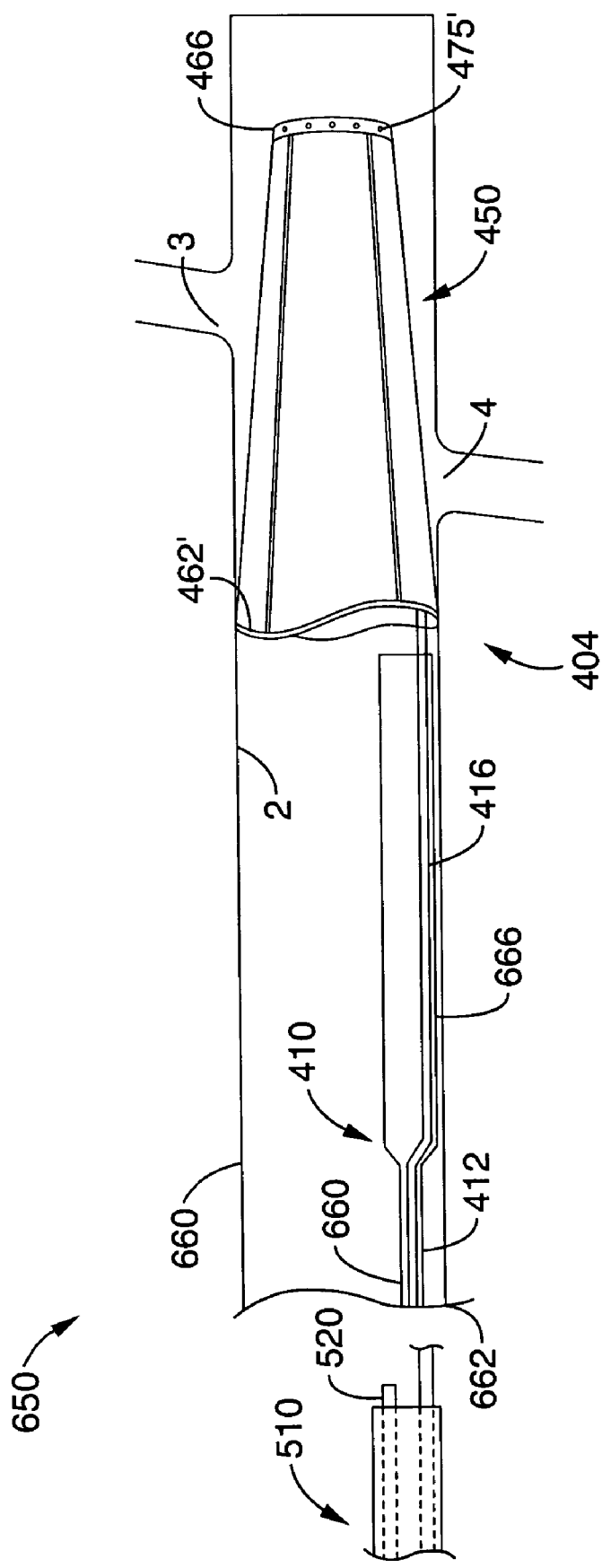
FIG. 34 shows an elevational view of another embodiment of a renal flow system according to the invention in the context of a region of abdominal aorta adjacent to the renal artery ostia, which is shown in longitudinally cross-sectioned view.

Another example of a modification that builds upon a combination of certain aspects of the embodiments above is shown in FIG. 34. As shown in FIG. 34, renal flow system 650 includes renal flow device 404 that has a renal flow assembly 450 with a frustroconical, tapered tubular member 450 that has enhanced support via longitudinal reinforcing members 614 similar to supports 114 shown in the embodiment for FIG. 23A. In addition, renal flow assembly 450 also includes circumferentially disposed and distally located drug infusion ports 475' arranged in a manner similar to that shown at ports 115 for the embodiment of FIG. 20A. Still further, shaft 610 is arranged without a substantial change in outer diameter between proximal shaft section 412 and distal shaft section 416, which in one regard is similar to the arrangement shown for the embodiment in FIG. 33. However, renal flow device 404 system 650 is arranged in a manner that is "coronary intervention" compatible as similarly described above with respect to the embodiment of FIGS. 27–32A as follows.

Shaft 410 has an outer diameter along proximal and distal shaft sections 412,416 that is sufficiently small to fit along side a coronary guiding catheter 520 within a guide sheath 510 in a similar arrangement previously provided by only proximal shaft section 412 in the embodiment of FIGS. 27–32A. However, renal flow device 404 further includes an additional coaxial member 660 that is coaxially disposed around shaft 410 (and generally integral to the overall assembly of device 404) with a distal member section 666 that is larger in diameter than proximal member section 662. Distal member section 666 is sufficiently large to aid in delivery, in situ expansion, and subsequent coaxial compression and retraction of renal flow assembly 450. Proximal member section 662 has a sufficiently small diameter, closely surrounding proximal shaft section 412, to be suited for cohabitating along side of a coronary guide catheter, e.g. a 6 French guide catheter, within a proximally disposed guide sheath such as guide sheath 510 shown in FIG. 32 while distal member section 666 is located distally (or upstream) beyond such guide sheath. Moreover, the annulus for internal aortic blood flow defined by distal support ring 466 is adapted to be of sufficient diameter to both allow for delivery of the distal coronary guide catheter 520 therethrough, while allowing for sufficient downstream flow in the exterior path into the renal arteries 3,4 as well as in the interior flow path for lower extremity perfusion via downstream regions of abdominal aorta 2.

Figure 35:
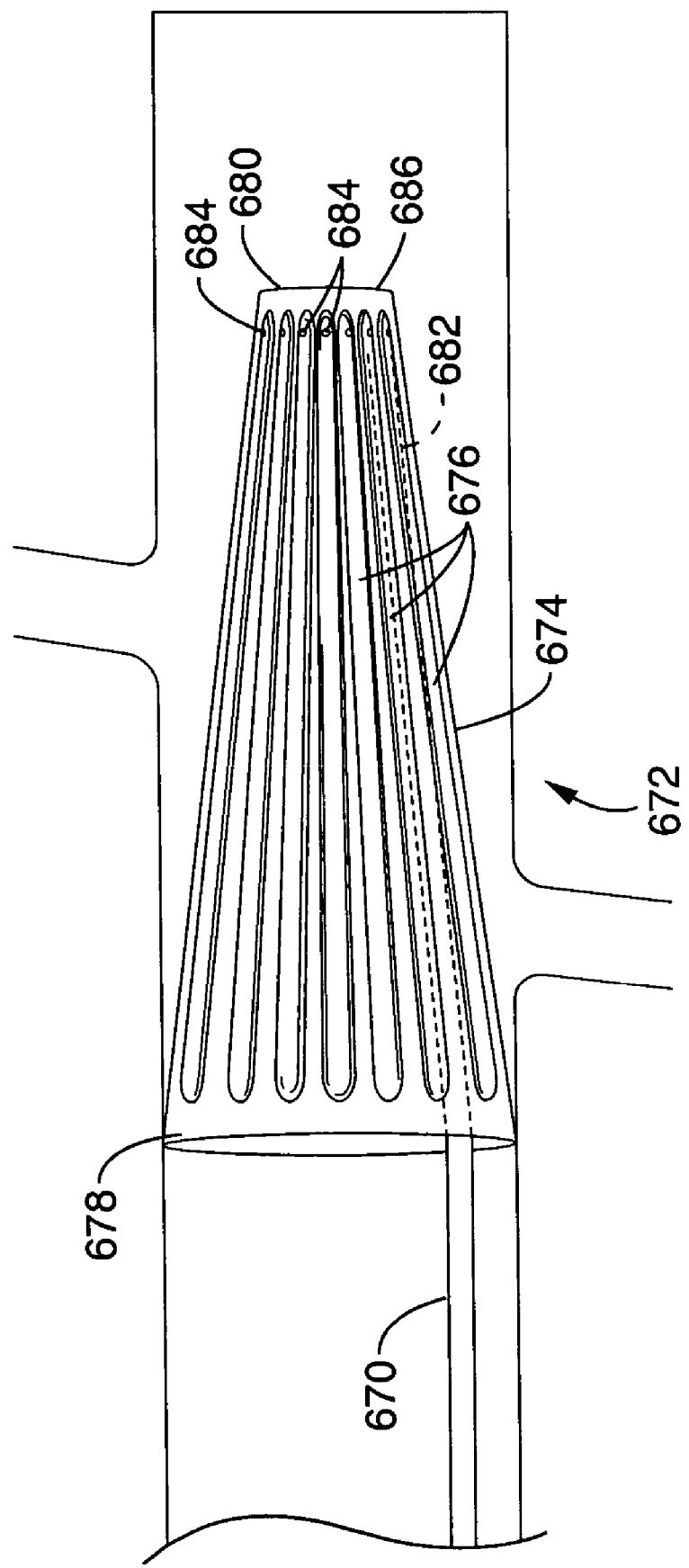
FIG. 35 shows a similar elevational view to that shown in FIG. 34, except in the context of yet another embodiment for a renal flow system according to the invention.

Yet still a further embodiment is shown in FIG. 35, which incorporates certain aspects of the renal flow device assemblies shown in FIGS. 27–34, in addition to aspects of the previous embodiments shown in FIGS. 10–15.

More specifically, FIG. 35 shows a renal flow device 405 that includes a renal flow assembly 672 having a wall 674 that is defined by an annular arrangement of circumferentially adjacent, longitudinal inflatable regions 676 that extend along a distally reducing, radially tapered, conical geometry away from a proximal inflatable region 765, terminating in a reduced annular tip region 680. Shaft 670 extends longitudinally along one radial position of wall 674 and terminates at distal tip 686. A plurality of circumferentially disposed drug delivery ports 684 are shown positioned around an exterior of wall 674 adjacent distal tip region 680, and are generally fluidly coupled to drug delivery member 682 that communicates via an internal lumen within shaft 670 to a proximal port for coupling to a pressurizeable source of drug or other fluid. In a further variation, a single port is contemplated through which drug delivery member 682 infuses drug into the exterior flow path around renal flow assembly 672, such as according to the embodiments shown in FIGS. 27–33. Further to this embodiment, shaft 670 also provides a conduit (not shown) for delivering inflation media from a proximal source outside of the body and into the balloon bladders that make up wall 674. According to this exemplary modification, a similar design to the embodiment of FIG. 13 is provided, except without the need for members such as shown at 58 and 60 in that Figure to inflate the respective balloon regions and infuse drug or other fluids through the respective renal delivery port, and in this regard for example incorporates certain aspects of the embodiment shown in FIG. 10.

It is further noted that certain of the embodiments above provide for a relatively fixed radial sizing of the proximal and distal ends of a frustroconically shaped tubular flow dividing member for providing selective renal flow contemplated. For example, the embodiments shown in FIGS. 27–34 incorporate annular rings of substantially rigid construction, e.g. metal, at the proximal and distal ends of the device. These support rings as therein shown have relatively fixed expanded diameters, respectively. With respect to the proximal rings in particular, they are thus adapted to seat well only within a limited range of well matched aortic diameters where they can achieve the desired flow isolation results. Moreover, with respect to the distal support ring dimensions, and thus overall tapered dimensions of the corresponding conical wall of the flow assembly, the substantially fixed sizing may be appropriate also for only a limited range of aortic sizes, else the desired division of flow between interior and exterior spaces relative to the conical wall is not achieved. Accordingly, it is contemplated that multiple devices having specified, unique dimensions, in particular radius dimensions defined at these end regions, may be provided in a kit. By using known or predicted aortic diameter of a particular patient in the region of the respective renal artery ostia, the appropriate device from the kit may be chosen.

Notwithstanding the foregoing, other embodiments above do provide for the possibility of more adjustable sizing of the renal flow assembly to seat within a wider range of aorta dimensions. For example, embodiments shown to include expandable balloons around the proximal support region of the conical flow dividing wall may provide for adjustable outer diameters over ranges of pressures to work in a much wider range of expected patients. In addition, the serpentine shaped proximal support ring 462' shown in FIG. 34 also provides for adjustable expanded annular diameter by reference to the plane orthogonal to the aorta 2 within which it is placed. The secondary serpentine shape along the axis of the aorta (longitudinal axis of the device 404) is modified over a range of expanded diameter though the annular shape in the orthogonal plane remains substantially annular and well matched to an aortic wall inner circumference.

Notwithstanding breadth and interchangeability of the foregoing, FIGS. 36A–K show various steps of one method for forming a specific renal flow device believed to be highly beneficial according to the present invention.

Figure 36A:
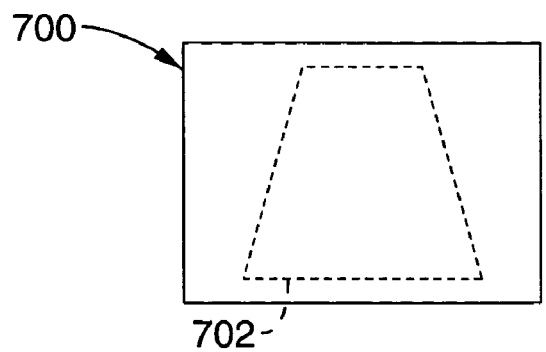
FIGS. 36A–K shows various views of different steps taken according to one beneficial embodiment for forming a renal flow assembly according to the invention.
Figure 36B:
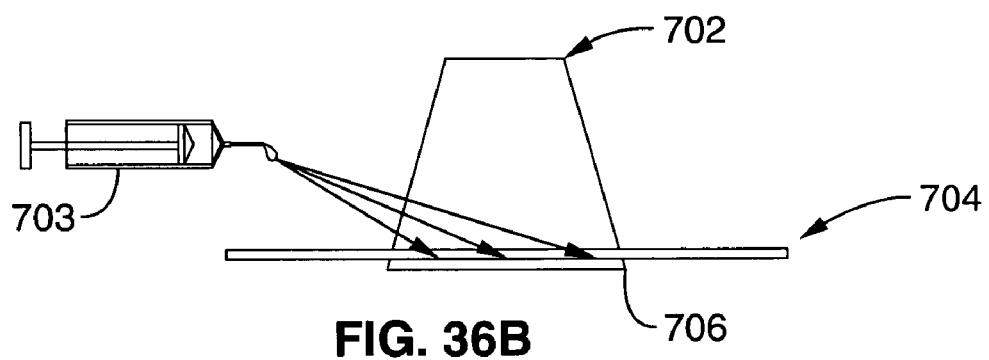
Figure 36C:
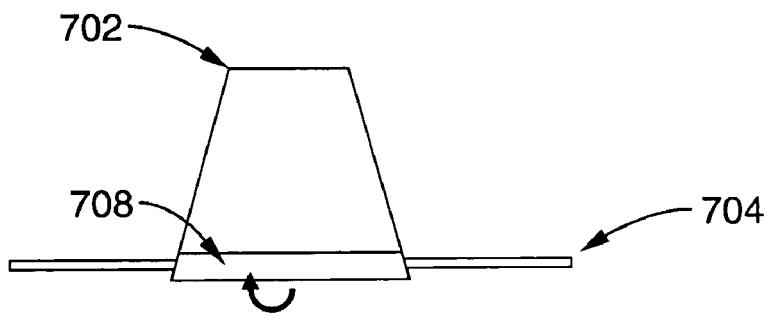
Figure 36D:
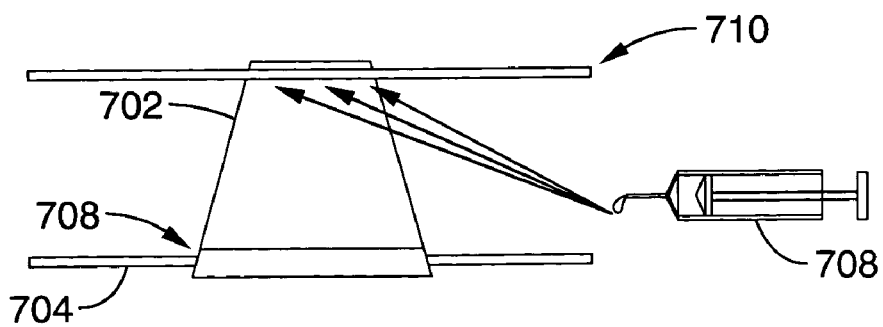
Figure 36E:
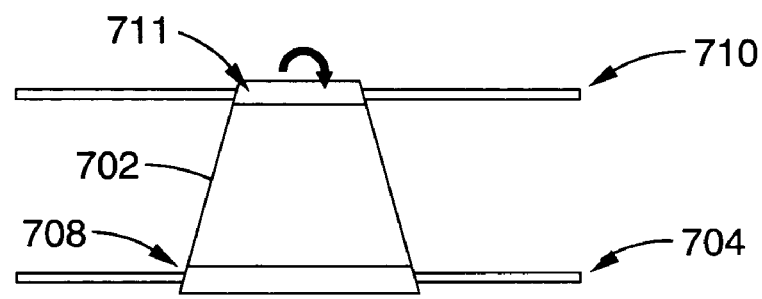

FIG. 36A shows a PTFE film 700 with a pattern 702 for trimming. FIG. 36B shows a step creating a channel for a hoop ring using a 0.015" mandrel 704 on one edge 706 of the trimmed pattern PTFE 702 and applying silicone adhesive, such as via a syringe 703, before flipping the ePTFE inward over the mandrel and silicone, thus creating the channel 708 per FIG. 36C. This is also done on the other side of the 4 sided pattern, except using a 0.009" mandrel 710 to form channel 711, as shown in FIGS. 36D–E. Exemplary silicone adhesive may be RTV or Heptane. Thereafter, the assembly of the two mandrels 704,710 within the double lumened skin is dried, such as for 20 minutes air dry and 20 minutes oven dry at 60 degrees C. The mandrels 704,710 are then removed and relatively large and small NiTi hoops are replaced into the large and smaller ePTFE channels, respectively (not shown).

Figure 36F:
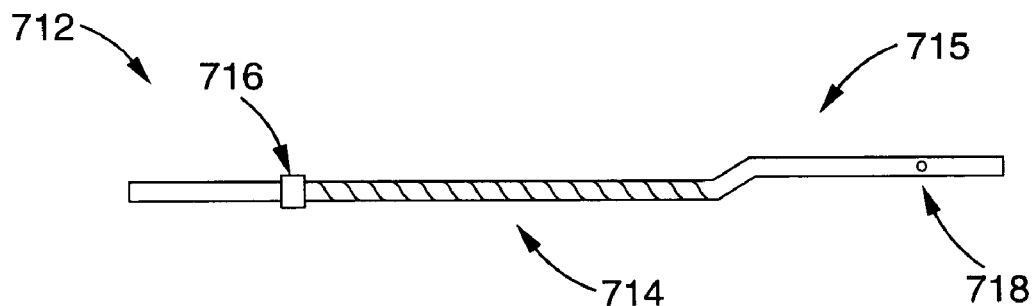
Figure 36G:
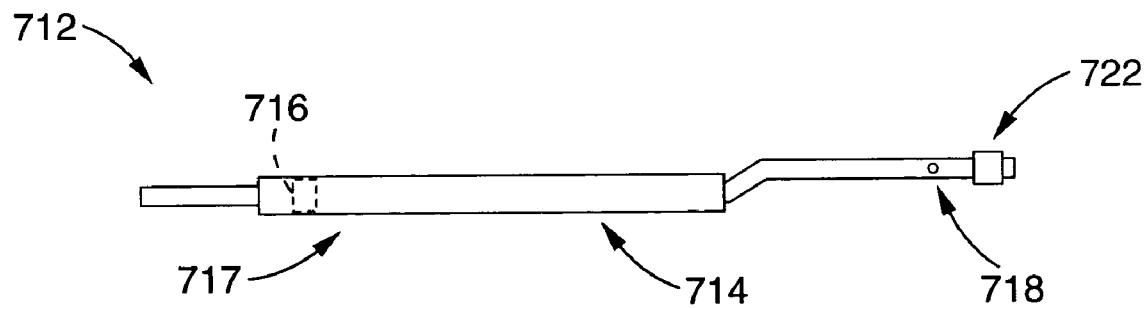
Figure 36H:
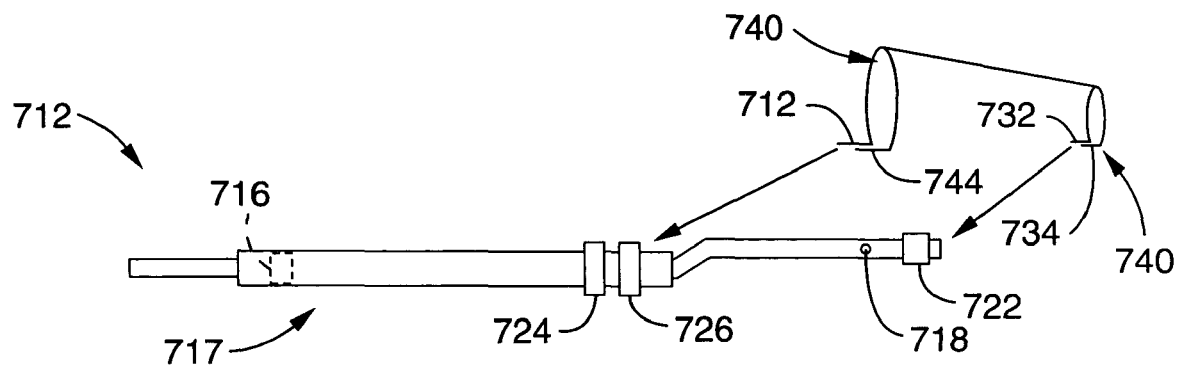
Figure 36I:
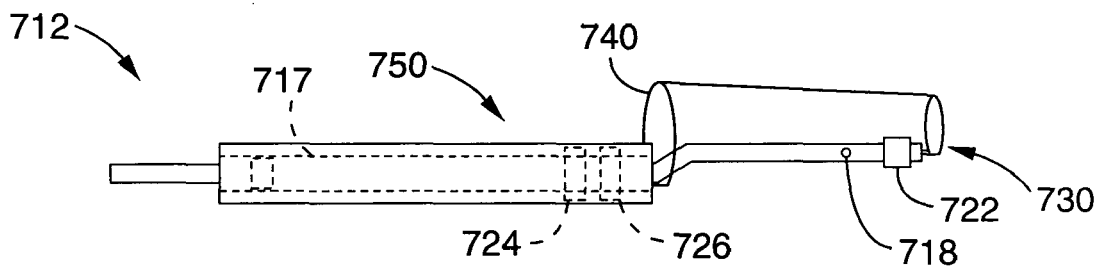

Next, preparation of a longitudinal support spine member is described by reference to FIGS. 36F–G. A hypotube 712 is sanded and has a coiled section 714 formed therein, such as by laser cutting. The coiled section 714 is stretched over a 0.019" mandrel to a total coil length of about 8 centimeters. A proximal marker band 716 is then bonded onto the hypotube 712, and may be 0.032"×0.035" inner diameter/outer diameter. Loctite 4011 may be used with a Primer 7701, for example to make this bond. Proximal marker band 716 is placed about 1 cm proximal from the end of the coiled section 714. An infusion hole 718 is also formed distal to the coiled section 714 and on a stand-off 715 portion extending distally from a bend in hypotube 712 that will become a mixing region. A polymer tubing 717 is bonded over the coiled section 714 and marker band (FIG. 36G), such as by heat melting or heat shrinking, and such as a PEBAX™ 63D modulus tubing having inner/outer diameters of 0.0395"× 0.050" trimmed to 9.5 cm long. This may be done for example by using an outer heat shrink FEP tubing, such as FEP 20 1:3:1 tubing commercially available from Zeus 3/32 that is heat shrunk over the PEBAX™ at 400 degrees F. At edges, shrink tubing from ICO Rally may be used. The PEBAX is then trimmed at its distal section, with about 1 cm removed. Next, a distal marker band 722 is bonded onto the hypotube distal to infusion hole 718, as shown in FIG. 36G. A band having id/od dimensions 0.032"×0.035" may be used, such as available from Noble-Met. Loctite 4011 and Primer 7701 may be used for bonding. The distal marker band 722 is bonded about 2 to 3 mm proximal of the distal end hole (not shown) of hypotube 712. Referring now to FIG. 36H, mid marker bands 724,726 are placed over the Pebax jacket 717, and may be for example 0.046"×0.048" ID/OD such as commercially available from Noble-Met.

Further to FIG. 36H, the sheet 702 is formed into a tube as it is adapted to hypotube 712 as follows. Two opposing ends 732,734 of distal hoop 730 located within channel 711 are brought together and inserted into a distal hole of the hypotube 712. Opposing ends 742,744 of proximal hoop 740 located within channel 708 are brought together and inserted underneath mid marker bands 734,726, as shown in FIG. 36H by arrow, and bonded there using Loctite 4011 and Primer 7701. The distal hoop 730 is glued into hypotube 712 using Loctite™ 4011 and Primer 7701. A second Pebax tubing 750 is then placed over mid marker bands 724, 726, and may be for example 0.050"×0.070" ID/OD. This tubing 750 is bonded using Zeus FEP heat shrink tubing at 400 deg F. ICO Rally tubing is shrunk around edges to make smooth.

Figure 36J:
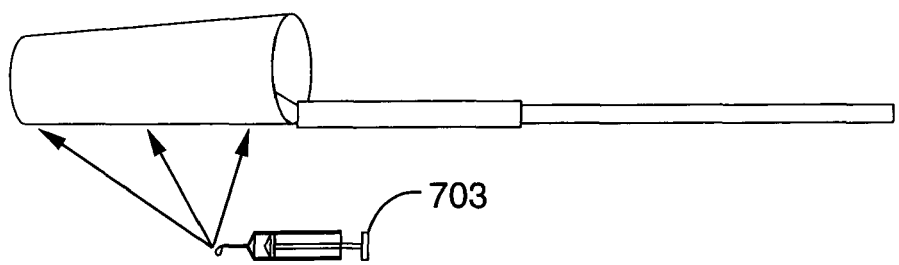

The tubing is completed per FIG. 36J by gluing, such as adhesive from a dispenser 703, one side to the hypotube 712 using Loctite 4011 and Primer 7701, with excess PTFE trimmed and additional glue applied to the edge. The remaining side is glued to hypotube 712 over the first PTFE bonded edge. Preferably this is done in a manner leaving infusion hole 718 exposed to the outside of the tubing.

A peel away or loading sheath are slid over, such as peel away by B-Braun or loading sheath by Cordis "Avanti", Part #504-608A.

Figure 36K:
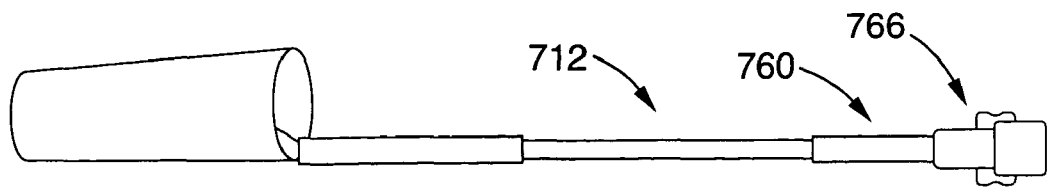

As shown in FIG. 36K, a strain relief 760 and luer 766 are bonded to the proximal end of hypotube 712, such as a female luer under the name "Qosina", Part #65206, using for example Loctite 498 and Primer 7701.

Another highly beneficial embodiment is shown in FIGS. 37–38B, wherein proximal and distal hoops 740, 730 are located within proximal and distal circumferential channels 708,711 loosely. Distal channel 730 includes a distal infusion port 718. Hypotube 712 along the spine includes a port 717 that communicates with distal infusion port 718 via channel 711. FIG. 38B shows increasing detail of this arrangement. FIG. 38A shows a cross section of the proximal adaption of proximal hoop 740, with ends 742,744 glued with an adhesive 770 within an outer tubing. A channel 713 remains for the delivery of fluids through port 717.

It should be appreciated that such pouches used for drug delivery into the outer blood flow stream may be separate than the channels housing the ring support members, and may be formed using other techniques. One illustrative example, for example, may include first forming the tubing with support members integrated into proximal and distal channels and then separately gluing or otherwise bonding additional strips of material over the outside surface of that tubing in a manner cooperating with a delivery port to fill the bladder formed.

The invention has been discussed in terms of certain preferred embodiments. One of skill in the art will recognize that various modifications may be made without departing from the scope of the invention. Although discussed primarily in terms of controlling blood flow to a branch vessel such as a renal artery of a blood vessel, it should be understood that the catheter of the invention could be used to deliver agent to branch vessels other than renal arteries, or to deliver to sites other than branch vessels, as for example where the catheter is used to deliver an agent to the wall defining the body lumen in which the catheter is positioned, such as a bile duct, ureter, and the like. Moreover, while certain features may be shown or discussed in relation to a particular embodiment, such individual features may be used on the various other embodiments of the invention.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for providing localized medical care to a renal system in a patient, comprising:
   positioning a distal end portion of a catheter at a location within the patient's aorta that is adjacent to an ostium of at least one renal artery extending from the aorta;
   using the distal end portion of the catheter from within the aorta at the location, directing a volume of fluid within the aorta to be locally delivered primarily into the at least one renal artery via its ostium;
   while locally delivering the volume of fluid into the at least one renal artery, allowing a substantial volume of aortic blood to flow downstream past the location and into the patient's downstream circulation downstream from the renal artery ostium;
   substantially isolating the volume of fluid being directed into the at least one renal artery from mixing with the substantial volume of aortic blood flowing downstream from the location; and
   conducting an interventional medical procedure at least in part with a guide or diagnostic catheter at an upstream location upstream from the location while locally directing the volume of fluid into the at least one renal artery, and while allowing the substantial volume of aortic blood to flow downstream from the ostium, and also while substantially isolating the volume of fluid from mixing with the substantial volume of aortic blood flowing downstream.

2. The method of claim 1, wherein the volume of fluid comprises an outer blood flow component of aortic blood, and further comprising:
   passively directing the outer blood flow component into the at least one renal artery at an increased pressure at the respective ostium that is artificially elevated by the catheter to be greater than a normal physiologic pressure at the ostium for that patient.

3. The method of claim 1, further comprising:
   preventing a portion of the aortic blood from passively flowing downstream across the location and past the renal artery ostium; and
   passively redirecting the portion of aortic blood toward the at least one renal artery ostium using the distal end portion of the catheter.

4. The method of claim 1, wherein the volume of fluid comprises a fluid agent, and further comprising:
   providing a proximal port at the proximal end portion of the catheter in fluid communication with a source of the fluid agent externally of the patient while the distal end portion of the catheter is positioned at the location;
   delivering a volume of the fluid agent through the catheter to the location within the aorta; and directing the volume of fluid agent to flow from the location within the aorta and principally into the at least one renal artery via its ostium.

5. The method of claim 1, wherein the interventional medical procedure further comprises: injecting a radiopaque contrast agent into the patient's arterial system at a location that is upstream from the renal ostium.

6. The method of claim 5, further comprising:
providing the volume of fluid being directed into the renal artery with an agent that is adapted to treat or protect the patient's renal system with respect to the radiopaque contrast agent being injected at the upstream location.

7. The method of claim 1, further comprising:
providing the volume of fluid being locally directed into the least one renal artery with an agent that comprises at least one of a vasodilator, an antioxidants, or a diuretic.

8. The method of claim 1, wherein the interventional medical procedure further comprises:
positioning a delivery device at least in part within the patient's aorta at an upstream location that is upstream from the renal artery ostium.

9. The method of claim 8, wherein the delivery device comprises an angiographic catheter.

10. The method of claim 8, wherein the delivery device comprises a guiding catheter.

11. The method of claim 8, wherein:
the delivery device is positioned at least in part within a coronary artery ostium.

12. The method of claim 8, wherein: the delivery device is positioned at least in part within a carotid artery ostium.

13. The method of claim 1, further comprising:
locally directing the volume of fluid into multiple renal arteries via multiple respective ostia that are located at unique, relatively spaced positions along the aorta, and wherein each kidney is perfused by at least a respective one of the multiple renal arteries.

14. The method of claim 13, wherein the volume of fluid comprises a fluid agent, and further comprising:
mixing the volume of fluid agent in an outer, circumferential region of the aortic blood flowing along the location adjacent the wall of the aorta and while substantially isolating the volume of agent from mixing with an inner region of aortic blood flowing downstream past the location and that is substantially surrounded by the outer, circumferential region; and
directing the aortic blood and mixed agent in the outer, circumferential region to principally flow into the multiple renal arteries via their respective ostia.

15. The method of claim 14, further comprising:
positioning a tubular member with a distal end portion of the tubular member located upstream from the location of the ostia and a proximal end portion of the tubular member located downstream from the location;
with the proximal and distal end portions at the downstream and upstream locations, respectively, providing the tubular member with a distally reducing tapered shape such that the proximal end portion has a first outer diameter that is sufficient to substantially circumferentially engage the aorta wall at the downstream location, and further such that the distal end portion has a second outer diameter that is sufficiently less than the inner diameter of the aorta wall at the upstream location; and
wherein the outer, circumferential region of aortic blood is located between an outer surface of the tubular member and the aortic wall between the distal tip of the distal end portion and the ostia.

16. The method of claim 15, further comprising:
delivering the volume of fluid agent into the outer, circumferential region of blood flow at a first isolated radial position; and
providing the shape of the tubular member with a mixing region having a different taper than other regions of the tubular member and that is associated with the first isolated circumferential position;
wherein the mixing region is adapted to enhance the mixing of the agent with blood circumferentially around the tubular member to thereby more evenly distribute the agent to renal arteries having respective ostia at respectively unique circumferential locations around the aorta at the location.

17. The method of claim 1, wherein the volume of aortic blood is allowed to flow passively downstream across the location during the delivery of the agent into the at least one renal artery.

18. A method as in claim 1, further comprising:
locally delivering at least one of a vasodilator, antioxidant, or diuretic agent substantially into a renal artery from the location within the aorta.

19. The method of claim 18, further comprising locally delivering a vasodilator into the at least one renal artery.

20. The method of claim 19, further comprising locally delivering at least one of papavarine, fenoldopam, calcium channel blockers, atrial natriuretic peptide (ANP), acetylcholine, nifedipine, nitroglycerine, nitroprusside, adenosine, dopamine, or theophylline, or combinations or blends thereof, into the at least one renal artery.

21. The method of claim 18, further comprising locally delivering an antioxidant into the at least one renal artery.

22. The method of claim 21, further comprising delivering acetylcysteine into the at least one renal artery.

23. The method of claim 18, further comprising delivering a diuretic agent into the at least one renal artery ostium.

24. The method of claim 23, further comprising delivering at least one of mannitol, or furosemide, or combinations or blends thereof, into the at least one renal artery.

25. A method for directing fluid to a renal system in a patient, comprising:
positioning a renal device at a location within the patient's aorta that is adjacent to an ostium of at least one renal artery extending from the aorta;
dividing a first portion of aortic flow and a second portion of aortic flow from an aortic blood flow within the aorta with the renal device;
directing the first portion of aortic blood flow into the at least one renal artery, while allowing the second portion to flow across the location and downstream of the ostium;
locally delivering a volume of fluid comprising a diagnostic, prophylactic or therapeutic agent the to at least one renal artery in the patient with the renal device; and
while locally delivering the volume of fluid to the at least one renal artery with the renal device, positioning a medical device within an aorta of the patient upstream from an ostium of the at least one renal artery along the aorta of the patient.

26. A method as claim 25, further comprising:
locally delivering at least one of a vasodilator, antioxidant, or diuretic agent substantially into a renal artery from the location within the aorta.

27. The method of claim 26, further comprising locally delivering a vasodilator into the at least one renal artery.

28. The method of claim 27, further comprising locally delivering at least one of paparavine, fenoldopam, calcium channel blockers, atrial natriuretic peptide (ANP), acetylcholine, nifedipine, nitroglycerine, nitroprusside, adenosine, dopamine, or theophylline, or combinations or blends thereof, into the at least one renal artery.

29. The method of claim 27, further comprising locally delivering an antioxidant into the at least one renal artery.

30. The method of claim 29, further comprising delivering acetylcysteine into the at least one renal artery.

31. The method of claim 26, further comprising delivering a diuretic agent into the at least one renal artery.

32. The method of claim 26, further comprising delivering at least one of mannitol, or furosemide, or combinations or blends thereof, into the at least one renal artery.

* * * * *